(12) United States Patent
Pasternak et al.

(10) Patent No.: US 6,500,927 B2
(45) Date of Patent: Dec. 31, 2002

(54) IDENTIFICATION AND CHARACTERIZATION OF MULTIPLE SPLICE VARIANTS OF THE MU-OPIOID RECEPTOR GENE

(75) Inventors: Gavril Pasternak, New York, NY (US); Ying-Xian Pan, New York, NY (US)

(73) Assignee: Memorial Sloan-Kettering Cancer Center, New York, NY (US)

( * ) Notice: Subject to any disclaimer, the term of this patent is extended or adjusted under 35 U.S.C. 154(b) by 0 days.

(21) Appl. No.: 09/761,962

(22) Filed: Jan. 17, 2001

(65) Prior Publication Data

US 2002/0077285 A1 Jun. 20, 2002

Related U.S. Application Data

(63) Continuation-in-part of application No. 09/743,862, filed as application No. PCT/US99/15974 on Jul. 15, 1999, now abandoned.
(60) Provisional application No. 60/092,980, filed on Jul. 16, 1998.

(51) Int. Cl.[7] .......................... C07K 1/00; C07K 14/00; C07K 17/00

(52) U.S. Cl. ..................................... 530/350

(58) Field of Search ..................... 530/350; 435/69.1, 435/7.2, 7.1; 536/23.5; 514/1, 2

(56) References Cited

U.S. PATENT DOCUMENTS 4,946,778 A   8/1990   Ladner et al.
6,103,492 A   8/2000   Yu

OTHER PUBLICATIONS

Abbadie et al. (1999) "Neurons in the dorsal column white matter of the spinal cord: complex neuropilin an unexpected location" Proc. Natl. Acad. Sci. USA 96:260–265.
Bare et al. (1994) "Expression of two variants of the human µ opioid receptor mRNA in SKN–SH cells and human brain" FEBS Lett. 354:213–6.
Chen et al. (1993) "Molecular cloning and functional expression of a µ–opioid receptor from rat brain"Mol. Pharmacol. 44:8–12.
Cole et al. (1985) "Monoclonal Antibodies and Cancer Therapy" Alan R. Liss, Inc., pp. 77–96.
Cote et al. (1983) "Generation of human monoclonal antibodies reactive with cellular antigens" Proc. Natl. Acad. Sci. USA 80:2026–2030.
Delfs et al. (1994) "Expression of µ opioid receptor mRNA in rat brain: an in situ hybridization study at the single cell level" J. Comp. Neurol. 345:46–68.

Elliott et al. (1994) "The NMDA receptor antagonists, LY274614 and MK–801, and the nitric oxide synthase inhibitor, NG–nitro–L–arginine, attenuate analgesic tolerance to the µ–opioid morphine but not to κ opioids" Pain 56:69–75.
Evans et al. (1981) "Establishment in culture of pluripotential cells from mouse embryos" Nature 292:154–6.
Giros et al. (1995) "Chromosomal localization of opioid peptide and receptor genes in the mouse" Life Sci. 56:369–375.
Guiramand et al. (1995) "Alternative splicing of the dopamine D2 receptor directs specificity of coupling to G–proteins" J. Biol. Chem. 270:7354–58.
Huse et al. (1989) "Generation of a large combinatorial library of the immunoglobulin repertoire in phage lambda" Science 246:1275–81.
Kolesnikov et al. (1994) "1–Aminocyclopropane carboxylic acid (ACPC) prevents µ and δ opioid tolerance" Life Sci. 55:1393–98.
Kolesnikov et al. (1993) "Blockade of tolerance to morphine but not to κ opioids by a nitric oxide synthase inhibitor" Proc. Natl. Acad. Sci. USA 90:5162–5166.
Liang et al. (1995) "Cloning and characterization of the promoter region of the mouse µ opioid receptor gene" Brain Res. 679:82–88.
Lowry et al. (1951) "Protein measurement with the folin phenol reagent" J. Biol. Chem. 193:265–75.
Lucas et al. (1995) "New players in the 5–HT receptor field: genes and knockouts" TiPS 16:246–252.
Lutz et al. (1992) "Opioid receptors and their pharmacological profiles" J. Receptor Res. 12:267–286.
Min et al. (1994) "Genomic structure analysis of promoter sequence of a mouse µ opioid receptor gene" Proc. Natl. Acad. Sci. USA 91:9081–85.
Morrison et al. (1984) "Chimeric human antibody molecules: mouse antigen–binding domains with human constant region domains" Proc. Natl. Acad. Sci. USA 81:6851–55.
Neuberger et al. (1984) "Recombinant antibodies possessing novel effector functions" Nature 312:604–8.
Olson et al. (1989) "Endogenous opiates: 1988" Peptides 10:1253–1280.

(List continued on next page.)

Primary Examiner—Gary L. Kunz
Assistant Examiner—Robert S. Landsman
(74) Attorney, Agent, or Firm—Frommer, Lawrence & Haug, LLP

(57) ABSTRACT

The present invention encompasses novel splice variant forms of the mu-opioid receptor-1 (MOR-1) and the polynucleotide sequences encoding the MOR-1 splice variants. The invention further encompasses methods of screening for compositions regulating the MOR-1 splice variant activities and the development of therapeutic modalities directed to regulating activity. Regulation of the MOR-1 splice variant activities may impact the physiologic processes of analgesia and weight management.

8 Claims, 34 Drawing Sheets

OTHER PUBLICATIONS

Pan et al. (1994) "Cloning, Expression and Classification of a $\kappa_3$–Related opioid receptor using Antisense Oligodeoxynucleotides" Regul. Pept. 54:217–218.

Pan et al. (1996) "Dissociation of affinity and efficacy in KOR–3 chimeras" FEBS Lett. 395:207–10.

Pasternak (1993) "Pharmacological mechanisms of opioid analgesics" Clin. Neuropharmacol. 16:1–18.

Pasternak et al. (1995) "Mapping of opioid receptors using antisense oligodeoxynucleotides: correlating their molecular biology and pharmacology" TiPS 16:344–50.

Reisine et al. (1993) "Molecular Biology of opioid receptors" Trends Neurosci. 16:506–510.

Reisine et al. (1996) "Opioid analgesics and antagonists" in Goodman & Gilman's "The pharmacological basis of therapeutics" 9th Ed. (Hardman et al. eds) McGraw–Hill pp. 521–555.

Robertson (1991) "Using embryonic stem cells to introduce mutations into the mouse germ line" Biol. Reprod. 44:238–245.

Rossi et al. (1997) "Antisense mapping of MOR–1 in rats: distinguishing between morphine and morphine–6β–glucuronide antinociception" J. Pharmacol. Exp. Ther. 281:101–114.

Rossi et al. (1996) "Naloxone sensitive orphanin FQ–induced analgesia in mice" Eur. J. Pharmacol. 311:R7–8.

Rossi et al. (1995) "Antisense mapping the MOR–1 opioid receptor: evidence for alternative splicing and a novel morphine–6β–glucuronide receptor" FEBS Lett. 369:192–196.

Sibinga et al. (1988) "Opioid peptides and opioid receptors in cells of the immune system" Annu. Rev. Immunol. 6:219–49.

Simon (1991) "Opioid receptors and endogenous opioid peptides" Medicinal Res. Rev. 11:357–374.

Standifer et al. (1997) "G proteins and opioid receptor–mediated signaling" Cell. Signal. 9:237–248.

Standifer et al. (1996) "Differential blockade of opioid analgesia by antisense oligodeoxynucleotides directed against various G protein αsubunits" Mol. Pharmacol. 50:293–298.

Takeda et al. (1985) "Construction of chimaeric processed immunoglobulin genes containing mouse variable and human constant region sequences" Nature 314:452–4.

Trujillo et al. (1991) "Inhibition of morphine tolerance and dependence by the NMDA receptor antagonist MK–801" Science 251:85–87.

van den Engh et al. (1992) "Estimating genomic distance from DNA sequence location in cell nuclei by a random walk model" Science 257:1410–1412.

Vanetti et al. (1992) "Cloning and expression of a novel mouse somatostatin receptor (SSTR2B)" FEBS Lett. 311:290–294.

Wang et al. (1993) "$\mu$ opiate receptor: cDNA cloning and expression " Proc. Natl. Acad. Sci. USA 90:10230–34.

Wolozin et al. (1981) "Classification of multiple morphine and enkephalin binding sites in the central nervous system" Proc. Natl. Acad. Sci. USA 78:6181–84.

Yasuda et al. (1993) "Cloning and functional comparison of $\kappa$ and $\delta$ opioid receptors from mouse brain" Proc. Natl. Acad. Sci. USA 90:6736–6740.

Zimprich et al. (1995) "Cloning and expression of an isoform of the rat $\mu$ opioid receptor (rMOR1B) which differs in agonist induced desensitization from rMOR1" FEBS Lett. 359:142–146.

Du et al. (1996) "Identification of a novel splice variant of the mouse mu opioid receptor" Soc. Neurosci. Ab. 22:695.5.

Du et al. (1997) "A splice variant of the mu opioid receptor is present in human SHSY–5Y cells" Soc. Neurosci. Ab. 23:479.3.

Leventhal et al. (1997) "Antisense mapping of the MOR–1 opioid receptor clone: modulation of hyperphagia induced by DAMGO" J. Pharmacol. Exp. Ther. 282:1402–1407.

Leventhal et al. (1996) "Antisense oligodeoxynucleotides against the MOR–1 clone alter weight and ingestive responses in rats" Brain Res. 719:78–84.

Kaufman, D., et al. J. Biol. Chem 270:15877–15883 (1995).

Rossi et al. (1996) Neurosci. Lett. 216: 1–4.

Rossi et al. (1994) Life Sci. 54:375–379.

MOR-1c

GGAACCCGAACACTCTTGAGTGCTCTCAGTTACAGCCTACCGAGTCCGCAGCAAGCATTC
AGAACCATGGACAGCAGCGCCGGCCCAGGGAACATCAGCGACTGCTCTGACCCCTTAGCT
CCTGCAAGTTGCTCCCCAGCACCTGGCTCCTGGCTCAACTTGTCCCACGTTGATGGCAAC
CAGTCCGACCCATGCGGTCCTAACCGCACGGGGCTTGGCGGGAGCCACAGCCTGTGCCCT
CAGACCGGCAGCCCTTCCATGGTCACAGCCATCACCATCATGGCCCTCTATTCTATCGTG
TGTGTAGTGGGCCTCTTTGGAAACTTCCTGGTCATGTATGTGATTGTAAGATATACCAAA
ATGAAGACTGCCACCAACATCTACATTTTCAACCTTGCTCTGGCAGATGCCTTAGCCACT
AGCACGCTGCCCTTTCAGAGTGTTAACTACCTGATGGGAACGTGGCCCTTTGGAAACATC
CTCTGCAAGATCGTGATCTCAATAGACTACTACAACATGTTCACCAGTATCTTCACCCTC
TGCACCATGAGTGTAGACCGCTACATTGCCGTCTGCCACCCGGTCAAGGCCCTGGATTTC
CGTACCCCCCGAAATGCCAAAATTGTCAATGTCTGCAACTGGATCCTCTCTTCTGCCATT
GGTCTGCCCGTAATGTTCATGGCAACCACAAAATACAGGCAGGGGTCCATAGATTGCACC
CTCACGTTCTCTCATCCCACATGGTACTGGGAGAACCTGCTCAAAATCTGTGTCTTCATC
TTCGCCTTCATCATGCCGGTCCTCATCATCACTGTGTGTTATGGACTGATGATCTTACGA
CTCAAGAGTGTCCGCATGCTGTCGGGCTCCAAAGAAAAGGACAGGAACCTGCGCAGGATC
ACCCGGATGGTGCTGGTGGTCGTGGCTGTATTTATTGTCTGCTGGACCCCCATCCACATC
TATGTCATCATCAAAGCACTGATCACGATTCCAGAAACCACTTTCCAGACTGTTTCCTGG
CACTTCTGCATTGCCTTGGGTTACACAAACAGCTGCCTGAACCCAGTTCTTTATGCGTTC
CTGGATGAAAACTTCAAACGATGTTTAGAGAGTTCTGCATCCCAACTTCCTCCACAATC
GAACAGCAAAACTCTGCTCGAATCCGTCAAAACACTAGGGAACACCCCTCCACGGCTAAT
<u>Exon 7</u>
ACAGTGGATCGAACTAACCACCAG/<u>CCAACCCTGGCAGTCAGCGTGGCCCAGATCTTTACA</u>
<u>Exon 8</u>
<u>GGATATCCTTCTCCGACTCATGTTGAAAAACCCTGCAAGAGTTGCATGGACAG/AGGAATG</u>
<u>Exon 9</u>
<u>AGGAACCTTCTTCCTGATGATGGCCCAAGACAGGAATCCGGGGAAGGCCAGCTTGGCAG/G</u>
<u>TGAATGTCATCCGAACACAGGGATGAGCTGGTGAGCAGTGTGG</u>

FIG. 2A

MOR-1g

Exon 1a
/TTTTACTGTCCTTGAGAATGGAGAGGATCAGCAAAGCTGGAAGCCCTCCAGGCTCATTTC

AGAGAGAATATTCCACAGAGCTTGAAGGCGCGGGATCTGGGCCGATGATGGAAGCTTTCT

CTAAGTCTGCATTCCAAAAGCTCAGACAGAGAGATGGAAATCAAGAGGGGAAGAGCTACC

TCAGATATACCAAAATGAAGACTGCCACCAACATCTACATTTTCAACCTTGCTCTGGCAG
ATGCCTTAGCCACTAGCACGCTGCCCTTTCAGAGTGTTAACTACCTGATGGGAACGTGGC
CCTTTGGAAACATCCTCTGCAAGATCGTGATCTCAATAGACTACTACAACATGTTCACCA
GTATCTTCACCCTCTGCACCATGAGTGTAGACCGCTACATTGCCGTCTGCCACCCGGTCA
AGGCCCTGGATTTCCGTACCCCCGAAATGCCAAAATTGTCAATGTCTGCAACTGGATCC
TCTCTTCTGCCATTGGTCTGCCCGTAATGTTCATGGCAACCACAAAATACAGGCAGGGGT
CCATAGATTGCACCCTCACGTTCTCTCATCCCACATGGTACTGGGAGAACCTGCTCAAAA
TCTGTGTCTTCATCTTCGCCTTCATCATGCCGGTCCTCATCATCACTGTGTGTTATGGAC
TGATGATCTTACGACTCAAGAGTGTCCGCATGCTGTCGGGCTCCAAAGAAAAGGACAGGA
ACCTGCGCAGGATCACCCGGATGGTGCTGGTGGTCGTGGCTGTATTTATTGTCTGCTGGA
CCCCCATCCACATCTATGTCATCATCAAAGCACTGATCACGATTCCAGAAACCACTTTCC
AGACTGTTTCCTGGCACTTCTGCATTGCCTTGGGTTACACAAACAGCTGCCTGAACCCAG
TTCTTTATGCGTTCCTGGATGAAAACTTCAAACGATGTTTTAGAGAGTTCTGCATCCCAA
CTTCCTCCACAATCGAACAGCAAAACTCTGCTCGAATCCGTCAAAACACTAGGGAACACC
CCTCCACGGCTAATACAGTGGATCGAACTAACCACCAGCTAGAAAATCTGGAAGCAGAAA
CTGCTCCATTGCCCTAACTGGGTCCCACGCCATCCAGACCCTCGCTAAACTTAGAGGCTG
CCATCTACTTGGAATCAGGTTGCTGTCAGGGTTTGTGGGAGGCTCTGGTTTCCTGGAAAA
GCATCTGATCCTGCATTCAAAGTCATTCTAACTGGGTC

FIG. 2B

MOR-1d

GGAACCCGAACACTCTTGAGTGCTCTCAGTTACAGCCTACCGAGTCCGCAGCAAGCATTC
AGAACCATGGACAGCAGCGCCGGCCCAGGGAACATCAGCGACTGCTCTGACCCCTTAGCT
CCTGCAAGTTGCTCCCCAGCACCTGGCTCCTGGCTCAACTTGTCCCACGTTGATGGCAAC
CAGTCCGACCCATGCGGTCCTAACCGCACGGGGCTTGGCGGGAGCCACAGCCTGTGCCCT
CAGACCGGCAGCCCTTCCATGGTCACAGCCATCACCATCATGGCCCTCTATTCTATCGTG
TGTGTAGTGGGCCTCTTTGGAAACTTCCTGGTCATGTATGTGATTGTAAGATATACCAAA
ATGAAGACTGCCACCAACATCTACATTTTCAACCTTGCTCTGGCAGATGCCTTAGCCACT
AGCACGCTGCCCTTTCAGAGTGTTAACTACCTGATGGGAACGTGGCCCTTTGGAAACATC
CTCTGCAAGATCGTGATCTCAATAGACTACTACAACATGTTCACCAGTATCTTCACCCTC
TGCACCATGAGTGTAGACCGCTACATTGCCGTCTGCCACCCGGTCAAGGCCCTGGATTTC
CGTACCCCCCGAAATGCCAAAATTGTCAATGTCTGCAACTGGATCCTCTCTTCTGCCATT
GGTCTGCCCGTAATGTTCATGGCAACCACAAAATACAGGCAGGGGTCCATAGATTGCACC
CTCACGTTCTCTCATCCCACATGGTACTGGGAGAACCTGCTCAAAATCTGTGTCTTCATC
TTCGCCTTCATCATGCCGGTCCTCATCATCACTGTGTGTTATGGACTGATGATCTTACGA
CTCAAGAGTGTCCGCATGCTGTCGGGCTCCAAAGAAAAGGACAGGAACCTGCGCAGGATC
ACCCGGATGGTGCTGGTGGTCGTGGCTGTATTTATTGTCTGCTGGACCCCCATCCACATC
TATGTCATCATCAAAGCACTGATCACGATTCCAGAAACCACTTTCCAGACTGTTTCCTGG
CACTTCTGCATTGCCTTGGGTTACACAAACAGCTGCCTGAACCCAGTTCTTTATGCGTTC
CTGGATGAAAACTTCAAACGATGTTTAGAGAGTTCTGCATCCCAACTTCCTCCACAATC
GAACAGCAAAACTCTGCTCGAATCCGTCAAAACACTAGGGAACACCCCTCCACGGCTAAT
<u>Exon 8</u>
<u>ACAGTGGATCGAACTAACCACCAG/AGGAATGAGGAACCTTCTTCCTGATGATGGCCCAAG</u>
<u>Exon 9</u>
<u>ACAGGAATCCGGGGAAGGCCAGCTTGGCAG/GTGAATGTCATCCGAACACAGGGATGAGCT</u>

<u>GGTGAGCAGTGTGG</u>

FIG. 2C

MOR-1e

GGAACCCGAACACTCTTGAGTGCTCTCAGTTACAGCCTACCGAGTCCGCAGCAAGCATTC
AGAACCATGGACAGCAGCGCCGGCCCAGGGAACATCAGCGACTGCTCTGACCCCTTAGCT
CCTGCAAGTTGCTCCCCAGCACCTGGCTCCTGGCTCAACTTGTCCCACGTTGATGGCAAC
CAGTCCGACCCATGCGGTCCTAACCGCACGGGGCTTGGCGGGAGCCACAGCCTGTGCCCT
CAGACCGGCAGCCCTTCCATGGTCACAGCCATCACCATCATGGCCCTCTATTCTATCGTG
TGTGTAGTGGGCCTCTTTGGAAACTTCCTGGTCATGTATGTGATTGTAAGATATACCAAA
ATGAAGACTGCCACCAACATCTACATTTTCAACCTTGCTCTGGCAGATGCCTTAGCCACT
AGCACGCTGCCCTTTCAGAGTGTTAACTACCTGATGGGAACGTGGCCCTTTGGAAACATC
CTCTGCAAGATCGTGATCTCAATAGACTACTACAACATGTTCACCAGTATCTTCACCCTC
TGCACCATGAGTGTAGACCGCTACATTGCCGTCTGCCACCCGGTCAAGGCCCTGGATTTC
CGTACCCCCCGAAATGCCAAAATTGTCAATGTCTGCAACTGGATCCTCTCTTCTGCCATT
GGTCTGCCCGTAATGTTCATGGCAACCACAAAATACAGGCAGGGGTCCATAGATTGCACC
CTCACGTTCTCTCATCCCACATGGTACTGGGAGAACCTGCTCAAAATCTGTTGCTTCATC
TTCGCCTTCATCATGCCGGTCCTCATCATCACTGTGTGTTATGGACTGATGATCTTACGA
CTCAAGAGTGTCCGCATGCTGTCGGGCTCCAAAGAAAAGGACAGGAACCTGCGCAGGATC
ACCCGGATGGTGCTGGTGGTCGTGGCTGTATTTATTGTCTGCTGGACCCCCATCCACATC
TATGTCATCATCAAAGCACTGATCACGATTCCAGAAACCACTTTCCAGACTGTTTCCTGG
CACTTCTGCATTGCCTTGGGTTACACAAACAGCTGCCTGAACCCAGTTCTTTATGCGTTC
CTGGATGAAAACTTCAAACGATGTTTTAGAGAGTTCTGCATCCCAACTTCCTCCACAATC
GAACAGCAAAACTCTGCTCGAATCCGTCAAAACACTAGGGAACACCCCTCCACGGCTAAT
<u>                                  Exon 6
ACAGTGGATCGAACTAACCACCAG/AAGAAAAAGCTGGACTCCCAGAGAGGGTGTGTACAG CATCCAGTGTGACCTGTCCCTTGTCTTTGAGCCTGGGGGCCATCTTCTTTCACAGCATAC</u>
<u>               Exon 7
ATTTCCTTGTATCCTCTCTGAAG/CCAACCCTGGCAGTCAGCGTGGCCCAGATCTTTACA</u>
<u>                                                        Exon 8
GGATATCCTTCTCCGACTCATGTTGAAAAACCCTGCAAGAGTTGCATGGACAG/AGGAATG</u>
<u>                                                             Exon 9
AGGAACCTTCTTCCTGATGATGGCCCAAGAGAGGAATCCGGGGAAGGCCAGCTTGGCAG/G</u>

<u>TGAATGTCATCCGAACACAGGGATGAGCTGGTGAGCAGTGTGG</u>

FIG. 2D

MOR-1h

Exon 1a
/TTTTACTGTCCTTGAGAATGGAGAGGATCAGCAAAGCTGGAAGCCCTCCAGGCTCATTTC

AGAGAGAATATTCCACAGAGCTTGAAGGCGCGGGATCTGGGCCGATGATGGAAGCTTTCT

CTAAGTCTGCATTCCAAAAGCTCAGACAGAGAGATGGAAATCAAGAGGGGAAGAGCTACC

TCAGATATACCAAAATGAAGACTGCCACCAACATCTACATTTTCAACCTTGCTCTGGCAG
ATGCCTTAGCCACTAGCACGCTGCCCTTTCAGAGTGTTAACTACCTGATGGGAACGTGGC
CCTTTGGAAACATCCTCTGCAAGATCGTGATCTCAATAGACTACTACAACATGTTCACCA
GTATCTTCACCCTCTGCACCATGAGTGTAGACCGCTACATTGCCGTCTGCCACCCGGTCA
AGGCCCTGGATTTCCGTACCCCCGAAATGCCAAAATTGTCAATGTCTGCAACTGGATCC
TCTCTTCTGCCATTGGTCTGCCCGTAATGTTCATGGCAACCACAAAATACAGGCAGGGGT
CCATAGATTGCACCCTCACGTTCTCTCATCCCACATGGTACTGGGAGAACCTGCTCAAAA
TCTGTGTCTTCATCTTCGCCTTCATCATGCCGGTCCTCATCATCACTGTGTGTTATGGAC
TGATGATCTTACGACTCAAGAGTGTCCGCATGCTGTCGGGCTCCAAAGAAAAGGACAGGA
ACCTGCGCAGGATCACCCGGATGGTGCTGGTGGTCGTGGCTGTATTTATTGTCTGCTGGA
CCCCCATCCACATCTATGTCATCATCAAAGCACTGATCACGATTCCAGAAACCACTTTCC
AGACTGTTTCCTGGCACTTCTGCATTGCCTTGGGTTACACAAACAGCTGCCTGAACCCAG
TTCTTTATGCGTTCCTGGATGAAAACTTCAAACGATGTTTTAGAGAGTTCTGCATCCCAA
CTTCCTCCACAATCGAACAGCAAAACTCTGCTCGAATCCGTCAAAACACTAGGGAACACC
                                                                               Exon 7
CCTCCACGGCTAATACAGTGGATCGAACTAACCACCAG/CCAACCCTGGCAGTCAGCGTG GCCCAGATCTTTACAGGATATCCTTCTCCGACTCATGTTGAAAAACCCTGCAAGAGTTGC
      Exon 8
ATGGACAG/AGGAATGAGGAACCTTCTTCCTGATGATGGCCCAAGAGAGGAATCCGGGGA
            Exon 9
AGGCCAGCTTGGCAG/GTGAATGTCATCCGAACACAGGGATGAGCTGGTGAGCAGTGTGG

```
     5'              11         21         31         41         51
   1 GGAAATCAAG AGGGGAAGAG TTACCTCAGG TCTTGTGCAG GTGCCTGCTG CTGTGAATTC
     CCTTTAGTTC TCCCCTTCTC AATGGAGTCC AGAACACGTC CACGGACGAC GACACTTAAG

5'              71         81         91          1         11
  61 ATGAAGACAA CACCCTCCCC TTTAGAAGAC AGTGCTTCAG AACACTCCCA ACTAGCCTCT
     TACTTCTGTT GTGGGAGGGG AAATCTTCTG TCACGAAGTG TTGTGAGGGT TGATCGGAGA

5'              31         41         51         61         71
 121 GGCTCTGATG TTCCACTTT
     CCGAGACTAC AAGGTGAAA
```

```
     5'              11         21         31         41         51
   1 CCTCCAGGCT CATTTCAGAG AGAATATTCC ACAGAGCTTG AAGGCGCGGG ATCTGGGCCG
     GGAGGTCCGA GTAAAGTCTC TCTTATAAGG TGTCTCGAAC TTCCGCGCCC TAGACCCGGC

5'              71         81         91          1         11
  61 ATGATGGAAG CTTTCTCTAA GTCTGCATTC CAAAAGCTCA GACAGAGAGA TGGAAATCAA
     TACTACCTTC GAAAGAGATT CAGACGTAAG GTTTTCGAGT CTGTCTCTCT ACCTTTAGTT
                         Exon 1a Exon 1b
     5'              31         41         51         61         71
 121 GAGGGGAAGA GTTACCTCAG GTCTTGTGCA GGTGCACTGC TGCTGTGAAT TCATGAAGAC
     CTCCCCTTCT CAATGGAGTC CAGAACACGT CCACGTGACG ACGACACTTA AGTACTTCTG 5'              91          1         11         21         31
 181 AACACCCTCC CCTTTAGAAG ACAGTGCTTC ACAACACTCC CAACTAGCCT CTGGCTCTGA
     TTGTGGGAGG GGAAATCTTC TGTCACGAAG TGTTGTGAGG GTTGATCGGA GACCGAGACT
                                       Exon 1
     5'              51         61         71         81         91
 241 TGTTCACTTT GTCCCCTCTT CTGAAGCAGG GCTTGTCCTT GTAAGAAACT GAGGAGCCTA
     ACAAGTGAAA CAGGGGAGAA GACTTCGTCC CGAACAGGAA CATTCTTTGA CTCCTCGGAT 5'              11         21         31         41         51
 301 GGGCAGCTGT GAGAGGAAGA GGCTGGGGCA CCTGGAACCC GAACACTCTT GAGTGCTCTC
     CCCGTCGACA CTCTCCTTCT CCGACCCCGT GGACCTTGGG CTTGTGAGAA CTCACGAGAG

```
                                                          Exon 1a Exon 1b
5'            11         21         31         41         51  |
  1  ATTCCAAAAG CTCAGACAGA GAGATGGAAG TCAAGAGGGG AAGAGTTACC TCAG GTCTTG
     TAAGGTTTTC GAGTCTGTCT CTCTACCTTC AGTTCTCCCC TTCTCAATGG AGTC CAGAAC 5'            71         81         91          1         11
 61  TGCAGGTGCA CTGCTGCTGT GAATTCATGA AGACAACACC CTCCCCTTTA GTAGACAGCG
     ACGTCCACGT GACGACGACA CTTAAGTACT TCTGTTGTGG GAGGGGAAAT CATCTGTCGC 5'            31         41         51         61         71
121  CTTCACAACA CTCCCAACTA GCCTCTGGCT CTGATGTTCA CTTTGTCCCC TCTTCTGAAG
     GAAGTGTTGT GAGGGTTGAT CGGAGACCGA GACTACAAGT GAAACAGGGG AGAAGACTTC Exon 2
5'        |    91          1         11         21         31
181  C AGATGTACC AAAATGAAGA CTGCCACCAA CATCTACATT TTCAACCTTG CTCTGGCAGA
     G TCTACATGG TTTTACTTCT GACGGTGGTT GTAGATGTAA AAGTTGGAAC GAGACCGTCT 5'            51         61         71         81         91
241  TGCCTTAGCC ACTAGCACGC TGCCCAAG
     ACGGAATCGG TGATCGTGCG ACGGGTTC
```

FIG. 2H

MOR-1f

```
5'            11         21         31         41         51
  1  GGAACCCGAA CACTCTTGAG TGCTCTCAGT TACAGCCTAC CGAGTCCGCA GCAAGCATTC
     CCTTGGGCTT GTGAGAACTC ACGAGAGTCA ATGTCGGATG GCTCAGGCGT CGTTCGTAAG

5'            71         81         91          1         11
 61  AGAACCATGG ACAGCAGCGC CGGCCCAGGG AACATCAGCG ACTGCTCTGA CCCCTTAGCT
     TCTTGGTACC TGTCGTCGCG GCCGGGTCCC TTGTAGTCGC TGACGAGACT GGGGAATCGA

5'            31         41         51         61         71
121  CCTGCAAGTT GCTCCCCAGC ACCTGGCTCC TGGCTCAACT TGTCCCACGT TGATGGCAAC
     GGACGTTCAA CGAGGGGTCG TGGACCGAGG ACCGAGTTGA ACAGGGTGCA ACTACCGTTG

5'            91          1         11         21         31
181  CAGTCCGACC CATGCGGTCC TAACCGCACG GGGCTTGGCG GGAGCCACAG CCTGTGCCCT
     GTCAGGCTGG GTACGCCAGG ATTGGCGTGC CCCGAACCGC CTCGGTGTC GGACACGGGA

5'            51         61         71         81         91
241  CAGACCGGCA GCCCTTCCAT GGTCACAGCC ATCACCATCA TGGCCCTCTA TTCTATCGTG
     GTCTGGCCGT CGGGAAGGTA CCAGTGTCGG TAGTGGTAGT ACCGGGAGAT AAGATAGCAC

5'            11         21         31         41         51
301  TGTGTAGTGG GCCTCTTTGG AAACTTCCTG GTCATGTATG TGATTGTAAG ATATACCAAA
     ACACATCACC CGGAGAAACC TTTGAAGGAC CAGTACATAC ACTAACATTC TATATGGTTT
```

FIG. 2I

```
     5'                71         81         91          1         11
   361 ATGAAGACTG CCACCAACAT CTACATTTTC AACCTTGCTC TGGCAGATGC CTTAGCCACT
       TACTTCTGAC GGTGGTTGTA GATGTAAAAG TTGGAACGAG ACCGTCTACG GAATCGGTGA

5'                31         41         51         61         71
   421 AGCACGCTGC CCTTTCAGAG TGTTAACTAC CTGATGGGAA CGTGGCCCTT TGGAAACATC
       TCGTGCGACG GGAAAGTCTC ACAATTGATG GACTACCCTT GCACCGGGAA ACCTTTGTAG

5'                91          1         11         21         31
   481 CTCTGCAAGA TCGTGATCTC AATAGACTAC TACAACATGT TCACCAGTAT CTTCACCCTC
       GAGACGTTCT AGCACTAGAG TTATCTGATG ATGTTGTACA AGTGGTCATA GAAGTGGGAG

5'                51         61         71         81         91
   541 TGCACCATGA GTGTAGACCG CTACATTGCC GTCTGCCACC CGGTCAAGGC CCTGGATTTC
       ACGTGGTACT CACATCTGGC GATGTAACGG CAGACGGTGG GCCAGTTCCG GGACCTAAAG

5'                11         21         31         41         51
   601 CGTACCCCCC GAAATGCCAA AATTGTCAAT GTCTGCAACT GGATCCTCTC TTCTGCCATT
       GCATGGGGGG CTTTACGGTT TTAACAGTTA CAGACGTTGA CCTAGGAGAG AAGACGGTAA

5'                71         81         91          1         11
   661 GGTCTGCCCG TAATGTTCAT GGCAACCACA AAATACAGGC AGGGGTCCAT AGATTGCACC
       CCAGACGGGC ATTACAAGTA CCGTTGGTGT TTTATGTCCG TCCCCAGGTA TCTAACGTGG

5'                31         41         51         61         71
   721 CTCACGTTCT CTCATCCCAC ATGGTACTGG GAGAACCTGC TCAAAATCTG TGTCTTCATC
       GAGTGCAAGA GAGTAGGGTG TACCATGACC CTCTTGGACG AGTTTTAGAC ACAGAAGTAG

5'                91          1         11         21         31
   781 TTCGCCTTCA TCATGCCGGT CCTCATCATC ACTGTGTGTT ATGGACTGAT GATCTTACGA
       AAGCGGAAGT AGTACGGCCA GGAGTAGTAG TGACACACAA TACCTGACTA CTAGAATGCT

5'                51         61         71         81         91
   841 CTCAAGAGTG TCCGCATGCT GTCGGGCTCC AAAGAAAAGG ACAGGAACCT GCGCAGGATC
       GAGTTCTCAC AGGCGTACGA CAGCCCGAGG TTTCTTTTCC TGTCCTTGGA CGCGTCCTAG

5'                11         21         31         41         51
   901 ACCCGGATGG TGCTGGTGGT CGTGGCTGTA TTTATTGTCT GCTGGACCCC CATCCACATC
       TGGGCCTACC ACGACCACCA GCACCGACAT AAATAACAGA CGACCTGGGG GTAGGTGTAG

5'                71         81         91          1         11
   961 TATGTCATCA TCAAAGCACT GATCACGATT CCAGAAACCA CTTTCCAGAC TGTTTCCTGG
       ATACAGTAGT AGTTTCGTGA CTAGTGCTAA GGTCTTTGGT GAAAGGTCTG ACAAAGGACC

5'                31         41         51         61         71
  1021 CACTTCTGCA TTGCCTTGGG TTACACAAAC AGCTGCCTGA ACCCAGTTCT TTATGCGTTC
       GTGAAGACGT AACGGAACCC AATGTGTTTG TCGACGGACT TGGGTCAAGA AATACGCAAG
```

FIG. 2J

```
       5'           91          1           11          21          31
     1081 CTGGATGAAA  ACTTCAAACG  ATGTTTTAGA  GAGTTCTGCA  TCCCAACTTC  CTCCACAATC
          GACCTACTTT  TGAAGTTTGC  TACAAAATCT  CTCAAGACGT  AGGGTTGAAG  GAGGTGTTAG

5'           51          61          71          81          91
     1141 GAACAGCAAA  ACTCTGCTCG  AATCCGTCAA  AACACTAGGG  AACACCCCTC  CACGGCTAAT
          CTTGTCGTTT  TGAGACGAGC  TTAGGCAGTT  TTGTGATCCC  TTGTGGGGAG  GTGCCGATTA
                                        Exon 10
       5'           11          21          31          41          51
     1201 ACAGTGGATC  GAACTAACCA  CCAGGCACCA  TGTGCATGCG  TGCCTGGAGC  CAACAGAGGT
          TGTCACCTAG  CTTGATTGGT  GGTCCGTGGT  ACACGTACGC  ACGGACCTCG  GTTGTCTCCA 5'           71          81          91          1           11
     1261 CAAACGAAGG  CATCAGATCT  TCTGGATCTG  GAATTGGAGA  CAGTTGGGAG  CCACCAGGCA
          GTTTGCTTCC  GTAGTCTAGA  AGACCTAGAC  CTTAACCTCT  GTCAACCCTC  GGTGGTCCGT 5'           31          41          51          61          71
     1321 GATGCTGAAA  CCAACCCAGG  TCCTTACGAA  GGCAGCAAGT  GCGCTGAACC  ACTAGCCATC
          CTACGACTTT  GGTTGGGTCC  AGGAATGCTT  CCGTCGTTCA  CGCGACTTGG  TGATCGGTAG
                                              Exon 6
       5'           91          1           11          21          31
     1381 TCTCTGGTCC  CGCTATATTA  GCATTGTGCT  AAGAAAAAGC  TGGACTCCCA  GAGAGGGTGT
          AGAGACCAGG  GCGATATAAT  CGTAACACGA  TTCTTTTTCG  ACCTGAGGGT  CTCTCCCACA 5'           51          61          71          81          91
     1441 GTACAGCATC  CAGTGTGACC  TGTCCCTTGT  CTTTGAGCCT  GGGGGCCATC  TTCTTTCACA
          CATGTCGTAG  GTCACACTGG  ACAGGGAACA  GAAACTCGGA  CCCCCGGTAG  AAGAAAGTGT
                                              Exon 7
       5'           11          21          31          41          51
     1501 GCATACCATT  TCCTTGTATC  CTCTCTGAAG  CCAACCCTGG  CAGTCAGCGT  GGCCCAGATC
          CGTATGGTAA  AGGAACATAG  GAGAGACTTC  GGTTGGGACC  GTCAGTCGCA  CCGGGTCTAG
                                                                      Exon 8
       5'           71          81          91          1           11
     1561 TTTACAGGAT  ATCCTTCTCC  GACTCATGTT  GAAAAACCCT  GCAAGAGTTG  CATGGACAGA
          AAATGTCCTA  TAGGAAGAGG  CTGAGTACAA  CTTTTTGGGA  CGTTCTCAAC  GTACCTGTCT 5'           31          41          51          61          71
     1621 GGAATGAGGA  ACCTTCTTCC  TGATGATGGC  CCAAGACAGG  AATCCGGGGA  AGGCCAGCTT
          CCTTACTCCT  TGGAAGAAGG  ACTACTACCG  GGTTCTGTCC  TTAGGCCCCT  TCCGGTCGAA 5'           91          1           11          21
     1681 GGCAGGTGAA  TGTCATCCGA  ACACAGGGAT  GAGCTGGTGA  GCAGTGTGG
          CCGTCCACTT  ACAGTAGGCT  TGTGTCCCTA  CTCGACCACT  CGTCACACC
```

FIG. 2K

MOR-1bII

```
     5'          11          21          31          41          51
  1  GGAACCCGAA  CACTCTTGAG  TGCTCTCAGT  TACAGCCTAC  CGAGTCCGCA  GCAAGCATTC
     CCTTGGGCTT  GTGAGAACTC  ACGAGAGTCA  ATGTCGGATG  GCTCAGGCGT  CGTTCGTAAG

5'          71          81          91           1          11
 61  AGAACCATGG  ACAGCAGCGC  CGGCCCAGGG  AACATCAGCG  ACTGCTCTGA  CCCCTTAGCT
     TCTTGGTACC  TGTCGTCGCG  GCCGGGTCCC  TTGTAGTCGC  TGACGAGACT  GGGGAATCGA

5'          31          41          51          61          71
121  CCTGCAAGTT  GCTCCCCAGC  ACCTGGCTCC  TGGCTCAACT  TGTCCCACGT  TGATGGCAAC
     GGACGTTCAA  CGAGGGGTCG  TGGACCGAGG  ACCGAGTTGA  ACAGGGTGCA  ACTACCGTTG

5'          91           1          11          21          31
181  CAGTCCGACC  CATGCGGTCC  TAACCGCACG  GGGCTTGGCG  GGAGCCACAG  CCTGTGCCCT
     GTCAGGCTGG  GTACGCCAGG  ATTGGCGTGC  CCCGAACCGC  CCTCGGTGTC  GGACACGGGA

5'          51          61          71          81          91
241  CAGACCGGCA  GCCCTTCCAT  GGTCACAGCC  ATCACCATCA  TGGCCCTCTA  TTCTATCGTG
     GTCTGGCCGT  CGGGAAGGTA  CCAGTGTCGG  TAGTGGTAGT  ACCGGGAGAT  AAGATAGCAC

5'          11          21          31          41          51
301  TGTGTAGTGG  GCCTCTTTGG  AAACTTCCTG  GTCATGTATG  TGATTGTAAG  ATATACCAAA
     ACACATCACC  CGGAGAAACC  TTTGAAGGAC  CAGTACATAC  ACTAACATTC  TATATGGTTT

5'          71          81          91           1          11
361  ATGAAGACTG  CCACCAACAT  CTACATTTTC  AACCTTGCTC  TGGCAGATGC  CTTAGCCACT
     TACTTCTGAC  GGTGGTTGTA  GATGTAAAAG  TTGGAACGAG  ACCGTCTACG  GAATCGGTGA

5'          31          41          51          61          71
421  AGCACGCTGC  CCTTTCAGAG  TGTTAACTAC  CTGATGGGAA  CGTGGCCCTT  TGGAAACATC
     TCGTGCGACG  GGAAAGTCTC  ACAATTGATG  GACTACCCTT  GCACCGGGAA  ACCTTTGTAG

5'          91           1          11          21          31
481  CTCTGCAAGA  TCGTGATCTC  AATAGACTAC  TACAACATGT  TCACCAGTAT  CTTCACCCTC
     GAGACGTTCT  AGCACTAGAG  TTATCTGATG  ATGTTGTACA  AGTGGTCATA  GAAGTGGGAG

5'          51          61          71          81          91
541  TGCACCATGA  GTGTAGACCG  CTACATTGCC  GTCTGCCACC  CGGTCAAGGC  CCTGGATTTC
     ACGTGGTACT  CACATCTGGC  GATGTAACGG  CAGACGGTGG  GCCAGTTCCG  GGACCTAAAG

5'          11          21          31          41          51
601  CGTACCCCCC  GAAATGCCAA  AATTGTCAAT  GTCTGCAACT  GGATCCTCTC  TTCTGCCATT
     GCATGGGGGG  CTTTACGGTT  TTAACAGTTA  CAGACGTTGA  CCTAGGAGAG  AAGACGGTAA

5'          71          81          91           1          11
661  GGTCTGCCCG  TAATGTTCAT  GGCAACCACA  AAATACAGGC  AGGGGTCCAT  AGATTGCACC
     CCAGACGGGC  ATTACAAGTA  CCGTTGGTGT  TTTATGTCCG  TCCCCAGGTA  TCTAACGTGG
```

FIG. 2L

```
       5'            31         41         51         61         71
   721 CTCACGTTCT CTCATCCCAC ATGGTACTGG GAGAACCTGC TCAAAATCTG TGTCTTCATC
       GAGTGCAAGA GAGTAGGGTG TACCATGACC CTCTTGGACG AGTTTTAGAC ACAGAAGTAG

5'            91          1         11         21         31
   781 TTCGCCTTCA TCATGCCGGT CCTCATCATC ACTGTGTGTT ATGGACTGAT GATCTTACGA
       AAGCGGAAGT AGTACGGCCA GGAGTAGTAG TGACACACAA TACCTGACTA CTAGAATGCT

5'            51         61         71         81         91
   841 CTCAAGAGTG TCCGCATGCT GTCGGGCTCC AAAGAAAAGG ACAGGAACCT GCGCAGGATC
       GAGTTCTCAC AGGCGTACGA CAGCCCGAGG TTTCTTTTCC TGTCCTTGGA CGCGTCCTAG

5'            11         21         31         41         51
   901 ACCCGGATGG TGCTGGTGGT CGTGGCTGTA TTTATTGTCT GCTGGACCCC CATCCACATC
       TGGGCCTACC ACGACCACCA GCACCGACAT AAATAACAGA CGACCTGGGG GTAGGTGTAG

5'            71         81         91          1         11
   961 TATGTCATCA TCAAAGCACT GATCACGATT CCAGAAACCA CTTTCCAGAC TGTTTCCTGG
       ATACAGTAGT AGTTTCGTGA CTAGTGCTAA GGTCTTTGGT GAAAGGTCTG ACAAAGGACC

5'            31         41         51         61         71
  1021 CACTTCTGCA TTGCCTTGGG TTACACAAAC AGCTGCCTGA ACCCAGTTCT TTATGCGTTC
       GTGAAGACGT AACGGAACCC AATGTGTTTG TCGACGGACT TGGGTCAAGA AATACGCAAG

5'            91          1         11         21         31
  1081 CTGGATGAAA ACTTCAAACG ATGTTTTAGA GAGTTCTGCA TCCCAACTTC CTCCACAATC
       GACCTACTTT TGAAGTTTGC TACAAAATCT CTCAAGACGT AGGGTTGAAG GAGGTGTTAG

5'            51         61         71         81         91
  1141 GAACAGCAAA ACTCTGCTCG AATCCGTCAA AACACTAGGG AACACCCCTC CACGGCTAAT
       CTTGTCGTTT TGAGACGAGC TTAGGCAGTT TTCTGATCCC TTGTGGGGAG GTGCCGATTA
                                Exon 5b
       5'            11         21 |       31         41         51
  1201 ACAGTGGATC GAACTAACCA CCAG AAGCTT TTAATGTGGA GAGCTATGCC TACATTCAAG
       TGTCACCTAG CTTGATTGGT GGTC TTCGAA AATTACACCT CTCGATACGG ATGTAAGTTC 5'            71         81         91          1         11
  1261 AGACACTTGG CTATCATGTT AAGCCTTGAT AATTAGGGCA CCAAAGGGGA CAAGTGTCAA
       TCTGTGAACC GATAGTACAA TTCGGAACTA TTAATCCCGT GGTTTCCCCT GTTCACAGTT 5'            31         41         51         61         71
  1321 ATCAAGATGC TGTTTTTGTT TTTGTTTTTT GTTTTTTGTT TTTTCTGGTT CCATCAAGTT
       TAGTTCTACG ACAAAAACAA AAACAAAAAA CAAAAAACAA AAAAGACCAA GGTAGTTCAA 5'            91          1         11         21         31
  1381 CTTGTAGAAC ACTATTATGG TTAGCAATGC TCAATAGACA ATGTCAGGGG GTGTGACATA
       GAACATCTTG TGATAATACC AATCGTTACG AGTTATCTGT TACAGTCCCC CACACTGTAT
```

FIG. 2M

```
5'          51         61         71         81         91
1441 TTTTAGATGT AGAAGCACTA CACTGTCCCA ACTCCATAGT TGGAAGAGCA CCTCGTACTA
     AAAATCTACA TCTTCGTGAT GTGACAGGGT TGAGGTATCA ACCTTCTCGT GGAGCATGAT

5'          11         21         31         41         51
1501 TCAGGCTTGA CAAGTCCCCT GCAGGCCACC AGGCCCAAAG CTGTGAATTG AGCCGTGGTT
     AGTCCGAACT GTTCAGGGGA CGTCCGGTGG TCCGGGTTTC GACACTTAAC TCGGCACCAA

5'          71         81         91          1         11
1561 TAAACCTGTA TGAAAATAAG TAGCAATGTC TCAGAATTCA AGAAATTCAG AATTCTAAAA
     ATTTGGACAT ACTTTTATTC ATCGTTACAG AGTCTTAAGT TCTTTAAGTC TTAAGATTTT

5'          31         41         51         61         71
1621 CTGATTGTTA ATCTCTCACT CCCATGCATT CAAATGTGTC CTGAATACAT CCACAGACAC
     GACTAACAAT TAGAGAGTGA GGGTACGTAA GTTTACACAG GACTTATGTA GGTGTCTGTG

5'          91          1         11         21         31
1681 ACAAAATACT AAAACTCTCT CTGGAAGCAG AGCTTGTGCT TCGTTTGGGT TTCATTTTCT
     TGTTTTATGA TTTTGAGAGA GACCTTCGTC TCGAACACGA AGCAAACCCA AAGTAAAAGA

5'          51         61         71         81         91
1741 TTGTTTGTTT GTTTGTTTGT TTGTTTGTTT TGCTTTGTTT GAAGCCTACC GCTTTCTGGC
     AACAAACAAA CAAACAAACA AACAAACAAA ACGAAACAAA CTTCGGATGG CGAAAGACCG

5'          11         21         31         41         51
1801 TATAATTATG AGAAGGCACT CTGTCAGCCT TAGGGTATGT TTTTCTCTAA TTAAATTGCA
     ATATTAATAC TCTTCCGTGA GACAGTCGGA ATCCCATACA AAAAGAGATT AATTTAACGT

5'          71         81         91          1         11
1861 TGTTGCTAAG TGTTAGGCTT GTAAATGACA CGTTCTTTTG TTTTGAATAC AATATGTTTG
     ACAACGATTC ACAATCCGAA CATTTACTGT GCAAGAAAAC AAAACTTATG TTATACAAAC

Exon 5a
5'          |31         41         51         61         71
1921 CAG|AAAATAG ATTTATTTTG AAAAGGCATA TACACAGAAC TGGGAGAAGC ACACCAAAGA
     GTC|TTTTATC TAAATAAAAC TTTTCCGTAT ATGTGTCTTG ACCCTCTTCG TGTGGTTTCT 5'          91          1         11         21         31
1981 TATTTTGTTA CCATATGGCA AATGTAACCA TAGAGAGCAG AGTACCTAAT GCTGGTGCCA
     ATAAAACAAT GGTATACCGT TTACATTGGT ATCTCTCGTC TCATGGATTA CGACCACGGT 5'          51         61         71         81         91
2041 ACCCC
     TGGGG
```

FIG. 2N

MOR-1a

```
  5'             11         21         31         41         51
  1 GGAACCCGAA CACTCTTGAG TGCTCTCAGT TACAGCCTAC CGAGTCCGCA GCAAGCATTC
    CCTTGGGCTT GTGAGAACTC ACGAGAGTCA ATGTCGGATG GCTCAGGCGT CGTTCGTAAG

5'             71         81         91          1         11
 61 AGAACCATGG ACAGCAGCGC CGGCCCAGGG AACATCAGCG ACTGCTCTGA CCCCTTAGCT
    TCTTGGTACC TGTCGTCGCG GCCGGGTCCC TTGTAGTCGC TGACGAGACT GGGGAATCGA

5'             31         41         51         61         71
121 CCTGCAAGTT GCTCCCCAGC ACCTGGCTCC TGGCTCAACT TGTCCCACGT TGATGGCAAC
    GGACGTTCAA CGAGGGGTCG TGGACCGAGG ACCGAGTTGA ACAGGGTGCA ACTACCGTTG

5'             91          1         11         21         31
181 CAGTCCGACC CATGCGGTCC TAACCGCACG GGGCTTGGCG GGAGCCACAG CCTGTGCCCT
    GTCAGGCTGG GTACGCCAGG ATTGGCGTGC CCCGAACCGC CCTCGGTGTC GGACACGGGA

5'             51         61         71         81         91
241 CAGACCGGCA GCCCTTCCAT GGTCACAGCC ATCACCATCA TGGCCCTCTA TTCTATCGTG
    GTCTGGCCGT CGGGAAGGTA CCAGTGTCGG TAGTGGTAGT ACCGGGAGAT AAGATAGCAC

5'             11         21         31         41         51
301 TGTGTAGTGG GCCTCTTTGG AAACTTCCTG GTCATGTATG TGATTGTAAG ATATACCAAA
    ACACATCACC CGGAGAAACC TTTGAAGGAC CAGTACATAC ACTAACATTC TATATGGTTT

5'             71         81         91          1         11
361 ATGAAGACTG CCACCAACAT CTACATTTTC AACCTTGCTC TGGCAGATGC CTTAGCCACT
    TACTTCTGAC GGTGGTTGTA GATGTAAAAG TTGGAACGAG ACCGTCTACG GAATCGGTGA

5'             31         41         51         61         71
421 AGCACGCTGC CCTTTCAGAG TGTTAACTAC CTGATGGGAA CGTGGCCCTT TGGAAACATC
    TCGTGCGACG GGAAAGTCTC ACAATTGATG GACTACCCTT GCACCGGGAA ACCTTTGTAG

5'             91          1         11         21         31
481 CTCTGCAAGA TCGTGATCTC AATAGACTAC TACAACATGT TCACCAGTAT CTTCACCCTC
    GAGACGTTCT AGCACTAGAG TTATCTGATG ATGTTGTACA AGTGGTCATA GAAGTGGGAG

5'             51         61         71         81         91
541 TGCACCATGA GTGTAGACCG CTACATTGCC GTCTGCCACC CGGTCAAGGC CCTGGATTTC
    ACGTGGTACT CACATCTGGC GATGTAACGG CAGACGGTGG GCCAGTTCCG GGACCTAAAG

5'             11         21         31         41         51
601 CGTACCCCCC GAAATGCCAA AATTGTCAAT GTCTGCAACT GGATCCTCTC TTCTGCCATT
    GCATGGGGGG CTTTACGGTT TTAACAGTTA CAGACGTTGA CCTAGGAGAG AAGACGGTAA

5'             71         81         91          1         11
661 GGTCTGCCCG TAATGTTCAT GGCAACCACA AAATACAGGC AGGGGTCCAT AGATTGCACC
    CCAGACGGGC ATTACAAGTA CCGTTGGTGT TTTATGTCCG TCCCCAGGTA TCTAACGTGG
```

FIG. 20

```
       5'              31         41         51         61         71
   721 CTCACGTTCT CTCATCCCAC ATGGTACTGG GAGAACCTGC TCAAAATCTG TGTCTTCATC
       GAGTGCAAGA GAGTAGGGTG TACCATGACC CTCTTGGACG AGTTTTAGAC ACAGAAGTAG

5'              91          1         11         21         31
   781 TTCGCCTTCA TCATGCCGGT CCTCATCATC ACTGTGTGTT ATGGACTGAT GATCTTACGA
       AAGCGGAAGT AGTACGGCCA GGAGTAGTAG TGACACACAA TACCTGACTA CTAGAATGCT

5'              51         61         71         81         91
   841 CTCAAGAGTG TCCGCATGCT GTCGGGCTCC AAAGAAAAGG ACAGGAACCT GCGCAGGATC
       GAGTTCTCAC AGGCGTACGA CAGCCCGAGG TTTCTTTTCC TGTCCTTGGA CGCGTCCTAG

5'              11         21         31         41         51
   901 ACCCGGATGG TGCTGGTGGT CGTGGCTGTA TTTATTGTCT GCTGGACCCC CATCCACATC
       TGGGCCTACC ACGACCACCA GCACCGACAT AAATAACAGA CGACCTGGGG GTAGGTGTAG

5'              71         81         91          1         11
   961 TATGTCATCA TCAAAGCACT GATCACGATT CCAGAAACCA CTTTCCAGAC TGTTTCCTGG
       ATACAGTAGT AGTTTCGTGA CTAGTGCTAA GGTCTTTGGT GAAAGGTCTG ACAAAGGACC

5'              31         41         51         61         71
  1021 CACTTCTGCA TTGCCTTGGG TTACACAAAC AGCTGCCTGA ACCCAGTTCT TTATGCGTTC
       GTGAAGACGT AACGGAACCC AATGTGTTTG TCGACGGACT GGGTCAAGA AATACGCAAG

5'              91          1         11         21         31
  1081 CTGGATGAAA ACTTCAAACG ATGTTTTAGA GAGTTCTGCA TCCCAACTTC CTCCACAATC
       GACCTACTTT TGAAGTTTGC TACAAAATCT CTCAAGACGT AGGGTTGAAG GAGGTGTTAG

5'              51         61         71         81         91
  1141 GAACAGCAAA ACTCTGCTCG AATCCGTCAA AACACTAGGG AACACCCCTC CACGGCTAAT
       CTTGTCGTTT TGAGACGAGC TTAGGCAGTT TTGTGATCCC TTGTGGGGAG GTGCCGATTA
                                            Exon 3a
       5'              11         21         31         41         51
  1201 ACAGTGGATC GAACTAACCA CCAGTATGT GCTTCTAGA ATTATGTATA ACATATAAAA
       TGTCACCTAG CTTGATTGGT GGTCATACA CGAAAGATCT TAATACATAT TGTATATTTT 5'              71         81         91          1         11
  1261 ACACAGCACC TGATACCAGT CTAAGATTTA GATCCTTAAG GAGGTCGGTT ACTGGAGAAT
       TGTGTCGTGG ACTATGGTCA GATTCTAAAT CTAGGAATTC CTCCAGCCAA TGACCTCTTA 5'              31         41         51         61         71
  1321 CCAGCCAAGC CTAAAAATAG AGAGGGAGTA GGGGACCAAA TTCTG
       GGTCGGTTCG GATTTTATC TCTCCCTCAT CCCCTGGTTT AAGAC
```

FIG. 2P

MOR-1bI

```
              11         21         31         41         51
  1 GGAACCCGAA CACTCTTGAG TGCTCTCAGT TACAGCCTAC CGAGTCCGCA GCAAGCATTC
    CCTTGGGCTT GTGAGAACTC ACGAGAGTCA ATGTCGGATG GCTCAGGCGT CGTTCGTAAG

5'         71         81         91          1         11
 61 AGAACCATGG ACAGCAGCGC CGGCCCAGGG AACATCAGCG ACTGCTCTGA CCCCTTAGCT
    TCTTGGTACC TGTCGTCGCG GCCGGGTCCC TTGTAGTCGC TGACGAGACT GGGGAATCGA

5'         31         41         51         61         71
121 CCTGCAAGTT GCTCCCCAGC ACCTGGCTCC TGGCTCAACT TGTCCCACGT TGATGGCAAC
    GGACGTTCAA CGAGGGGTCG TGGACCGAGG ACCGAGTTGA ACAGGGTGCA ACTACCGTTG

5'         91          1         11         21         31
181 CAGTCCGACC CATGCGGTCC TAACCGCACG GGGCTTGGCG GGAGCCACAG CCTGTGCCCT
    GTCAGGCTGG GTACGCCAGG ATTGGCGTGC CCCGAACCGC CCTCGGTGTC GGACACGGGA

5'         51         61         71         81         91
241 CAGACCGGCA GCCCTTCCAT GGTCACAGCC ATCACCATCA TGGCCCTCTA TTCTATCGTG
    GTCTGGCCGT CGGGAAGGTA CCAGTGTCGG TAGTGGTAGT ACCGGGAGAT AAGATAGCAC

5'         11         21         31         41         51
301 TGTGTAGTGG GCCTCTTTGG AAACTTCCTG GTCATGTATG TGATTGTAAG ATATACCAAA
    ACACATCACC CGGAGAAACC TTTGAAGGAC CAGTACATAC ACTAACATTC TATATGGTTT

5'         71         81         91          1         11
361 ATGAAGACTG CCACCAACAT CTACATTTTC AACCTTGCTC TGGCAGATGC CTTAGCCACT
    TACTTCTGAC GGTGGTTGTA GATGTAAAAG TTGGAACGAG ACCGTCTACG GAATCGGTGA

5'         31         41         51         61         71
421 AGCACGCTGC CCTTTCAGAG TGTTAACTAC CTGATGGGAA CGTGGCCCTT TGGAAACATC
    TCGTGCGACG GGAAAGTCTC ACAATTGATG GACTACCCTT GCACCGGGAA ACCTTTGTAG

5'         91          1         11         21         31
481 CTCTGCAAGA TCGTGATCTC AATAGACTAC TACAACATGT TCACCAGTAT CTTCACCCTC
    GAGACGTTCT AGCACTAGAG TTATCTGATG ATGTTGTACA AGTGGTCATA GAAGTGGGAG

5'         51         61         71         81         91
541 TGCACCATGA GTGTAGACCG CTACATTGCC GTCTGCCACC CGGTCAAGGC CCTGGATTTC
    ACGTGGTACT CACATCTGGC GATGTAACGG CAGACGGTGG GCCAGTTCCG GGACCTAAAG

5'         11         21         31         41         51
601 CGTACCCCCC GAAATGCCAA AATTGTCAAT GTCTGCAACT GGATCCTCTC TTCTGCCATT
    GCATGGGGGG CTTTACGGTT TTAACAGTTA CAGACGTTGA CCTAGGAGAG AAGACGGTAA

5'         71         81         91          1         11
661 GGTCTGCCCG TAATGTTCAT GGCAACCACA AAATACAGGC AGGGGTCCAT AGATTGCACC
    CCAGACGGGC ATTACAAGTA CCGTTGGTGT TTTATGTCCG TCCCCAGGTA TCTAACGTGG
```

FIG. 2Q

```
       5'               31         41         51         61         71
     721 CTCACGTTCT CTCATCCCAC ATGGTACTGG GAGAACCTGC TCAAAATCTG TGTCTTCATC
         GAGTGCAAGA GAGTAGGGTG TACCATGACC CTCTTGGACG AGTTTTAGAC ACAGAAGTAG

5'               91          1         11         21         31
     781 TTCGCCTTCA TCATGCCGGT CCTCATCATC ACTGTGTGTT ATGGACTGAT GATCTTACGA
         AAGCGGAAGT AGTACGGCCA GGAGTAGTAG TGACACACAA TACCTGACTA CTAGAATGCT

5'               51         61         71         81         91
     841 CTCAAGAGTG TCCGCATGCT GTCGGGCTCC AAAGAAAAGG ACAGGAACCT GCGCAGGATC
         GAGTTCTCAC AGGCGTACGA CAGCCCGAGG TTTCTTTTCC TGTCCTTGGA CGCGTCCTAG

5'               11         21         31         41         51
     901 ACCCGGATGG TGCTGGTGGT CGTGGCTGTA TTTATTGTCT GCTGGACCCC CATCCACATC
         TGGGCCTACC ACGACCACCA GCACCGACAT AAATAACAGA CGACCTGGGG GTAGGTGTAG

5'               71         81         91          1         11
     961 TATGTCATCA TCAAAGCACT GATCACGATT CCAGAAACCA CTTTCCAGAC TGTTTCCTGG
         ATACAGTAGT AGTTTCGTGA CTAGTGCTAA GGTCTTTGGT GAAAGGTCTG ACAAAGGACC

5'               31         41         51         61         71
    1021 CACTTCTGCA TTGCCTTGGG TTACACAAAC AGCTGCCTGA ACCCAGTTCT TTATGCGTTC
         GTGAAGACGT AACGGAACCC AATGTGTTTG TCGACGGACT TGGGTCAAGA AATACGCAAG

5'               91          1         11         21         31
    1081 CTGGATGAAA ACTTCAAACG ATGTTTTAGA GAGTTCTGCA TCCCAACTTC CTCCACAATC
         GACCTACTTT TGAAGTTTGC TACAAAATCT CTCAAGACGT AGGGTTGAAG GAGGTGTTAG

5'               51         61         71         81         91
    1141 GAACAGCAAA ACTCTGCTCG AATCCGTCAA AACACTAGGG AACACCCCTC CACGGCTAAT
         CTTGTCGTTT TGAGACGAGC TTAGGCAGTT TTGTGATCCC TTGTGGGGAG GTGCCGATTA
                                            Exon 5a
       5'               11         21   |     31         41         51
    1201 ACAGTGGATC GAACTAACCA CCAG AAAATA GATTTATTTT GAAAAGGCAT ATACACAGAA
         TGTCACCTAG CTTGATTGGT GGTC TTTTAT CTAAATAAAA CTTTTCCGTA TATGTGTCTT 5'               71         81         91          1         11
    1261 CTGGGAGAAG CACACCAAAG ATATTTTGTT ACCATATGGC AAATGTAACC ATAGAGAGCA
         GACCCTCTTC GTGTGGTTTC TATAAAACAA TGGTATACCG TTTACATTGG TATCTCTCGT 5'               31         41         51         61         71
    1321 GAGTACCTAA TGCTGGTGCC AACCCC
         CTCATGGATT ACGACCACGG TTGGGG
```

FIG. 2R

MOR-1i

```
                                                    Exon 11
5'           11         21         31         41    |    51
  1 GGGAACACCC CTCCACGGCT AATACAGTGG ATCGAACTAA CCACCAGTGT GTATGAGTGC
    CCCTTGTGGG GAGGTGCCGA TTATGTCACC TAGCTTGATT GGTGGTCACA CATACTCACG 5'           71         81         91         1          11
 61 TATGCCCACA GGGACCAGAA GATGGTATCA GACCTTCTAG AACTGAAGTA GTGAGCAGTC
    ATACGGGTGT CCCTGGTCTT CTACCATAGT CTGGAAGATC TTGACTTCAT CACTCGTCAG
                        Exon 5b
5'           31         41         51         61         71
121 CCCACCCCCA CCCCCCGCAA TAAAATAGAT TTATTTTGAA AAGGCATATA CACAGAACTG
    GGGTGGGGGT GGGGGGCGTT ATTTTATCTA AATAAAACTT TTCCGTATAT GTGTCTTGAC

5'           91
181 GGAGAAGCAC ACC
    CCTCTTCGTG TGG
```

FIG. 2S

MOR-1j

```
                                                       Exon 12
  1 gggaacaccc ctccacggct aatacagtgg atcgaactaa ccaccaggag cctcagtcag
 61 cggagacatg atgtgaatga acggactgat tagacaaggt ttcctgaaca ctgagataca
121 aaacaaatag agagcttact agagaaaatt cgtagcccga aaattcaatt atagaaacaa
181 atgagtgtta gagtagatat ggtaaggcct cagagaggtt ttatttcacg actaacaaca
241 tgacccaagg cacctaatcc atggtgatta gattacaaag acaattctag tgcctgggcc
301 agagaaatgt ttgtctccca cagacaagcc tcacacttca gtaatgaaat gagtaaatta
361 aatcggtgag caagatggtg ggaggagtca aaatattttc atgccttcct gtggaactcc
421 aaaggaagac caacacagtc aactaacctg gctcttggtg gctctcagag ctgaacaacc
    aaccaaagag cactcatgag ctagacctag gcctctttta cacgtgtagc agatgtgcgt
    ctccatcttc atgtgggtcc ccccaacaag taaagtagca gctgtctcta aagctgttgc
    ctgtctggct tcggtggaag aagatgtgat tcgcttaacc ctgaagtgac ttgatatgca
      Exon 5a
    gggaaaatag atttattttg aaaaggcata tacacagaac tgggagaagc acacc
```

FIG. 2T hMOR-1-610302

Exon 4c

G GAT AGA ACT AAT CAT CAG / TGC CTA CCT ATA CCT TCC CTG TCT TGC TGG

GCT CTA GAG CAT GGC CGC TTG GTT GTG TAC CCT GGA CCA CTG CAA GGA CCT

CTT GTC AGA TAT GAC CTC CCA GCT

FIG. 2U

MOR-1

```
1     gctccctccc ttccactcag agagtggcgc tttggggatg ctaaggatgc gcctccgtgt
61    acttctaagg tgggaggggg ctacaagcag aggagaatat cggacgctca gacgttccat
121   tctgcctgcc gctcttctct ggttccacta gggcttgtcc ttgtaagaaa ctgacggagc
181   ctagggcagc tgtgagagga agaggctggg gcgcctggaa cccgaacact cttgagtgct
241   ctcagttaca gcctaccgag tccgcagcaa gcattcagaa ccatggacag cagcgccggc
301   ccagggaaca tcagcgactg ctctgacccc ttagctcctg caagttgctc cccagcacct
361   ggctcctggc tcaacttgtc ccacgttgat ggcaaccagt ccgacccatg cggtcctaac
421   cgcacggggc ttggcgggag ccacagcctg tgccctcaga ccggcagccc ttccatggtc
481   acagccatca ccatcatggc cctctattct atcgtgtgtg tagtgggcct ctttggaaac
541   ttcctggtca tgtatgtgat tgtaagatat accaaaatga agactgccac caacatctac
601   attttcaacc ttgctctggc agatgcctta gccactagca cgctgccctt tcagagtgtt
661   aactacctga tgggaacgtg gcccttttgga aacatcctct gcaagatcgt gatctcaata
721   gactactaca acatgttcac cagtatcttc accctctgca ccatgagtgt agaccgctac
781   attgccgtct gccaccctggt caaggccctg gatttccgta ccccccgaaa tgccaaaatt
841   gtcaatgtct gcaactggat cctctcttct gccattggtc tgcccgtaat gttcatggca
901   accacaaaat acaggcaggg gtccatagat tgcacccctca cgttctctca tcccacatgg
961   tactgggaga acctgctcaa aatctgtgtc ttcatcttcg ccttcatcat gccggtcctc
1021  atcatcactg tgtgttatgg actgatgatc ttacgactca agagtgtccg catgctgtcg
1081  ggctccaaag aaaaggacag gaacctgcgc aggatcaccc ggatggtgct ggtggtcgtg
1141  gctgtattta ttgtctgctg gacccccatc cacatctatg tcatcatcaa agcactgatc
1201  acgattccag aaaccacttt ccagactgtt tcctggcact ctgcattgc cttgggttac
1261  acaaacagct gcctgaaccc agttctttat gcgttcctgg atgaaaactt caacgatgtg
1321  tttagagagt tctgcatccc aacttcctcc aacatcgaac agcaaaactc tgctcgaatc
1381  cgtcaaaaca ctagggaaca cccctccacg gctaatacag tggatcgaac taaccaccag
1441  ctagaaaatc tggaagcaga aactgctcca ttgccctaac tgggtcccac gccatccaga
1501  ccctcgctaa acttagaggc tgccatctac ttggaatcag gttgctgtca gggtttgtgg
1561  gaggctctgg tttcctggaa aagcatctga tcctgcattc aaagtcattc
```

FIG. 2V

MOR-1C

MDSSAGPGNISDCSDPLAPASCSPAPGSWLNLSHV
DGNQSDPCGPNRTGLGGSHSLCPQTGSPSMVTAIT
IMALYSIVCVVGLFGNFLVMYVIVRYTKMKTATNI
YIFNLALADALATSTLPFQSVNYLMGTWPFGNILC
KIVISIDYYNMFTSIFTLCTMSVDRYIAVCHPVKA
LDFRTPRNAKIVNVCNWILSSAIGLPVMFMATTKY
RQGSIDCTLTFSHPTWYWENLLKICVFIFAFIMPV
LIITVCYGLMILRLKSVRMLSGSKEKDRNLRRITR
MVLVVVAVFIVCWTPIHIYVIIKALITIPETTFQT
VSWHFCIALGYTNSCLNPVLYAFLDENFKRCFREF
CIPTSSTIEQQNSARIRQNTREHPSTANTVDRTNH
Q ⌐Exon 7                                          Exon 8⌐
Q ⌐PTLAVSVAQIFTGYPSPTHVEKPCKSCMDR⌐GM
                              Exon 9⌐
RNLLPDDGPRQESGEGQLG⌐R

FIG. 3A

MOR-1G

⌐Exon 1a
⌐MERISKAGSPPGSFQREYSTELEGAGSGPMMEAF
SKSAFQKLRQRDGNQEGKSYLRYTKMKTATNIYIF
NLALADALATSTLPFQSVNYLMGTWPFGNILCKIV
ISIDYYNMFTSIFTLCTMSVDRYIAVCHPVKALDF
RTPRNAKIVNVCNWILSSAIGLPVMFMATTKYRQG
SIDCTLTFSHPTWYWENLLKICVFIFAFIMPVLII
TVCYGLMILRLKSVRMLSGSKEKDRNLRRITRMVL
VVVAVFIVCWTPIHIYVIIKALITIPETTFQTVSW
HFCIALGYTNSCLNPVLYAFLDENFKRCFREFCIP
TSSTIEQQNSARIRQNTREHPSTANTVDRTNHQLE
NLEAETAPLP

FIG. 3B

MOR-1D

M D S S A G P G N I S D C S D P L A P A S C S P A P G S W L N L S H V
D G N Q S D P C G P N R T G L G G S H S L C P Q T G S P S M V T A I T
I M A L Y S I V C V V G L F G N F L V M Y V I V R Y T K M K T A T N I
Y I F N L A L A D A L A T S T L P F Q S V N Y L M G T W P F G N I L C
K I V I S I D Y Y N M F T S I F T L C T M S V D R Y I A V C H P V K A
L D F R T P R N A K I V N V C N W I L S S A I G L P V M F M A T T K Y
R Q G S I D C T L T F S H P T W Y E N L L K I C V F I F A F I M P V
L I I T V C Y G L M I L R L K S V R M L S G S K E K D R N L R R I T R
M V L V V V A V F I V C W T P I H I Y V I I K A L I T I P E T T F Q T
V S W H F C I A L G Y T N S C L N P V L Y A F L D E N F K R C F R E F
C I P T S S T I E Q Q N S A R I R Q N T R E H P S T A N T V D R T N H
⌐Exon 8
Q ⌐R N E E P S

FIG. 3C

MOR-1E

M D S S A G P G N I S D C S D P L A P A S C S P A P G S W L N L S H V
D G N Q S D P C G P N R T G L G G S H S L C P Q T G S P S M V T A I T
I M A L Y S I V C V V G L F G N F L V M Y V I V R Y T K M K T A T N I
Y I F N L A L A D A L A T S T L P F Q S V N Y L M G T W P F G N I L C
K I V I S I D Y Y N M F T S I F T L C T M S V D R Y I A V C H P V K A
L D F R T P R N A K I V N V C N W I L S S A I G L P V M F M A T T K Y
R Q G S I D C T L T F S H P T W Y E N L L K I C V F I F A F I M P V
L I I T V C Y G L M I L R L K S V R M L S G S K E K D R N L R R I T R
M V L V V V A V F I V C W T P I H I Y V I I K A L I T I P E T T F Q T
V S W H F C I A L G Y T N S C L N P V L Y A F L D E N F K R C F R E F
C I P T S S T I E Q Q N S A R I R Q N T R E H P S T A N T V D R T N H
⌐Exon 6
Q ⌐K K K L D S Q R G C V Q H P V

FIG. 3D

MOR-1H

Exon 1a
M E R I S K A G S P P G S F Q R E Y S T E L E G A G S G P M M E A F
S K S A F Q K L R Q R D G N Q E G K S Y L R Y T K M K T A T N I Y I F
N L A L A D A L A T S T L P F Q S V N Y L M G T W P F G N I L C K I V
I S I D Y Y N M F T S I F T L C T M S V D R Y I A V C H P V K A L D F
R T P R N A K I V N V C N W I L S S A I G L P V M F M A T T K Y R Q G
S I D C T L T F S H P T W Y W E N L L K I C V F I F A F I M P V L I I
T V C Y G L M I L R L K S V R M L S G S K E K D R N L R R I T R M V L
V V V A V F I V C W T P I H I Y V I I K A L I T I P E T T F Q T V S W
H F C I A L G Y T N S C L N P V L Y A F L D E N F K R C F R E F C I P
T S S T I E Q Q N S A R I R Q N T R E H P S T A N T V D R T N H Q Exon 7                                                                Exon 8
P T L A V S V A Q I F T G Y P S P T H V E K P C K S C M D R  G M R Exon 9
N L L P D D G P R Q E S G E G Q L G  R

FIG. 3E

MOR-1I

Exon 3                    Exon 11
E H P S T A N T V D R T N H Q  C V

FIG. 3F

MOR-1J

Exon 3                    Exon 12
E H P S T A N T V D R T N H Q  E P Q S A E T

FIG. 3G hMOR-1-610302

Exon 3     Exon 5
D R T N H Q  C L P I P S L S C W A L E H G R L V V Y P G P L Q
G P L V R Y D L P A

FIG. 3H

MOR-1A

```
       N              11         21         31         41         51
       1  MDSSAGPGNI SDCSDPLAPA SCSPAPGSWL NLSHVDGNQS DPCGPNRTGL GGSHSLCPQT

N              71         81         91          1         11
      61  GSPSMVTAIT IMALYSIVCV VGLFGNFLVM YVIVRYTKMK TATNIYIFNL ALADALATST

N              31         41         51         61         71
     121  LPFQSVNYLM GTWPFGNILC KIVISIDYYN MFTSIFTLCT MSVDRYIAVC HPVKALDFRT

N              91          1         11         21         31
     181  PRNAKIVNVC NWILSSAIGL PVMFMATTKY RQGSIDCTLT FSHPTWYWEN LLKICVFIFA

N              51         61         71         81         91
     241  FIMPVLIITV CYGLMILRLK SVRMLSGSKE KDRNLRRITR MVLVVVAVFI VCWTPIHIYV

N              11         21         31         41         51
     301  IIKALITIPE TTFQTVSWHF CIALGYTNSC LNPVLYAFLD ENFKRCFREF CIPTSSTIEQ

N              71         81    Exon 3a
     361  QNSARIRQNT REHPSTANTV DRTNHQ|VCAF
```

FIG. 3I

MOR-1BI

```
       N              11         21         31         41         51
       1  MDSSAGPGNI SDCSDPLAPA SCSPAPGSWL NLSHVDGNQS DPCGPNRTGL GGSHSLCPQT

N              71         81         91          1         11
      61  GSPSMVTAIT IMALYSIVCV VGLFGNFLVM YVIVRYTKMK TATNIYIFNL ALADALATST

N              31         41         51         61         71
     121  LPFQSVNYLM GTWPFGNILC KIVISIDYYN MFTSIFTLCT MSVDRYIAVC HPVKALDFRT

N              91          1         11         21         31
     181  PRNAKIVNVC NWILSSAIGL PVMFMATTKY RQGSIDCTLT FSHPTWYWEN LLKICVFIFA

N              51         61         71         81         91
     241  FIMPVLIITV CYGLMILRLK SVRMLSGSKE KDRNLRRITR MVLVVVAVFI VCWTPIHIYV

N              11         21         31         41         51
     301  IIKALITIPE TTFQTVSWHF CIALGYTNSC LNPVLYAFLDE NFKRCFREF CIPTSSTIEQ

N              71         81    Exon 5b
     361  QNSARIRQNT REHPSTANTV DRTNHQ|KIDL F
```

FIG. 3J

MOR-1BII

```
N           11          21          31          41          51
  1 MDSSAGPGNI SDCSDPLAPA SCSPAPGSWL NLSHVDGNQS DPCGPNRTGL GGSHSLCPQT

N           71          81          91           1          11
 61 GSPSMVTAIT IMALYSIVCV VGLFGNFLVM YVIVRYTKMK TATNIYIFNL ALADALATST

N           31          41          51          61          71
121 LPFQSVNYLM GTWPFGNILC KIVISIDYYN MFTSIFTLCT MSVDRYIAV  CHPVKALDFRT

N           91           1          11          21          31
181 PRNAKIVNVC NWILSSAIGL PVMFMATTKY RQGSIDCTLT FSHPTWYWEN LLKICVFIFA

N           51          61          71          81          91
241 FIMPVLIITV CYGLMILRLK SVRMLSGSKE KDRNLRRITR MVLVVVAVFI VCWTPIHIYV

N           11          21          31          41          51
301 IIKALITIPE TTFQTVSWHF CIALGYTNSC LNPVLYAFLD ENFKRCFREF CIPTSSTIEQ
                                    Exon 5b
N           71          81        ┌  91           1
361 QNSARIRQNT REHPSTANTV DRTNHQ KLLM WRAMPTFKRH LAIMLSLDN
```

FIG. 3K

MOR-1F

```
N            11          21          31          41          51
  1  MDSSAGPGNI  SDCSDPLAPA  SCSPAPGSWL  NLSHVDGNQS  DPCGPNRTGL  GGSHSLCPQT

N            71          81          91           1          11
 61  GSPSMVTAIT  IMALYSIVCV  VGLFGNFLVM  YVIVRYTKMK  TATNIYIFNL  ALADALATST

N            31          41          51          61          71
121  LPFQSVNYLM  GTWPFGNILC  KIVISIDYYN  MFTSIFTLCT  MSVDRYIAVC  HPVKALDFRT

N            91           1          11         21-          31
181  PRNAKIVNVC  NWILSSAIGL  PVMFMATTKY  RQGSIDCTLT  FSHPTWYWEN  LLKICVFIFA

N            51          61          71          81          91
241  FIMPVLIITV  CYGLMILRLK  SVRMLSGSKE  KDRNLRRITR  MVLVVVAVFI  VCWTPIHIYV

N            11          21          31          41          51
301  IIKALITIPE  TTFQTVSWHF  CIALGYTNSC  LNPVLYAFLD  ENFKRCFREF  CIPTSSTIEQ
                                      Exon 10
N            71          81          91           1
361  QNSARIRQNT  REHPSTANTV  DRTNHQ APCA  CVPGANRGQT  KASDLLDLEL  ETVGSHQADA N            31          41          51          61          71
421  ETNPGPYEGS  KCAEPLAISL  VPLY
```

FIG. 3L

MOR-1

```
  1  mdssagpgni sdcsdplapa scspapgswl nlshvdgnqs dpcgpnrtgl ggshslcpqt
 61  gspsmvtait imalysivcv vglfgnflvm yvivrytkmk tatniyifnl aladalatst
121  lpfqsvnylm gtwpfgnilc kivisidyyn mftsiftlct msvdryiavc hpvkaldfrt
181  prnakivnvc nwilssaigl pvmfmattky rqgsidctlt fshptwywen llkicvfifa
241  fimpvliitv cyglmilrlk svrmlsgske kdrnlrritr mvlvvvavfi vcwtpihiyv
301  iikalitipe ttfqtvswhf cialgytnsc lnpvlyafld enfkrcfref ciptsstieq
361  qnsarirqnt rehpstantv drtnhqlenl eaetaplp
```

FIG. 3M

MOR-1 →
β₂MG →

FIG. 8B

FIG. 9A
FIG. 9B
FIG. 9C
FIG. 9D
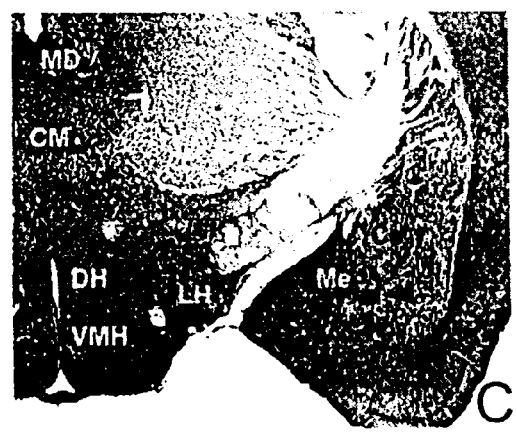
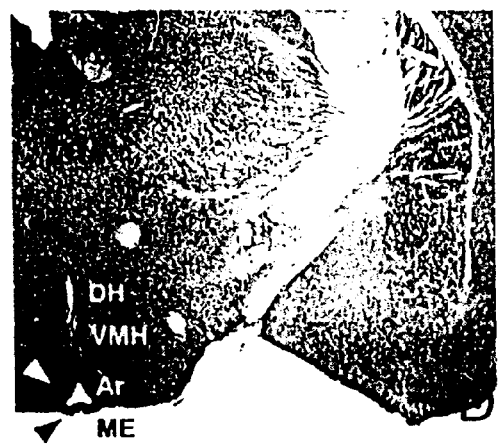

IDENTIFICATION AND CHARACTERIZATION OF MULTIPLE SPLICE VARIANTS OF THE MU-OPIOID RECEPTOR GENE

CROSS-REFERENCE TO RELATED APPLICATIONS

This application is a continuation-in-part of U.S. application Ser. No. 07/743,862, now abandoned, filed Jan. 16, 2001 under 35 U.S.C. § 371 as the U.S. national phase application of International Application PCT/US99/15974, having an international filing date of Jul. 15 1999, and designating the U.S. and claiming priority from U.S. Provisional Application No. 60/092,980, filed July 16 1998.

STATEMENT OF RIGHTS TO INVENTIONS MADE UNDER FEDERALLY SPONSORED RESEARCH

This work was supported by the government, in part, by grants from the National Institute on Drug Abuse (DA02615, DA06241 and DA07242) and a Senior Scientist Award (DA00220) to Gavril W. Pasternak and a core grant to Memorial Sloan-Kettering Cancer Center, New York, N.Y. (CA08748). The government may have certain rights to this invention.

TECHNICAL FIELD

The present invention relates to mu-opioid receptor-1 (MOR-1) splice variant polypeptides, to DNA sequences encoding the splice variants, to DNA sequences encompassing non-coding region splice variants, to methods of screening compositions for agonists and antagonists of the splice variant receptor activities and to methods of measuring splice variant binding activities.

BACKGROUND ART

Opiates are drugs derived from opium and include morphine, codeine and a wide variety of semisynthetic opioid congeners derived from them and from thebaine, another component of opium. Opioids include the opiates and all agonists and antagonists with morphine-like activity and naturally occurring endogenous and synthetic opioid peptides. Morphine and other morphine-like opioid agonists are commonly used pharmaceutically to produce analgesia.

There are now many compounds with pharmacological properties similar to those produced by morphine, but none has proven to be clinically superior in relieving pain. References to morphine herein will be understood to include morphine-like agonists as well. The effects of morphine on human beings are relatively diverse and include analgesia, drowsiness, changes in mood, respiratory depression, decreased gastrointestinal motility, nausea, vomiting, and alterations of the endocrine and autonomic nervous systems. Pasternak (1993) Clin. Neuropharmacol. 16:1. Doses of morphine need to be tailored based on individual sensitivity to the drug and the pain-sparing needs of the individual. For instance, the typical initial dose of morphine (10 mg/70 kg) relieves post-operative pain satisfactorily in only two-thirds of patients. Likewise, responses of an individual patient may vary dramatically with different morphine-like drugs and patients may have side effects with one such drug and not another. For example, it is known that some patients who are unable to tolerate morphine may have no problems with an equianalgesic dose of methadone. The mechanisms underlying variations in individual responses to morphine and morphine-like agonists have not been defined.

The analgesic effects of morphine are transduced through opioid receptors in the central nervous system (CNS), located at both spinal and multiple supraspinal sites. Morphine and other agonists induce profound analgesia when administered intrathecally or instilled locally into the dorsal horn of the spinal cord. Several mechanisms of action are believed to mediate the inhibition of nociceptive reflexes from reaching higher centers of the brain, including the inhibition of neurotransmitter release by opioid receptors on the termini of primary afferent nerves and post synaptic inhibitory actions on interneurons and on the out-put neurons of the spinothalamic tract.

Profound analgesia can also be produced by the instillation of morphine into the third ventricle or within various sites in the midbrain and medulla, most notably the periaqueductal gray matter, the nucleus raphe magnus, and the locus ceruleus. Although the neuronal circuitry responsible has not been defined, these actions produce enhanced activity in the descending aminergic bulbospinal pathways that exert inhibitory effects on the processing of nociceptive information in the spinal cord. Simultaneous administration of morphine at both spinal and supraspinal sites results in a synergized analgesic response, with a ten-fold reduction in the total dose of morphine necessary to produce equivalent analgesia at either site alone.

Morphine also exerts effects on the neuroendocrine system. Morphine acts in the hypothalamus to inhibit the release of gonadotropin releasing hormone (GnRH) and corticotropin-releasing factor (CRF), thus decreasing circulating concentrations of luteinizing hormone (LH), follicle stimulating hormone (FSH), and adrenocorticotropin (ACTH), and β-endorphin. As a result of the decreased concentrations of pituitary trophic hormones, the concentrations of testosterone and cortisol in the plasma decline. The administration of opiates increases the concentration of prolactin (PRL) in plasma, most likely by reducing the dopaminergic inhibition of PRL secretion. With chronic administration, tolerance eventually develops to the effects of morphine on hypothalamic releasing factors.

Opiates can interfere with normal gastrointestinal functioning. Morphine decreases both gastric motility and the secretion of hydrochloric acid in the stomach. Morphine may delay passage of gastric contents through the duodenum for as long as 12 hours. Morphine also decreases biliary, pancreatic, and intestinal secretions and delays the digestion of food in the small intestine. Propulsive peristaltic waves in the colon are diminished or abolished after administration of morphine and commonly, constipation occurs. For a detailed review of the physiological effects of morphine, see Reisine and Pasternak (1996) Goodman & Gilman's The pharmacological basis of therapeutics, Ninth Edition (Hardman et al. eds.) McGraw-Hill pp. 521–555.

Morphine also exerts effects on the immune system. The most firmly established effect of morphine is its ability to inhibit the formation of rosettes by human lymphocytes. The administration of morphine to animals causes suppression of the cytotoxic activity of natural killer cells and enhances the growth of implanted tumors. These effects appear to be mediated by actions within the CNS. By contrast, β-endorphin enhances the cytotoxic activity of human monocytes in vitro and increases the recruitment of precursor cells into the killer cell population; this peptide also can exert a potent chemotactic effect on these cells. A novel type of receptor (designated ε) may be involved. These effects, combined with the synthesis of Proopiomelanocortin (POMC) and preproenkephalin by various cells of the immune system, have stimulated studies of the potential role of opioids in the regulation of immune function. Sibinga and Goldstein (1988) Annu. Rev. Immunol. 6:219.

Side effects resulting from the use of morphine range from mild to life-threatening. Morphine causes constriction of the pupil by an excitatory action on the parasympathetic nerve innervating the pupil. Morphine depresses the cough reflex through inhibitory effects on the cough centers in the medulla. Nausea and vomiting occur in some individuals through direct stimulation of the chemoreceptor trigger zone for emesis, in the postrema of the medulla. Therapeutic doses of morphine also result in peripheral vasodilatation, reduced peripheral resistance and an inhibition of baroreceptor reflexes in the cardiovascular system. Additionally, morphine provokes the release of histamines, which can cause hypotension. Morphine depresses respiration, at least in part by direct effects on the brainstem regulatory systems. In humans, death from morphine poisoning is nearly always due to respiratory arrest. Opioid antagonists can produce a dramatic reversal of severe respiratory depression and naloxone is currently the treatment of choice. High doses of morphine and related opioids can produce convulsions that are not always relieved by naloxone.

The development of tolerance and physical dependence with repeated use is a characteristic feature of all opiates. Dependence seems to be closely related to tolerance, since treatments that block tolerance to morphine also block dependence. In vivo studies in animal models demonstrate the importance of neurotransmitters and their interactions with opioid pathways in the development of tolerance to morphine. Blockade of glutamate actions by noncompetitive and competitive NMDA (N-methyl-D-aspartate) antagonists blocks morphine tolerance. Trujillo and Akil (1991) Science 251:85; and Elliott et al. (1994) Pain 56:69. Blockade of the glycine regulatory site on NMDA receptors has similar effects to block tolerance. Kolesnikov et al. (1994) Life Sci. 55:1393. Administering inhibitors of nitric oxide synthase in morphine-tolerant animals reverses tolerance, despite continued opioid administration. Kolesnikov et al. (1993) Proc. Natl. Acad. Sci. U.S.A. 90:5162. These studies indicate several important aspects of tolerance and dependence. First, the selective actions of drugs on tolerance and dependence demonstrate that analgesia can be dissociated from these two unwanted actions. Second, the reversal of preexisting tolerance by NMDA antagonists and nitric oxide synthase inhibitors indicates that tolerance is a balance between activation of processes and reversal of those processes. These observations suggest that, by use of selective agonists and/or antagonists, tolerance and dependence in the clinical management of pain can be minimized or disassociated from the therapeutic effects.

In addition to morphine, there are a variety of opioids suitable for clinical use. These include, but are not limited to, Levorphanol, Meperidine, Fentanyl, Methadone, Codeine, Propoxyphene and various opioid peptides. Certain opioids are mixed agonists/antagonists and partial agonists. These include pentazocine, nalbuphine, butorphanol, and buprenorphine. The pharmacological effects of levorphanol closely parallel those of morphine although clinical reports suggest that levorphanol produces less nausea.

Meperidine exerts its chief pharmacological effects on the central nervous system and the neural elements in the bowel. Meperidine produces a pattern of effects similar but not identical to those described for morphine. In equianalgesic doses, meperidine produces as much sedation, respiratory depression, and euphoria as morphine. The pattern of unwanted side effects that follow the use of meperidine are similar to those observed after equianalgesic doses of morphine, except that constipation and urinary retention are less common.

Fentanyl is a synthetic opioid estimated to be 80 times as potent as morphine as an analgesic. High doses of fentanyl can result in severe toxicity and produce side effects including muscular rigidity and respiratory depression.

Methadone is an opioid with pharmacological properties similar to morphine. The properties of methadone include effective analgesic activity, efficacy by the oral route and persistent effects with repeated administration. Side effects include detection of miotic and respiratory-depressant effects for more than 24 hours after a single dose, and marked sedation is seen in some patients. Effects on cough, bowel motility, biliary tone and the secretion of pituitary hormones are qualitatively similar to those of morphine. In contrast to morphine, codeine is approximately 60% as effective orally as parenterally, both as an analgesic and as a respiratory depressant.

Codeine has an exceptionally low affinity for opioid receptors, and the analgesic effect of codeine is due to its conversion to morphine. However, codeine's antitussive actions probably involve distinct receptors that bind codeine specifically.

Propoxyphene produces analgesia and other CNS effects that are similar to those seen with morphine. It is likely that at equianalgesic doses the incidence of side effects such as nausea, anorexia, constipation, abdominal pain, and drowsiness would be similar to those of codeine.

Opioid antagonists have therapeutic utility in the treatment of overdosage with opioids. As understanding of the role of endogenous opioid systems in pathophysiological states increases, additional therapeutic indications for these antagonists will emerge. If endogenous opioid systems have not been activated, the pharmacological actions of opioid antagonists depend on whether or not an opioid agonist has been administered previously, the pharmacological profile of that opioid and the degree to which physical dependence on an opioid has developed. The antagonist naloxone produces no discernible subjective effects aside from slight drowsiness. Naltrexone functions similarly, but with higher oral efficacy and a longer duration of action. Currently, naloxone and naltrexone are used clinically to treat opioid overdoses. Their potential utility in the treatment of shock, stroke, spinal cord and brain trauma, and other disorders that may involve mobilization of endogenous opioids remains to be established.

The complex interactions of morphine and drugs with mixed agonist/antagonist properties are mediated by multiple classes of opioid receptors. Opioid receptors comprise a family of cell surface proteins, which control a range of biological responses, including pain perception, modulation of affective behavior and motor control, autonomic nervous system regulation and neuroendocrinological function. There are three major classes of opioid receptors in the CNS, designated mu, kappa and delta, which differ in their affinity for various opioid ligands and in their cellular distribution. The different classes of opioid receptors are believed to serve different physiologic functions. Olson et al. (1989) Peptides 10:1253; Lutz and Pfister (1992) J. Receptor Res. 12:267; and Simon (1991) Medicinal Res. Rev. 11:357. Morphine produces analgesia primarily through the mu-opioid receptor. However, among the opioid receptors, there is substantial overlap of function as well as of cellular distribution.

The mu-opioid receptor mediates the actions of morphine and morphine-like opioids, including most clinical analgesics. In addition to morphine, several highly selective agonists have been developed for mu-opioid receptors, including [D-Ala$^2$, MePhe$^4$, Gly(ol)$^5$]enkephalin (DAMGO), levorphanol and methadone. Differential sensitivity to antagonists, such as naloxonazine, indicates the pharmacological distinctions between the mu-opioid receptor subtypes, mu$_1$ and mu$_2$. Several of the opioid peptides will also interact with mu-opioid receptors.

There are three distinct families of endogenous opioid peptides, the enkephalins, endorphins and dynorphins, where each peptide is derived from a distinct precursor polypeptide. Mu-opioid receptors have a high affinity for the enkephalins as well as β-endorphin and dynorphin A. For review, see Reisine and Pasternak (1996).

Members of each known class of opioid receptor have been cloned from human cDNA and their predicted amino acid sequences have been determined. Yasuda et al. (1993) Proc. Natl. Acad. Sci. U.S.A. 90:6736; and Chen et al. (1993) Mol. Pharmacol. 44:8. The opioid receptors belong to a class of transmembrane spanning receptors known as G-protein coupled receptors. G-proteins consist of three tightly associated subunits, alpha, beta and gamma (1:1:1) in order of decreasing mass. Following agonist binding to the receptor, a conformational change is transmitted to the G-protein, which causes the G-alpha subunit to exchange a bound GDP for GTP and to dissociate from the beta and gamma subunits. The GTP-bound form of the alpha subunit is typically the effector-modulating moiety. Signal amplification results from the ability of a single receptor to activate many G-protein molecules, and from the stimulation by G-alpha-GTP of many catalytic cycles of the effector.

Most opioid receptor-mediated functions appear to be mediated through G-protein interactions. Standifer and Pasternak (1997) Cell Signal. 9:237. Antisense oligodeoxynucleotides directed against various G-protein alpha subunits were shown to differentially block the analgesic actions of the mu-, delta-, and kappa-opioid agonists in mice. Standifer et al. (1996) Mol. Pharmacol. 50:293.

The amino acid sequences of the opioid receptors are approximately 65% identical, and they have little sequence similarity to other G-protein-coupled receptors except for somatostatin. Reisine and Bell (1993) Trends Neurosci. 16:506. The regions of highest similarity in sequence are the sequences predicted to lie in the seven transmembrane-spanning regions and the intracellular loops. Regions of amino acid sequence divergence are the amino and carboxy termini and the second and third extracellular loops.

Each receptor subtype has a characteristic pattern of expression. Mu-opioid receptor mRNA is present in the periaqueductal gray, spinal trigeminal nucleus, cuneate and gracile nuclei, and thalamus regions of the brain involved in pain perception and associated with morphine analgesia (Defts et al. (1994) J. Comp. Neurol. 345:46); in nuclei involved in control of respiration, consistent with the ability of morphine to depress respiration; and in neurons of the area postrema, where morphine has been shown to cause nausea and induce vomiting. Other consequences of mu-opioid receptor activation include miosis, reduced gastrointestinal motility, and feelings of well-being or euphoria. Pasternak (1993). The pattern of mu-opioid receptor mRNA expression correlates with the brain centers involved in mediating the biological actions of morphine and mu-selective agonists. Delta-opioid receptor mRNA is found in the dorsal horn of the spinal cord. Kappa$_1$-opioid receptor mRNA is expressed in the hypothalamic regions, which may account for many of the neuroendocrine effects of the kappa selective agonists.

Soon after the mu-opioid receptor MOR-1 was cloned (Chen et al. (1993); and Wang et al. (1993) Proc. Natl. Acad. Sci. U.S.A. 90:10230), antisense experiments confirmed its involvement with morphine analgesia. Rossi et al. (1994) Life Sci. 54:375; and Rossi et al. (1995) FEBS Lett. 369:192. Antisense oligonucleotides directed against MOR-1 mRNA blocked the analgesic actions of morphine in rats, demonstrating that proper translation of the MOR-1 mRNA was essential for modulating morphine analgesia. Antisense approaches have also demonstrated a relationship between MOR-1 activity and ingestive responses. Administration of antisense oligonucleotides directed against MOR-1 mRNA significantly reduced food and water intake and subsequently, body weight in rats.

In recent years, a number of mu-opioid receptor subtypes have been proposed. The first suggestion of mu$_1$ and mu$_2$ receptor subtypes came from a combination of binding and pharmacological studies based on the antagonists naloxonazine and naloxazone. Wolozin and Pasternak (1981) Proc. Natl. Acad. Sci. U.S.A. 78:6181; Reisine and Pasternak (1996); and Pasternak (1993). To date, only a single mu receptor gene, MOR-1, has been identified. Min et al. (1994) Proc. Natl. Acad. Sci. U.S.A. 91:9081; Giros et al. (1995) Life Sci. 56:PL369; and Liang et al. (1995) Brain Res. 679:82. The MOR-1 cDNA consists of exons 1–4, which total 1610 bp in length and encode 398 amino acids. More recently, pharmacological and molecular differences between morphine and morphine-6β-glucuronide (M6G) have suggested yet another mu-opioid receptor subtype. Pasternak and Standifer (1995) Trends Pharmacol. Sci. 16:344; Rossi et al. (1995); and Rossi et al. (1996) Neurosci. Lett. 216:1.

Antisense oligonucleotides directed against selected exons within the MOR-1 mRNA revealed interesting therapeutic patterns of morphine and M6G analgesia, with some MOR-1 exons implicated in the analgesic actions of one drug, but not the other. Rossi et al. (1997) J. Pharmacol. Exp. Ther. 281:109; and Rossi et al. (1995). Although the two analgesics were known to act through different receptors, the sensitivity of the effect of both analgesics to at least six different MOR-1 antisense probes implied that both receptors were closely associated with MOR-1, raising the possibility of pharmacologically relevant MOR-1 splice variants. Pasternak and Standifer (1995); and Rossi et al. (1995). Alternative splicing has been observed with a number of G-protein-coupled receptors, including somatostatin 2 (Vanetti et al. (1998) FEBS Lett. 311:290), dopamine D2 (Guiramand et al. (1995) J. Biol. Chem. 270:7354), prostaglandin EP3 (Namba et al. (1993) Trends Pharmacol. Sci. 16:246), serotonin receptor subtypes 5-HT$_4$ and 5-HT$_7$ (Lucas and Hen. (1995) Trends Pharmacol. Sci. 16:246) and MOR-1. Bare et al. (1994) FEBS Lett. 354:213; and Zimprich et al. (1995) FEBS Lett. 359:142.

Several opioid receptor splice variants have been identified and characterized. At least two MOR-1 splice variants are known, the human MOR-1A and the rat MOR-1B$_s$. Bare et al. (1994); and Zimprich et al. (1995). The hMOR-1A splice variant consists of exons 1, 2, 3 and a new exon 3a, and was determined to possess ligand binding characteristics similar to the full-length MOR-1. Bare et al. (1994). The rMOR-1B$_s$ splice variant consists of exons 1, 2, 3 and a new exon 5, and like hMOR-1A, differs from MOR-1 only in length and amino acid composition at the carboxy-terminal tail. Zimprich et al. (1995). MOR-1B$_s$ has affinity to opioid compounds similar to that of MOR-1, but is much more resistant to agonist-induced desensitization than MOR-1. The C-terminal differences between MOR-1 and MOR-1A or MOR-1B$_s$ could have effects on receptor coupling or receptor transport and localization. The MOR-1 splice variants are potential targets for the modulation of physiological effects resulting from mu-opioid receptor activity.

Availability of polynucleotide sequences of opioid receptor splice variants, and, in the case of splice variants in coding regions, the corresponding polypeptide sequences, will significantly increase the capability to design pharmaceutical compositions, such as analgesics, with enhanced specificity of function. In general, the availability of these polynucleotide and polypeptide sequences will enable efficient screening of candidate compositions. The principle in operation through the screening process is straightforward: natural agonists and antagonists bind to cell-surface receptors and channels to produce physiological effects; certain other molecules can produce physiological effects and act as therapeutic pharmaceutical agents. Thus, the ability of candidate drugs to bind to opioid receptor splice variants can function as an extremely effective screening criterion for the selection of pharmaceutical compositions with desired functional efficacy and specificity.

DISCLOSURE OF THE INVENTION

The invention encompasses MOR-1 splice variant polypeptides or polypeptide fragments or homologs thereof retaining MOR-1 activity.

The invention further encompasses a MOR-1 splice variant polynucleotide, encoding MOR-1 splice variant polypeptides or polypeptide fragments or homologs thereof retaining MOR-1 activity, and noncoding mRNA splice variants and complementary strands thereto.

The invention further encompasses a polynucleotide, or a complementary strand thereto that hybridizes under stringent conditions, comprising at least 15 consecutive nucleotides of an MOR-1 splice variant polynucleotide where the polynucleotide contains promoter elements.

The invention further encompasses methods of screening compositions for an opioid activity by obtaining a control cell that does not express a recombinant or endogenous opioid receptor, obtaining a test cell that expresses a recombinant MOR-1 splice variant polypeptide, contacting the control cell and test cell with an amount of an opioid sufficient to exert a physiologic effect, separately measuring the physiologic effect of the composition on the control cell and test cell and comparing the physiologic effect of the composition to the physiologic effect of the opioid, where determination of a physiologic effect of the composition is expressed relative to that of the opioid.

The invention further encompasses methods of screening compositions for an opioid activity by obtaining a control polypeptide that is not a recombinant opioid receptor, obtaining a test polypeptide that is a recombinant MOR-1 splice variant polypeptide, contacting a composition with the control polypeptide and the test polypeptide, contacting the test polypeptide with an amount of an opioid sufficient to measurably bind the test polypeptide, measuring the binding of the composition and the opioid, and comparing the test polypeptide binding of the composition to that of the opioid, where determination of binding of the composition is expressed relative to that of the opioid.

The invention further encompasses methods of screening compositions for differential or selective opioid activity comprising obtaining a first and second test polypeptide that are MOR-1 splice variant polypeptide fragments and contacting each with a composition, measuring the binding affinity of the composition to the first and second test polypeptides and comparing the binding of the composition and the first test polypeptide to that of the second test polypeptide where differential activity is expressed as a ratio of the two binding affinities.

The invention further encompasses a non-human animal in which one or both endogenous MOR-1 alleles has been altered by homologous recombination with an exogenously introduced MOR-1 splice variant polynucleotide.

The invention further encompasses a non-human transgenic animal carrying a transgene comprising an MOR-1 splice variant polynucleotide.

The invention further encompasses a method for regulating morphine analgesia in a subject by altering the amount of MOR-1 splice variant polypeptide activity. Activity can be regulated by administering antigen binding fragments, agonists, antagonists or small molecule ligands to a subject in an amount and a duration sufficient to regulate morphine analgesia. The antigen binding fragment, agonist, antagonist or small molecule ligand is directed to an MOR-1 splice variant polypeptide fragment or MOR-1 splice variant mRNA.

The invention further encompasses regulating opioid activity by administering a DNA plasmid vector containing an MOR-1 splice variant polynucleotide. The DNA plasmid vector thereby expresses an mRNA splice variant that may encode an MOR-1 polypeptide in a subject in an amount of and a duration sufficient to regulate morphine analgesia. Activity can also be regulated by administering an antisense nucleic acid complementary to an MOR-1 splice variant polynucleotide, thereby blocking gene expression in a subject in an amount and a duration sufficient to regulate morphine analgesia.

The invention further encompasses a method for regulating body weight in a subject by altering the amount of MOR-1 splice variant polypeptide activity in the subject. Activity can be regulated by administering antigen binding fragments, agonists, antagonists or small molecule ligands to a subject in an amount and a duration sufficient to regulate body weight. The antigen binding fragment, agonist, antagonist or small molecule ligand is directed to an MOR-1 splice variant polypeptide.

Activity can also be regulated by administering to the subject a DNA plasmid vector containing an MOR-1 splice variant polynucleotide. The DNA plasmid vector thereby expresses an MOR-1 polypeptide fragment or MOR-1 splice variant mRNA in the subject in an amount of and a duration sufficient to regulate body weight of the subject. Activity can also be regulated by administering an antisense nucleic acid complementary to an MOR-1 splice variant polynucleotide, thereby blocking gene expression in a subject in an amount and a duration sufficient to regulate body weight of the subject.

The invention further encompasses a method for diagnosing an MOR-1 splice variant-associated pharmacological abnormality, comprising measuring the amount of variant activity or tissue distribution thereof in a subject and comparing that activity or tissue distribution to a control sample, wherein a difference in the amount of activity or tissue distribution correlates with the presence of a pharmacologic defect.

The invention further encompasses a method for diagnosing an MOR-1 splice variant-associated disorder, comprising measuring the amount of variant activity or tissue distribution thereof in a subject and comparing that activity or tissue distribution to a control sample, wherein a difference in the amount of activity or tissue distribution correlates with the presence of a disorder of the neuroendocrine system.

The invention further encompasses antigen-binding fragments specific for the MOR-1 splice variant polypeptides described herein.

BRIEF DESCRIPTION OF THE DRAWINGS

FIGS. 2A–2V depict the MOR-1 splice variant polynucleotides. These include: MOR-1a; MOR-1bI; MOR-1g; MOR-1h; MOR-1c; MOR-1d; MOR-1e; MOR-1j; MOR-1i; MOR-1bII; MOR-1f; hMOR-1-610302; and clones 3320510, 2730510, and 161416.

FIGS. 3A–3M depict the MOR-1 splice variant polypeptides. These include: MOR-1C; MOR-1G; MOR-1D; MOR-1E; MOR-1H; MOR-1I; MOR-1J; hMOR-1-610302; MOR-1A; MOR-1BI; MOR-1BII; MOR-1F; and MOR-1. FIG. 3 also designates exons where applicable.

In FIG. 4, the small solid triangles represent casein kinase phosphorylation sites and the large open triangle represents a protein kinase C phosphorylation site.

FIGS. 8A and 8B depict regional distribution of the MOR-1c, MOR-1d and MOR-1e mRNA. In 8A, RT-PCR was performed on the indicated brain regions using the indicated probes. In 8B, RT-PCR was performed on the indicated brain regions using the indicated probe.

FIGS. 9A–9D depict immunohistochemical localization of MOR-1 and MOR-1C in mouse brain. Sections A and B and Sections C and D were stained with MOR-1 and MOR-1C antisera respectively. Regions were (A and B) St, striatum; ac, anteriorcommissure; Ac, accumbens; and LS, lateral septum; (c) MD, mediodorsal thalamic nucleus; CM, centromedian thalamic nucleus; DH, dorsal hypothalamic nucleus; LH, lateral hypothalamic nucleus; Ce, central amygdaloid nucleus; Ic, intercalated amygdaloid nucleus; and Me, medial amygdaloid nucleus; and (D) Ar, arcuate nucleus; and ME, median eminence.

Figure 1:
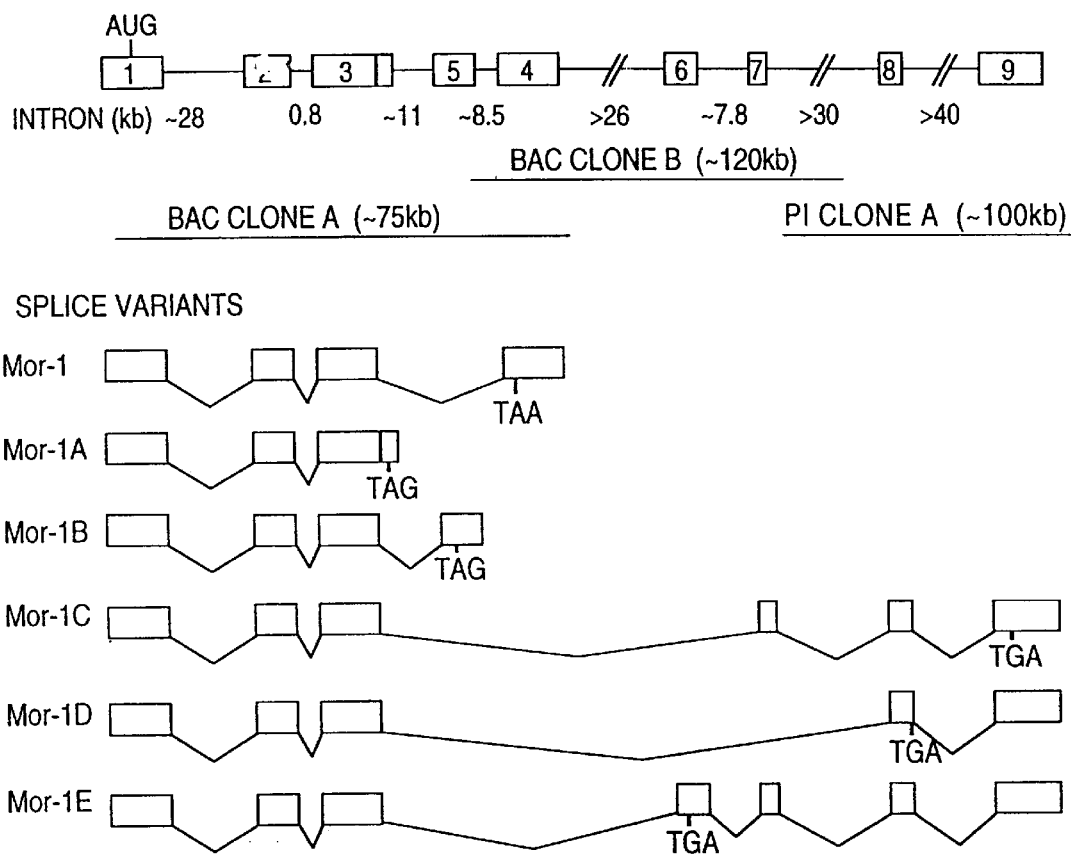
FIG. 1 depicts a schematic diagram of MOR-1 gene structure and alternative splicing. Exons and introns are indicated by boxes and horizontal lines, respectively. The translational start codon and termination codon are AUG and TAA or TAG or TGA. Overlapping genomic clones covering the entire MOR-1 gene are shown by heavy horizontal lines on the top panel.
Figure 4:
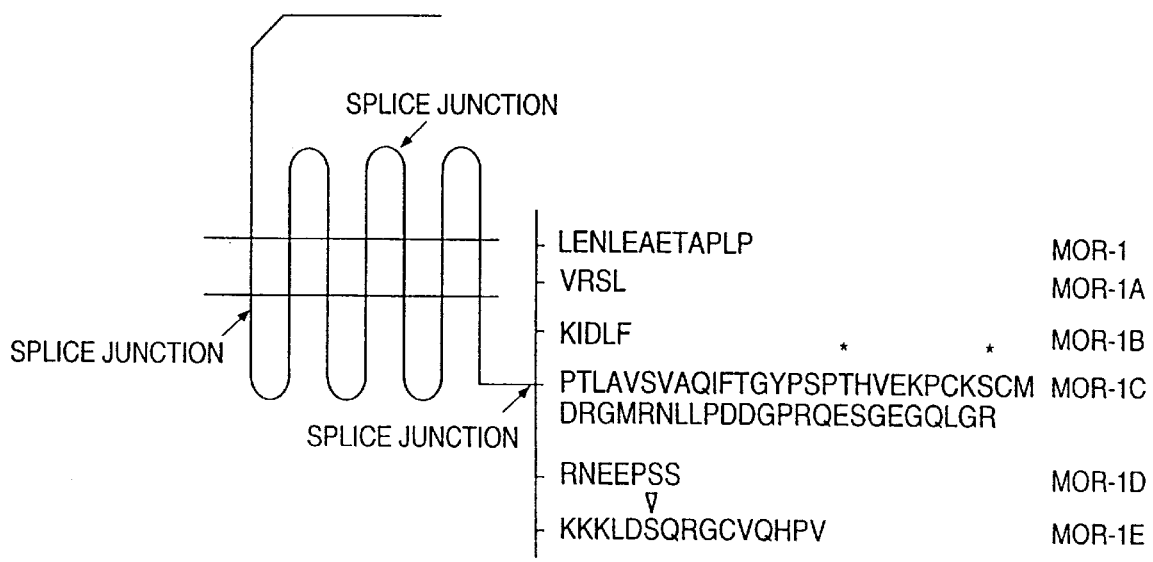
FIG. 4 compares the amino acid sequences of several MOR-1 splice variant polypeptides predicted from the cDNA clones. All are murine variants except MOR-1a and MOR-1b which are human and rat, respectively.

SEQ ID NOS: are assigned to the sequences as described below:

SEQ ID NO: 1 refers to the nucleotide sequence of MOR-1c

SEQ ID NO: 2 refers to the nucleotide sequence of MOR-1g

SEQ ID NO: 3 refers to the nucleotide sequence of MOR-1d

SEQ ID NO: 4 refers to the nucleotide sequence of MOR-1e

SEQ ID NO: 5 refers to the nucleotide sequence of MOR-1h

SEQ ID NO: 6 refers to the nucleotide sequence of clone 3320510

SEQ ID NO: 7 refers to the nucleotide sequence of clone 161416

SEQ ID NO: 8 refers to the nucleotide sequence of clone 2730510

SEQ ID NO: 9 refers to the nucleotide sequence of MOR-1f

SEQ ID NO: 10 refers to the nucleotide sequence of MOR-1bII

SEQ ID NO: 11 refers to the nucleotide sequence of MOR-1a

SEQ ID NO: 12 refers to the nucleotide sequence of MOR-1bI

SEQ ID NO: 13 refers to the nucleotide sequence of MOR-1i

SEQ ID NO: 14 refers to the nucleotide sequence of MOR-1j

SEQ ID NO: 15 refers to the nucleotide sequence of hMOR-1-61032

SEQ ID NO: 16 refers to the nucleotide sequence of MOR-1

SEQ ID NO: 17 refers to the amino acid sequence of MOR-1C

SEQ ID NO: 18 refers to the amino acid sequence of MOR-1G

SEQ ID NO: 19 refers to the amino acid sequence of MOR-1D

SEQ ID NO: 20 refers to the amino acid sequence of MOR-1E

SEQ ID NO: 21 refers to the amino acid sequence of MOR-1H

SEQ ID NO: 22 refers to the amino acid sequence of MOR-1I

SEQ ID NO: 23 refers to the amino acid sequence of MOR-1J

SEQ ID NO: 24 refers to the amino acid sequence of hMOR-1-610302

SEQ ID NO: 25 refers to the amino acid sequence of MOR-1A

SEQ ID NO: 26 refers to the amino acid sequence of MOR-1BI

SEQ ID NO: 27 refers to the amino acid sequence of MOR-1BII

SEQ ID NO: 28 refers to the amino acid sequence of MOR-1F

SEQ ID NO: 29 refers to the amino acid sequence of MOR-1

SEQ ID NO: 30 refers to the splice variant polypeptide sequence of MOR-1

SEQ ID NO: 31 refers to the splice variant polypeptide sequence of MOR-1A

SEQ ID NO: 32 refers to the splice variant polypeptide sequence of MOR-1B

SEQ ID NO: 33 refers to the splice variant polypeptide sequence of MOR-1C

SEQ ID NO: 34 refers to the splice variant polypeptide sequence of MOR-1D

SEQ ID NO: 35 refers to the splice variant polypeptide sequence of MOR-1E

SEQ ID NO: 36 refers to the sequence of the basic unit of linking peptide (GGGGS)$_3$ SEQ ID NO: 37 refers to the antisense primer sequence corresponding to the 3' UTR of MOR-1, (5'CCACACTGCTCACCAGCTCATCCC3')

SEQ ID NO: 38 refers to the antisense primer derived from exon 7 of the mouse MOR-1 gene (5'TGTCCATGCAACTCTTGCAGGGTTTTTCAACATGAGTCGGAGAAGGAT3')

SEQ ID NO: 39 refers to the sense primer designed from exon 3 (5'GGGAACACCCCTCCACGG3')

SEQ ID NO: 40 refers to the antisense primer from exon 5a (5'GGTGTGCTTCTCCCAGTTCTGTGT3')

SEQ ID NO: 41 refers to the sense primer designed from exon 1a (5'CCTCCAGGCTCATTTCAGAGAGA3')

SEQ ID NO: 42 refers to the antisense primer from exon 1 (5'CAGGAAGTTTCCAAAGAGGCCC3')

SEQ ID NO: 43 refers to the antisense primer from exon 2 (5'GGGCAGGTGGTAGTGGCTAAGGC3')

SEQ ID NO: 44 refers to the polypeptide sequence (KIDLE)

SEQ ID NO: 45 refers to the amino acid sequence (KLLMWRAMPTFKRHLAIMLSLDN)

SEQ ID NO: 46 refers to the sequence of the antisense primer corresponding to the 3' UTR of exon 3a (5'GATCAGAATTTGGTGCCCTACTCCCTCTCT3').

BEST MODE FOR CARRYING OUT THE INVENTION

In view of the strong pharmacological evidence for distinct mu-opioid receptors, alternative splicing of the MOR-1 gene has been explored further. It has now been determined that the MOR-1 gene is subject to alternative splicing that produces novel splice variant forms of the mRNA and/or receptor. Eleven new exons for the MOR-1 gene have been identified, which combine to yield fifteen novel MOR-1 splice variant polynucleotides. These splice variant polynucleotides and the polypeptides encoded thereby are potential targets for modulating morphine analgesia and opioid-mediated ingestive responses.

The invention further encompasses isolated MOR-1 splice variant polynucleotide sequences indicated in FIG. 2. In addition to FIG. 2, the polynucleotide sequences can be any sequence of the appropriate genetic code to encode any of the MOR-1 splice variant polypeptides indicated in FIG. 3. Preferably, the polynucleotide is at least 15 consecutive nucleotides.

A "polynucleotide" is a polymeric form of nucleotides of any length, which contain deoxyribonucleotides, ribonucleotides, and analogs in any combination. Polynucleotides may have three-dimensional structure, and may perform any function, known or unknown. The term "polynucleotide" includes double-, single-stranded, and triple-helical molecules. Unless otherwise specified or required, any embodiment of the invention described herein that is a polynucleotide encompasses both the double stranded form and each of two complementary forms known or predicted to make up the double stranded form of either the DNA, RNA or hybrid molecule.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support.

An "isolated" polynucleotide or polypeptide is one that is substantially free of the materials with which it is associated in its native environment. By substantially free, is meant at least 50%, preferably at least 70%, more preferably at least 80%, and even more preferably at least 90% free of these materials.

The invention further comprises a complementary strand to the MOR-1 splice variant polynucleotide.

The complementary strand can be polymeric and of any length, and can contain deoxyribonucleotides, ribonucleotides, and analogs in any combination.

Hybridization reactions can be performed under conditions of different "stringency." Conditions that increase stringency of a hybridization reaction are well known. See for examples, "Molecular Cloning: A Laboratory Manual", second edition (Sambrook et al. 1989). Examples of relevant conditions include (in order of increasing stringency): incubation temperatures of 25° C., 37° C., 50° C., and 68° C.; buffer concentrations of 10×SSC, 6×SSC, 1×SSC, 0.1×SSC (where SSC is 0.15 M NaCl and 15 mM citrate buffer) and their equivalent using other buffer systems; formamide concentrations of 0%, 25%, 50%, and 75%; incubation times from 5 minutes to 24 hours; 1, 2 or more washing steps; wash incubation times of 1, 2, or 15 minutes; and wash solutions of 6×SSC, 1×SSC, 0.1×SSC, or deionized water.

The invention further encompasses polynucleotides encoding functionally equivalent variants and derivatives of the MOR-1 splice variant polypeptides and functionally equivalent fragments thereof which may enhance, decrease or not significantly affect properties of the polypeptides encoded thereby. These functionally equivalent variants, derivatives, and fragments display the ability to retain MOR-1 activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan.

The invention further encompasses the MOR-1 splice variant polynucleotides contained in a vector molecule or an expression vector and operably linked to a promoter element if necessary.

A "vector" refers to a recombinant DNA or RNA plasmid or virus that comprises a heterologous polynucleotide to be delivered to a target cell, either in vitro or in vivo. The heterologous polynucleotide may comprise a sequence of interest for purposes of therapy, and may optionally be in the form of an expression cassette. As used herein, a vector need not be capable of replication in the ultimate target cell or subject. The term includes cloning vectors for translation of a polynucleotide encoding sequence. Also included are viral vectors.

The term "recombinant" means a polynucleotide of genomic cDNA, semisynthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide, may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The polynucleotides of the invention may comprise additional sequences, such as additional encoding sequences within the same transcription unit, controlling elements such as promoters, ribosome binding sites, polyadenylation sites, additional transcription units under control of the same or a different promoter, sequences that permit cloning, expression, homologous recombination, and transformation of a host cell, and any such construct as may be desirable to provide embodiments of this invention.

A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell, and to the progeny thereof.

Polynucleotides comprising a desired sequence can be inserted into a suitable cloning or expression vector, and the vector in turn can be introduced into a suitable host cell for replication and amplification. Polynucleotides can be introduced into host cells by any means known in the art. The vectors containing the polynucleotides of interest can be introduced into the host cell by any of a number of appropriate means, including direct uptake, endocytosis, transfection, f-mating, electroporation, transfection employing calcium chloride, rubidium chloride, calcium phosphate, DEAE-dextran, or other substances; microprojectile bombardment; lipofection; and infection (where the vector is infectious, for instance, a retroviral vector). The choice of introducing vectors or polynucleotides will often depend on features of the host cell.

Once introduced, the exogenous polynucleotide can be maintained within the cell as a non-integrated vector (such as a plasmid) or integrated into the host cell genome. Amplified DNA can be isolated from the host cell by standard methods. See, e.g., Sambrook et al. (1989). RNA can also be obtained from transformed host cell, or it can be obtained directly from the DNA by using a DNA-dependent RNA polymerase.

Expression vectors generally are replicable polynucleotide constructs that contain a polynucleotide encoding the polypeptide of interest. Herein, this means any of the MOR-1 splice variant polypeptides. For expression, one or more translational controlling elements are also usually required, such as ribosome binding sites, translation initiation sites and stop codons. These controlling elements (transcriptional and translational) can be derived from the MOR-1 gene, or heterologous (i.e., derived from other genes or other organisms). A number of expression vectors suitable for expression in eukaryotic cells including yeast, avian, and mammalian cells are well known in the art. One example of an expression vector is pcDNA3 (Invitrogen, San Diego, Calif.), in which transcription is driven by the cytomegalovirus (CMV) early promoter/enhancer. This vector also contains recognition sites for multiple restriction enzymes for insertion of an MOR-1 splice variant polypeptide of interest. Another example of an expression vector system is the baculovirus/insect system.

Cloning and expression vectors typically contain a selectable marker (for example, a gene encoding a protein necessary for the survival or growth of a host cell transformed with the vector), although such a marker gene can be carried on another polynucleotide sequence co-introduced into the host cell. Only those host cells into which a selectable gene has been introduced will grow under selective conditions. Typical selection genes either: (a) confer resistance to antibiotics or other toxins, e.g., ampicillin, neomycin, methotrexate; (b) complement auxotrophic deficiencies; or (c) supply critical nutrients not available for complex media. The choice of the proper marker gene will depend on the host cell, and appropriate genes for different hosts are known in the art. Vectors also typically contain a replication system recognized by the host.

Suitable cloning vectors can be constructed according to standard techniques, or selected from a large number of cloning vectors available in the art. While the cloning vector selected may vary according to the host cell intended to be used, useful cloning vectors will generally have the ability to self-replicate, may possess a single target for a particular restriction endonuclease, or may carry marker genes. Suitable examples include plasmids and bacterial viruses, e.g., pUC18, mp18, mp19, pBR322, pMB9, ColE1, pCR1, RP4, phage DNAs, and shuttle vectors such as pSA3 and pAT28. These and other cloning vectors are available from commercial vendors such as BioRad, Stratagene, and Invitrogen.

The invention further encompasses an isolated polynucleotide, or a complementary strand thereto that hybridizes under stringent conditions, comprising at least 15 consecutive nucleotides of the MOR-1 splice variant polynucleotides depicted in (FIG. 2) where the polynucleotide contains promoter elements.

The MOR-1 splice variant promoter elements, are contained in exons 1a, 1b, and 1c or in any combination thereof. Promoter elements can control the level, tissue specificity, inducibility and, in gene clusters, the sequence of transcriptional activation and repression. Promoter elements include but are not limited to, enhancer sequences and repressor sequences.

The invention further encompasses non-human animals in which one or both MOR-1 alleles has been altered by homologous recombination with an exogenously introduced nucleic acid.

Non-human animals devoid of one or more gene products are generated to determine the "loss-of-function" phenotype associated with the loss of that particular gene product. Herein, the gene product is the MOR-1 gene or splice variants thereof. Phenotypic abnormalities can be present, for instance, in anatomical structures, biochemical and genetic pathways and pharmacological responses. Loss-of-function phenotypic analysis has the potential to reveal the function of the gene product.

Methods of homologous recombination with an exogenously introduced nucleic acid are used to inactivate one or more alleles in non-human animals. These methods, as applied to mice and rats, are well known in the art. Capecchi (1989) Science 244:1288. Usually, an exogenous polynucleotide encoding a selectable marker gene, and having sufficient sequence homology to the targeted site of integration at either end of the polynucleotide, is introduced into the genome of embryonic stem cells (ES cells) derived from the inner cell mass of non-human animal blastocysts. Evans and Kaufman (1981) Nature 292:154. Through homologous recombination, the polynucleotide is incorporated into the genetic locus at the targeted site of integration, replacing the corresponding sequences of the endogenous allele. ES cells are used to generate chimeric animals either by microinjection into, or aggregation with wildtype embryos. Chimeric animals having germ line transmission of the inactivated allele are bred to produce heterozygous, and subsequently, homozygous lines carrying the inactivated allele. Robertson (1991) Biol. Reprod. 44:238.

The invention further encompasses non-human transgenic animals carrying a transgenic MOR-1 splice variant polynucleotide.

Non-human animals carrying additional copies of the gene of interest are generated to determine the "gain-of-function" phenotype associated with an excess of that particular gene product. Herein, the gene product is any of the MOR-1 splice variant polynucleotides. Phenotypic abnormalities can be present, for instance, in anatomical structures, biochemical and genetic pathways and pharmacological responses. Gain-of-function phenotypic analysis has the potential to reveal the function of the gene product.

Methods of generating transgenic animals are well known in the art. Jaenisch (1988) Science 240:1468. "Transgenes" are exogenous polynucleotides encoding the gene of interest. Transgenes are introduced into the embryonic genome through microinjection. Alternatively, a transgene encoding the gene of interest and a selectable marker gene is introduced into the ES cell genome through transfection or electroporation. ES cells carrying the transgene are subsequently used to produce animals with multiple copies of the gene of interest.

The invention encompasses splice variant polypeptides. The exemplary MOR-1 splice variant polypeptides are composed of the amino acids indicated in (FIG. 3). Polypeptide fragments comprising 5 amino acids, more preferably 7 amino acids, more preferably 15 amino acids, more preferably 25 amino acids, more preferably 50 amino acids and more preferably 75 amino acids, which are not the same as the known MOR-1 or MOR-1 variants are claimed herein and encompassed in the term "MOR-1 splice variant polypeptides." The exemplary MOR-1 splice variant polypeptide fragments retain MOR-1 activity. The complete cDNA sequences of MOR-1C, MOR-1D, and MOR-1E have been deposited in GenBank, numbers AF062752, AF062753, and AF074974 respectively, in satisfaction of the requirements of the Budapest Treaty.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

The MOR-1 splice variant polypeptides retain MOR-1 activity. To "retain MOR-1 activity" is to have a similar level of functional activity as the MOR-1 polypeptide (FIG. 3). This activity includes but is not limited to, immunologic and pharmacological activity.

The "immunologic activity" is binding to anti-opioid receptor antigen binding fragments. The antigen binding fragments can be any functional antibody, fragment or derivative thereof, including, but not limited to, whole native antibodies, bispecific antibodies, chimeric antibodies, Fab, F(ab')2, single chain V region fragments (scFv), and fusion polypeptides comprising an antigen binding fragment fused to a chemically functional moiety.

The "pharmacologic activity" is activation or deactivation of the MOR-1 splice variant polypeptides upon binding of agonists or antagonists.

The invention further encompasses MOR-1 splice variant polypeptide homologs. A "homolog" is a polypeptide similar in amino acid sequence to other polypeptides among a single species or, a "homolog" in evolution is a polypeptide similar in amino acid sequence to other polypeptides in different species because they have been inherited from a common ancestor. Preferably, homologs of the present invention are human homologs.

Isolation of MOR-1 splice variant human homolog cDNAs can be carried out by any method known in the art. For instance, methods analogous to the isolation of the mouse MOR-1 splice variants described herein (see Example 1). Using primers corresponding to the human MOR-1 gene and a Marathon-Ready human cDNA Library to carry out reactions according to the Marathon cDNA Amplification Kit (Clontech), human MOR-1 splice variants can be obtained. Alternatively, screening of human cDNA libraries with probes corresponding to mouse MOR-1 splice variant sequences can be carried out at reduced stringency to identify human MOR-1 splice variant cDNAs.

The invention further encompasses the MOR-1 splice variant polypeptides in a heterodimeric or homodimeric form. A "heterodimer" is a protein made up of more than one kind of polypeptide. A "homodimer" is a protein made up of more than one kind of polypeptide.

Pharmaceutical compositions and treatment modalities can be detected by the methods of this invention. The MOR-1 splice variant polypeptide fragments and MOR-1 splice variant nucleic acid sequences can be used in screening for compositions that alter variant activity. Compositions that selectively regulate the MOR-1 splice variant polypeptide fragments or selectively modulate physiological processes can be identified.

The invention further encompasses methods of screening compositions for opioid activity by obtaining a control cell that does not express a recombinant opioid receptor and obtaining a test cell that is the same as the control cell except that it expresses a recombinant MOR-1 splice variant polypeptide, contacting the control cell and test cell with an amount of an opioid sufficient to exert a physiologic effect, separately measuring the physiologic effect of the composition on the control cell and test cell and comparing the physiologic effect of the composition to the physiologic effect of the opioid, where determination of a physiologic effect of the composition is expressed relative to that of the opioid.

The invention further comprises a method of screening compositions for opioid activity by obtaining a control polypeptide that is not a recombinant opioid receptor and obtaining a test polypeptide that is a recombinant MOR-1 splice variant polypeptide, contacting a composition with the control polypeptide and the test polypeptide, contacting the test polypeptide with an amount of an opioid sufficient to measurably bind the test polypeptide, measuring the binding of the composition and the opioid and comparing the test polypeptide binding of the composition to that of the opioid, where determination of binding of the composition is expressed relative to that of the opioid.

The invention further encompasses a method of screening compositions for differential opioid activity by obtaining a first test polypeptide that is an MOR-1 splice variant polypeptide and contacting it with a composition and obtaining a second test polypeptide that is an MOR-1 splice variant polypeptide, measuring the binding of the composition to the first and second test polypeptides, and comparing the binding of the composition and the first test polypeptide to that of the second test polypeptide where differential activity is expressed as a ratio of the two binding affinities.

The compositions screened include but are not limited to chemical, synthetic combinatorial libraries of small molecule ligands, eukaryotic whole cell lysates or extracts, media conditioned by cultured eukaryotic cells, natural products and extracts thereof.

The opioid can be but is not limited to, morphine, methadone, etorphine, levorphanol, fentanyl, sufentanil, [D-Ala$^2$, MePhe$^4$, Gly(ol)$^5$]enkephalin (DAMGO), pentazocine, ethylketocyclazocine, bremazocine, spiradoline, [D-Ser$^{2,}$ Leu$^5$]enkephalin-Thr$^6$ (DSLET), Met-enkephalin, Leu-enkephalin, β-endorphin, dynorphin A, dynorphin B, α-neoendorphin analogs and combinatorial chemistry products thereof.

The physiological effect can be measured by any method known in the art such as changes in the levels of neuroendocrine hormones, including, but not limited to prolactin, growth hormone, gonadotropin-releasing hormone, adrenocorticotropin, corticotropin-releasing factor, luteinizing hormone, follicle stimulating hormone, testosterone or cortisol. The physiological effect can also be measured by changes in the levels of neurotransmitters, including but not limited to, acetylcholine or dopamine.

Activation of an MOR-1 receptor, and likely, the MOR-1 splice variant polypeptides, stimulates a variety of physiological responses, including analgesia, depression of gastrointestinal motility and respiration, and alterations of the immune, endocrine and autonomic nervous system. Compositions that regulate the activity of the MOR-1 receptor and/or the MOR-1 splice variant polypeptides can elicit responses that have therapeutic effects. The invention is useful in diagnosis, treatment, design and screening of novel reagents. Screening of compounds can result in obtaining those with differential or selective activity. That is, for instance, certain compositions can retain analgesic effects but do not affect peristaltic activity and thus do not cause constipation. Conversely, compositions that lack analgesic effects but affect peristaltic activity would be useful in treating chemotherapy and HIV patients. Other applications relating to the side effects of opiates can be readily envisaged by one of skill in the art.

The invention further encompasses a method for regulating morphine analgesia in a subject by altering the amount of MOR-1 splice variant polypeptide activity in the subject. Activity can be regulated by administering antigen binding fragments, agonists, antagonists or small molecule ligands to a subject in an amount and a duration sufficient to regulate morphine analgesia. The antigen binding fragment, agonist, antagonist or small molecule ligand is directed to an MOR-1 splice variant.

Activity can also be regulated by administering a DNA plasmid vector containing an MOR-1 splice variant polynucleotide. The DNA plasmid vector thereby expresses an MOR-1 splice variant polynucleotide in a subject in an amount and a duration sufficient to regulate morphine analgesia. Activity can also be regulated by administering an antisense nucleic acid complementary to an MOR-1 splice variant polynucleotide, thereby blocking gene expression in a subject in an amount and a duration sufficient to regulate morphine analgesia.

The invention further encompasses a method for regulating body weight in a subject by altering the amount of MOR-1 splice variant polypeptide activity. Activity can be regulated by administering antigen binding fragments, agonists, antagonists or small molecule ligands to a subject in an amount and a duration sufficient to regulate body weight. The antigen binding fragment, agonist, antagonist or small molecule ligand is directed to or specific for an MOR-1 splice variant polypeptide.

Activity can also be regulated by administering to a subject a DNA plasmid vector containing an MOR-1 splice variant polynucleotide. The plasmid vector thereby expresses the MOR-1 splice variant polynucleotide in a subject in an amount and a duration sufficient to regulate body weight of the subject. Activity can also be regulated by administering an antisense nucleic acid complementary to an MOR-1 splice variant polynucleotide, thereby blocking gene expression in a subject in an amount and a duration sufficient to regulate body weight.

Agonists and antagonists of MOR-1 splice variant polypeptide activity can include but are not limited to, morphine, methadone, etorphine, levorphanol, fentanyl, sufentanil, [D-Ala$^2$, MePhe$^4$, Gly(ol)5]enkephalin (DAMGO), butorphanol, naloxone, naltrexone, D-Phe-Cys-Tyr-D-Trp-Orn-Thr-Pen-Thr-NH$_2$ (CTOP), diprenorphine, β-funaltrexamine, naloxonazine, nalorphine, pentazocine, nalbuphine, benzoylhydrazone, bremazocine, ethylketocyclazocine, U50488, U69593, spiradoline, naltrindole, [D-Pen$^2$, D-Pen-$^5$]enkephalin (DPDPE), [D-Ala$^2$, Glu$^4$]deltorphin, [D-Ser$^2$, Leu$^5$]enkephalin-Thr$^6$ (DSLET), Met-enkephalin, Leu-enkephalin, β-endorphin, dynorphin A, dynorphin B, α-neoendorphin and derivatives such as those produced by combinatorial chemistry.

A "subject" is a vertebrate, preferably a mammal, and more preferably a human. Mammals include but are not limited to humans, farm animals, sport animals, and pets.

The invention further encompasses a method for diagnosing an MOR-1 splice variant-associated pharmacological abnormality in a subject, comprising measuring the amount of polypeptide activity or tissue distribution of polypeptide and/or polynucleotide in the subject and comparing that activity or tissue distribution to a control sample, wherein a difference in the amount of activity or tissue distribution correlates with the presence of a pharmacological defect. This disorder can be heritable.

The invention further encompasses a method for diagnosing an MOR-1 splice variant-associated disorder of the neuroendocrine system of a subject, comprising measuring the amount of polypeptide activity or tissue distribution of polypeptide and/or polynucleotide thereof in the subject and comparing that activity or tissue distribution to a control sample, wherein a difference in the amount of activity or tissue distribution correlates with the presence of a disorder of the neuroendocrine system. This disorder can be heritable.

The invention further encompasses antigen binding fragments specific for an MOR-1 splice variant polypeptide. According to the invention, an MOR-1 splice variant polypeptide can be used as an immunogen to generate antigen binding fragments which immunospecifically bind the immunogen.

Production of antigen binding fragments such as polyclonal antibodies can be carried out by any method known in the art. Various host animals can be immunized by injection with the immunogen, including but not limited to rabbits, mice and rats. Various adjuvants can be used to increase the immunological response, depending on the host species, and including but not limited to Freund's (complete or incomplete) adjuvant, mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and Corynebacterium parvum.

For preparation of antigen binding fragments such as monoclonal antibodies, any technique which provides for the production of antibody molecules by continuous cell lines in culture can be used. Examples of such techniques include the original hybridoma technique (Kohler and Milstein (1975) Nature 256:495) as well as the trioma technique, the human B-cell hybridoma technique (Kozbor et al. (1983) Immunol. Today 4:72), and the EBV hybridoma technique to produce human monoclonal antibodies (Cole et al. (1985) in Monoclonal Antibodies and Cancer Therapy, Alan R. Liss, Inc., pp. 77–96). Monoclonal antibodies can also be produced in germ-free animals utilizing known technology (PCT/US90/02545). Human antibodies can be obtained using human hybridomas (Cote et al. (1983) Proc. Natl. Acad. Sci. U.S.A. 80:2026), or by transforming human B cells with EBV virus in vitro (Cole et al. (1985)). Techniques developed for the production of "chimeric antibodies" (Morrison et al. (1984) Proc. Natl. Acad. Sci. U.S.A. 81:6851; Neuberger et al. (1984) Nature 312:604; and Takeda et al. (1985) Nature 314:452) by splicing the genes from a mouse antibody molecule specific for MOR-1 splice variants together with genes from a human antibody of appropriate biological activity can be used.

Techniques described for the production of single chain antibodies (U.S. Pat. No. 4,946,778) can be adapted to produce MOR-1 splice variant polypeptide-specific single chain antibodies. Techniques described for the production of Fab expression libraries (Huse et al. (1989) Science 246:1275) can be utilized, allowing rapid and easy identification of monoclonal Fab fragments specific for an MOR-1 splice variant polypeptide.

Antibody fragments which contain the idiotype of the molecule can be generated by known techniques. For example, such fragments include but are not limited to: the F(abl), fragment which can be produced by pepsin digestion of the antibody molecule; the Fab' fragments which can be generated by reducing the disulfide bridges of the F(abl) fragment, the Fab fragments which can be generated by treating the antibody molecule with papain and a reducing agent, and Fv fragments.

Single chain V region fragments ("scFv") can also be produced. Single chain V region fragments are made by linking L (light) and/or H (heavy) chain V (variable) regions by using a short linking peptide. Bird et al. (1988) Science 242:243. Any peptide having sufficient flexibility and length can be used as a linker in a scFv. Usually the linker is selected to have little to no immunogenicity. An example of a linking peptide is (GGGGS)$_3$ (SEQ ID NO: 36), which bridges approximately 3.5 nm between the carboxy terminus of one V region and the amino terminus of another V region. Other linker sequences can also be used, and can provide additional functions, such as for attaching a drug or a solid support.

All or any portion of the H or L chain can be used in any combination. Typically, the entire V regions are included in the scFv. For instance, the L chain V region can be linked to the H chain V region. Alternatively, a portion of the L chain V region can be linked to the H chain V region, or a portion thereof. Also contemplated are scFvs in which the H chain V region is from H11, and the L chain V region is from another immunoglobulin. It is also possible to construct a biphasic, scFv in which one component is an MOR-1 splice variant polypeptide and another component is a different polypeptide, such as a T cell epitope.

The scFvs can be assembled in any order, for example, $V_H$-(linker)-$V_L$ or $V_L$-(linker)-$V_H$. There may be a difference in the level of expression of these two configurations in particular expression systems, in which case one of these forms may be preferred. Tandem scFvs can also be made, such as (X)-(linker)-(X)-(linker)-(X), in which X are MOR-1 splice variant polypeptides, or combinations of MOR-1 splice variant polypeptides with other polypeptides. In another embodiment, single chain antibody polypeptides have no linker polypeptide, or just a short, inflexible linker. Exemplary configurations include $V_L$–$V_H$ and $V_H$–$V_L$. The linkage is too short to permit interaction between $V_L$ and $V_H$ within the chain, and the chains form homodimers with a $V_L$/$V_H$ antigen binding site at each end. Such molecules are referred to in the art as "diabodies".

ScFvs can be produced either recombinantly or synthetically. For synthetic production of scFv, an automated synthesizer can be used. For recombinant production of scFv, a suitable plasmid containing a polynucleotide that encodes the scFv can be introduced into a suitable host cell, either eukaryotic, such as yeast, plant, insect or mammalian cells, or prokaryotic, such as *Escherichia coli*, and the protein expressed by the polynucleotide can be isolated using standard protein purification techniques.

A particularly useful system for the production of scFvs is plasmid pET-22b(+) (Novagen, Madison, Wis.) in *E. coli*. pET-22b(+) contains a nickel ion binding domain consisting of 6 sequential histidine residues, which allows the expressed protein to be purified on a suitable affinity resin. Another example of a suitable vector is pcDNA3 (Invitrogen, San Diego, Calif.), described above.

The following examples are provided to illustrate but not limit the claimed invention.

EXAMPLE 1

Identification of MOR-1C, MOR-1D, and MOR-1E cDNA Sequences

The cDNA clones of the MOR-1 splice variants MOR-1c, MOR-1d, and MOR-1e were isolated using 3'-Rapid Amplification of cDNA Ends (RACE) and Reverse Transcription Polymerase Chain Reaction (RT-PCR). First, standard PCR reactions were performed using a Marathon cDNA Amplification Kit (Clontech) and a Marathon-Ready mouse cDNA Library. A sense primer located at the 3'-end of exon 3, nucleotide position 1338 to 1359 of the mouse mu-opioid receptor, and an antisense adapter primer were used to PCR amplify a mouse brain cDNA template. The PCR products were separated on an agarose gel.

Multiple bands were amplified and each band was excised. Individual bands were amplified using a second set of nested primers, including a sense primer located at position 1394–1412 of the MOR-1 receptor, and an antisense adapter primer. The resulting PCR fragments were then subcloned into Bluescript plasmids and sequenced.

The sequence of one clone, 110222, was approximately 500 bp in length and failed to align with the sequence of MOR-1 (GenBank Accession #U26915). Clone 110222 contained partial 3' MOR-1 exon 3 sequences followed by a novel sequence. The new sequence was 454 bp long and open reading frame analysis predicted 7 amino acids beyond exon 3 followed by a termination codon and a 3' untranslated region (UTR).

To obtain full length cDNA clones of the 110222 variant, a sense primer corresponding to the 5' UTR of MOR-1, nucleotide position 217 to 240, and an antisense primer corresponding to the 3+ UTR of the new sequence, antisense primer A (5' CCA CAC TGC TCA CCA GCT CAT CCC 3') (SEQ ID NO: 37), were used in RT-PCR amplification of mouse brain RNA. Three fragments of approximately 1.3, 1.4 and 1.5 kb in length, respectively, were obtained, subcloned into pCRII-ToPo plasmid (Invitrogen, Carlsbad, Calif.) and sequenced in both directions.

The three clones obtained are named MOR-1c, MOR-1d and MOR-1e. Through sequence analysis it was determined that all three clones contain the same coding exons 1, 2 and 3 from MOR-1, with novel sequences beginning downstream of exon 3. In addition, MOR-1c and MOR-1e contain an alternate exon. MOR-1d aligned with the original clone 110222. MOR-1c contains an 89 bp insertion between exon 3 and the 454 bp sequence identified in MOR-1d. MOR-1e has a 209 bp insertion between exon 3 and the 454 bp sequence identified in MOR-1d, making it the longest novel sequence. The last 89 bp in this insertion are identical to the 89 bp sequence found in MOR-1c. (FIG. 2).

The three new variants are derived from combinations of five newly discovered exons located downstream from the original MOR-1 exon 4. Exon 6 is 120 bp, exon 7 is 89 bp, exon 8 is 66 bp, and exon 9 is the longest, 388 bp. MOR-1d encodes exons 1, 2, 3, 8 and 9 (FIG. 2), MOR-1c encodes exons 1, 2, 3, 7, 8 and 9 (FIG. 2), and MOR-1e encodes exons 1, 2, 3, 6, 7, 8, and 9. (FIG. 2). All of the new exons have flanking sequences that are consistent with consensus splice junctions. Thus, the MOR-1 gene consists of nine exons spanning at least 200 kb. This is depicted in FIG. 1.

The predicted amino acid sequences for these new variants differ from MOR-1 and from each other. MOR-1 has 12 predicted amino acids. MOR-1d has only 7 predicted amino acids. Although MOR-1c contains the same new sequence found in MOR-1d, the 89 bp insertion produces a reading-frame shift. As a result, open reading frame analysis of MOR-1c predicts 52 amino acids, which do not include the amino acid sequence from MOR-1d. The termination codon in MOR-1e is found in exon 6, therefore exons 7, 8 and 9 are not translated and MOR-1e is translated into only 15 amino acids.

Partial human mu opioid splice variant sequences were obtained using RT-PCR approach. We amplified a cDNA fragment from human brain which contained an alternatively spliced exon 4 of human MOR-1 gene. In the PCR reaction, template was the first-strand cDNA reverse-transcribed from human brain mRNA, and a sense primer derived from exon 3 of the human MOR-1 gene, and an antisense primer from exon 7 of the mouse MOR-1 gene (5' TGT CCA TGC AAC TCT TGC AGG GTT TTT CAA CAT GAG TCG GAG AAG GAT3') (SED ID NO: 38). Sequence analysis of the fragment indicated that it contains the human exon 3 sequences from the sense primer to the end of exon 3 and a 104 bp new sequence between exon 3 and the mouse antisense primer. (FIG. 2). Translation of the sequence from exon 3 into the new sequence indicates that it encodes 34 AA with no homology to any mouse variants. (FIG. 3). However it does not contain a stop codon, which suggests there is more downstream exon sequence. The new sequence has been mapped, in a human genomic BAC clone to 10 kb downstream of human exon 4.

Figure 5:
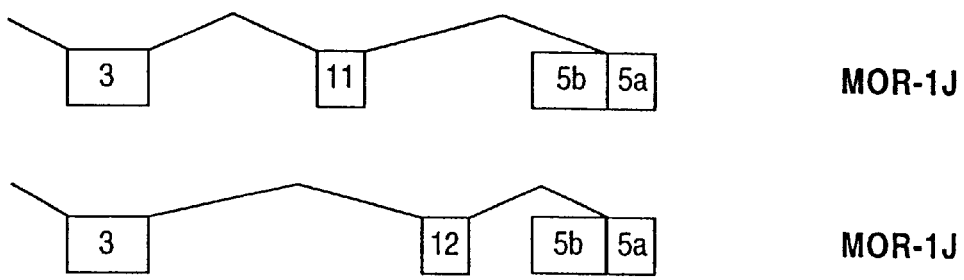
FIG. 5 is a schematic diagram comparing the exons of MOR-1I and MOR-1J.

A sense primer designed from exon 3 (5'GGG AAC ACC CCT CCA CGG3') (SEQ ID NO: 39) and an antisense primer from exon 5a (5'GGT GTG CTT CTC CCA GTT CTG TGT3') (SEQ ID NO: 40) were used in RT-PCR of mouse brain RNA. Two fragments of approximately 0.2 and 0.7 kb in length, respectivley, were obtained, subcloned into pcRIIToPo plasmid and sequenced. Sequence analysis indicates that the 0.2 kb fragment, MOR-1I, contains exon 3 and 5a except that there is a 94 kb insertion, exon 11, between exons 3 and 5a. (FIG. 2). Exon 11 only encodes 2AA (CV). The 0.7 kb fragment, MOR-1J, also contains exons 3 and 5a sequences, but there is a 617 bp insertion, exon 12, between exons 3 and 5a. Exon 12 encodes 7AA. (FIGS. 3 and 5).

Cloning Strategy for 161416

A sense primer designed from exon 1a (5'CCT CCA GGC TCA TTT CAG AGA GA3') (SEQ ID NO: 41) and an antisense primer from exon 1 (5'CAG GAA GTT TCC AAA GAG GCC C3') (SEQ ID NO: 42) were used in RT-PCR of mouse brain RNA. The PCR fragment obtained was subcloned into pcRIIToPo plasmid and sequenced. Sequence analysis of the fragment indicates that there is a 127 bp insertion sequence, exon 1b, between exons 1a and 1. (FIG. 2).

Cloning Strategy for 2730510 and 3320510

Figure 6:
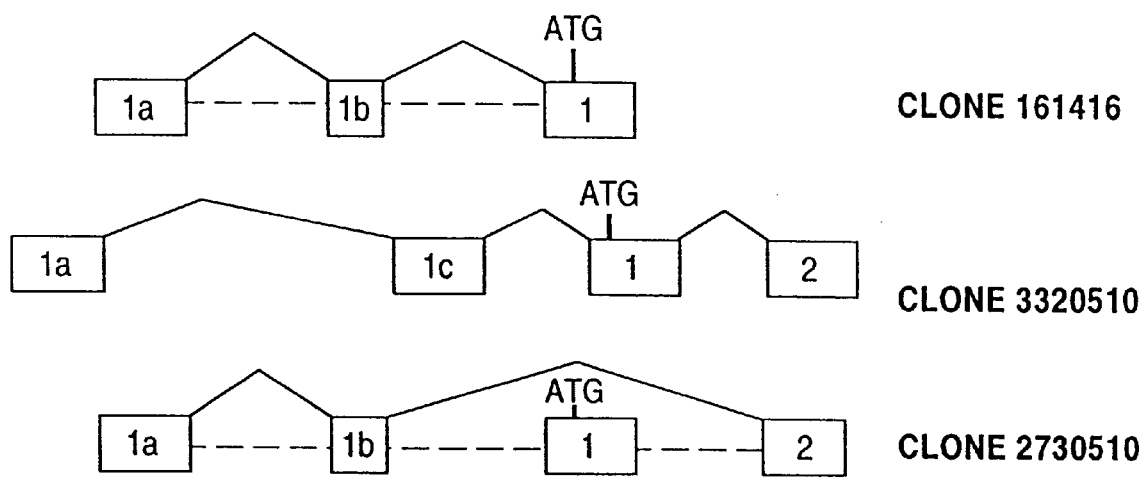
FIG. 6 is a schematic diagram comparing the exons of Clones 161416; 3320510 and 2730150.

The sense primer above (exon 1a) and an antisense primer from exon 2 (5'GGG CAG GTG GTA GTG GCT AAG GC3') (SEQ ID NO: 43) were used in RT-PCR of mouse brain RNA. Two fragments of approximately 0.26 and 0.6 kb in length, respectively, were obtained, subcloned into pcRIIToPo plasmid and sequenced. Sequence analysis indicated that the 0.26 kb fragment, clone 2730510, contains both exons 1a, 2 and 1b, with exon 1b between exons 1a and 2. The clone 3320510, however, contains exons 1a, 1c, 1 and 2. (FIGS. 2 and 6).

Cloning Strategy for mMOR-1IBI and mMOR-1BII

Mouse exon 5a sequence was obtained by sequencing mouse Genome BAC clone A using primers derived from rat MOR-1B sequences (Zimprich et al. (1995)). Then an antisense primer designed from the mouse exon 5a and a sense primer from the 5' UTR of MOR-1 nucleotide position 217 to 240 were used in RT-PCR amplification of mouse brain RNA. Two fragments of approximately 1.3 and 2.0 kb in length, respectively, were obtained, subcloned into PCRII-ToPo plasmid and sequenced. Sequence analysis of the fragments indicated that similar to rat MOR-1B, the 1.3 kb fragment contains exons 1, 2, 3 and 5a which encodes 5 AA (KIDLE) (SEQ ID NO: 44). However, the 2.0 kb fragment had the same exons 1, 2, 3 and 5a, except that there is a 699 bp insertion sequence, exon 5b, between exons 3 and 5a. Exon 5b encodes 23 AA KLLMWRAMPT-FKRHLAIMLSLDN (SEQ ID NO: 45). (FIGS. 2 and 3).

Cloning Strategy for mMOR-1A

First, we obtained mouse exon 3a sequence by sequencing mouse Genomic BAC clone A with exon 3 primers. The full length cDNA of mMOR-1A was then obtained by RT-PCR using the first-strand cDNA reverse-transcribed from mouse brain total RNA as template. A sense primer corresponding to the 5' UTR of MOR-1, nucleotide position 217 to 240, and an antisense primer corresponding to the 3' UTR of exon 3a (5'GAT CAG AAT TTG GTG CCC TAC TCC CTC TCT3') (SEQ ID NO: 46) were used in PCR. The PCR fragment was subcloned into pcRIIToPo plasmid and sequenced. Sequence analysis of the fragment showed that exon splice pattern was exons 1, 2, 3 and 3a which encodes 4AA (VCAF). (FIGS. 2 and 3).

EXAMPLE 2

Mapping of the MOR-1 Gene to Mouse Chromosome 10

In order to obtain genomic clones containing the full-length MOR-1 gene, two mouse genomic BAC libraries (Genome Systems, St. Louis, Mo. and Research Genetics, Huntsville, Ala.) and a mouse genomic P1 library (Genome Systems) were screened using either PCR or standard hybridization methods. Initially, BAC clone A (~75 kb), was obtained from the Genome Systems BAC library using MOR-1 exon 4 primers for PCR amplification. BAC clone A contained only MOR-1 exons 1, 2, 3 and 4. Since no positive clones were obtained by screening the BAC library with a probe corresponding to exons 8 and 9, we screened the P1 library with this probe and obtained P1 clone A (~100 kb in length). P1 clone A contained exon 8 and 9 sequences, however, it shared no overlapping sequences with either BAC clone A or exons 6 and 7. To identify a clone containing these insertions, a second mouse BAC library (Research Genetics, Inc.) was screened by hybridization with a probe corresponding to the insertional sequences (exon 6). One new clone, BAC clone B (~120 kb) contained exons 4, 6 and 7. Alignment of the three genomic clones predicted an MOR-1 gene of approximately 230 kb.

Chromosomal localization of P1 clone A was carried out using FISH methods developed by Genome Systems, Inc. P1 clone A was labeled with digoxigenin dUTP and hybridized to metaphase chromosomes derived from a mouse embryo fibroblast cell line. Specific hybridization signals were detected by incubating the hybridized slides in fluoresceinated anti-digoxigenin antibodies followed by counterstaining with DAPI. The initial experiment resulted in specific labeling of the proximal portion of a medium sized chromosome, identified as chromosome 10 on the basis of DAPI staining. Cohybridization of a specific probe for the telomeric region of chromosome 10 with the P1 clone A demonstrated conclusively that the P1 clone A was located immediately adjacent to the heterochromatic euchromatic boundary of chromosome 10, an area corresponding to band 10A2. A total of 80 metaphase cells were analyzed with 68 exhibiting specific labeling. Genome Systems Inc. used interphase FISH analysis (van den Engh et al. (1992) Science 257:1410) to estimate the physical distance between the BAC clone A and the P1 clone A. The distance between the BAC clone A and the P1 clone A estimated was approximately 250 kb, with a possible error of approximately 30%. This was in agreement with the size derived from the overlapping genomic clones, which predicted an MOR-1 gene of approximately 230 kb. (FIG. 2).

EXAMPLE 3

Expression Patterns of the MOR-1 Variants

To determine the lengths of the mRNA transcripts encoding the MOR-1 variants, Northern blot analysis was performed as described previously by Pan et al. (1994). Total RNA was isolated from mouse brain using the guanidinium thiocyanate phenol-chloroform extraction method. Samples of total brain RNA (50 µg) were separated on a 0.8% formaldehyde agarose gel, and transferred to a Gene Plus membrane. The membrane was hybridized with $^{32}$P-labeled fragments corresponding to sequences from exons 7, 8, and 9 of the MOR-1 variants.

Figure 7:
FIG. 7 depicts the results of Northern blots performed on mouse brain using an exon 4 probe and a probe including exons 7/8/9.

Northern analysis of the variants indicates mRNA transcripts ranging in size from approximately 6 to 9 kb (FIG. 7). A probe specific for exon 7 would detect only MOR-1c and MOR-1e. A probe specific for exon 6 fails to detect MOR-1e mRNA.

The regional pattern of MOR-1 variant mRNA expression was determined using RT-PCR analysis. Total RNA was extracted from multiple mouse brain regions as described above and reverse-transcribed with Super Script II Reverse Transcriptase (GIBCO) in the presence of random hexamers. RNA loading was estimated by comparison to a parallel PCR reaction using $\beta_2$-microglobulin primers (ClonTech). The agarose gel was stained with ethidium bromide and photographed by a Kodak DC120 Digital Camera and Imagine System. Three major bands were amplified and the predicted sizes of the PCR products for MOR-1c, MOR-1d and MOR-1e are 246 bp, 157 bp and 366 bp, respectively. Each band was extracted from the agarose gel, subcloned into a pCRII-ToPo plasmid and sequenced, confirming that the amplification products corresponded to their respective variants.

Figure 8A:
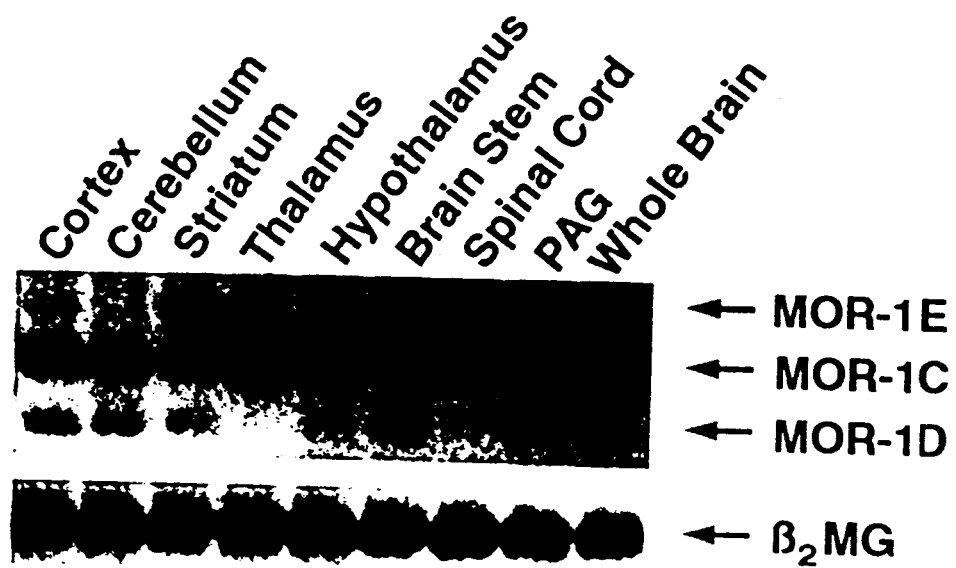

MOR-1c is the predominant isoform in all of the brain regions examined, but the relative expression of the other variants varied widely (FIG. 8A). MOR-1 was expressed in all regions (FIG. 8B). MOR-1e and MOR-1d display differential patterns of expression. In the thalamus, there is little evidence for either MOR-1d or MOR-1e expression. MOR-1c mRNA is predominant in the spinal cord, with lower levels of MOR-1e expression and no observable MOR-1d expression present. In contrast, the periaqueductal gray (PAG) and striatum, all three of the variants are detected, with the highest levels of expression displayed by MOR-1c, followed by MOR-1e and then MOR-1d. The cortex has comparably higher levels of MOR-1d expression than MOR-1e expression, as do the cerebellum and brainstem.

Regional distribution of MOR-1c was analyzed using a polyclonal antibody generated against a unique amino acid sequence in this variant. Mouse brains were sectioned and immunostaining for MOR-1 and MOR-1c determined as described. Abbadie et al. (1996) Neuroscience 70:201; Abbadie et al. (1999) Proc. Natl. Acad. Sci. U.S.A. 96:260); and Abbadie et al. (1999) submitted. Sections A and B and sections C and D were stained with MOR-1 and MOR-1C antisera, respectively. Regions were as follows: A and B) St, striatum; ac, anterior commissure; Ac, accumbens; LS, lateral septum; C) MD, mediodorsal thalamic nucleus; CM, centromedial thalamic nucleus; DH, dorsal hypothalamic nucleus; VMH, ventromedial hypothalamic nucleus; LH, lateral hypothalamic nucleus; Ce, central amygdaloid nucleus; Ic, intercalated amygdaloid nucleus; Me, medial amygdaloid nucleus; D) Ar, arcuate nucleus; ME, median eminence. Western blotting showed that the polyclonal antibody recognized MOR-1C, but not MOR-1 obtained from transfected cells.

Sections through the striatum (FIGS. 9A and B) demonstrate marked differences between MOR-1 and MOR-1c. MOR-1 immunolabeling is observed in patches in the striatum, as well as in the subcallosal streak. Dense areas of labeling are also seen in the nucleus accumbens. MOR-1c antiserum fails to label these areas. There is MOR-1c immunoreactivity in regions of the lateral septum which have minimal staining with MOR-1 antiserum. The hypothalamus has significant differences between the two antisera (FIGS. 9C and D). While there is some MOR-1 staining, MOR-1c immunoreactivity is far more intense in the arcuate nucleus and median eminence. Additional studies show intense MOR-1c immunoreactivity in the trigeminal tract and the dorsal horn of the spinal cord, as well as the PAG.

EXAMPLE 4

Binding Activity of the Variants

Figure 10:
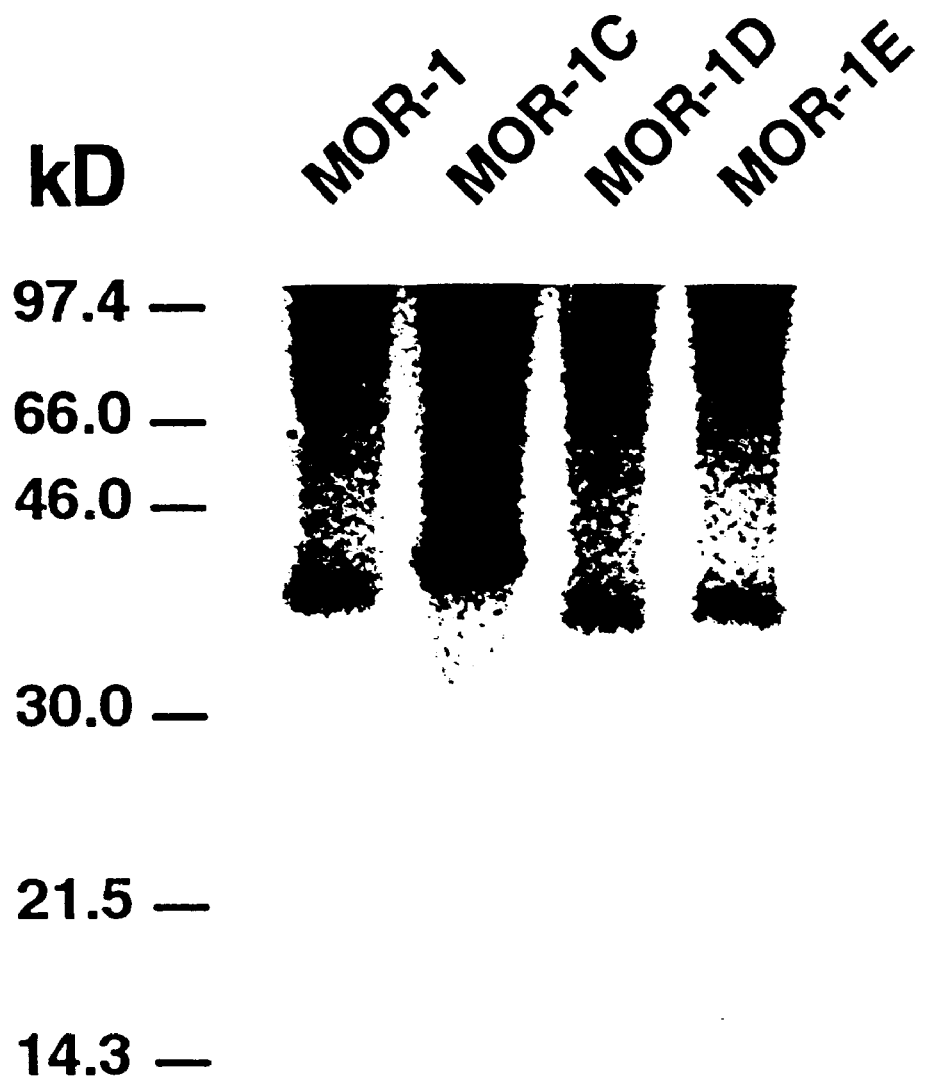
FIG. 10 depicts in vitro translation of MOR-1, MOR-1C, MOR-1D and MOR-1E.

The cDNA fragments containing the full length MOR-1 or the MOR-1 variants in pCRII-ToPo were subcloned into pcDNA3.1 (Invitrogen, Carlsbad, Calif.), a mammalian expression vector. Synthesis of MOR-1C, MOR-1D, and MOR-1E full-length proteins was carried out in vitro using a TNT coupled reticulocyte lysate kit (Promega, Madison, Wis.). MOR-1/pcDNA3, MOR-1c/pcDNA3, and MOR-1d/pcDNA3 plasmids were incubated with T7 RNA polymerase and reticulocyte lysate in the presence of 0.04 mCi of [$^{35}$S]methionine (>1000 Ci/mmol; DuPont-NEN, Boston, Mass.) at 300C for 1 hour. The translation products were separated by a 12.5% SDS-PAGE gel, which was treated with Amplify (Amersham Life Science), dried and exposed on Kodak BioMax MR film. The MOR-1D and MOR-1E variants had molecular weights similar to that of MOR-1, while the size of MOR-1C was larger than the others, as expected based upon the predicted amino acid sequences (FIGS. 3 and 10).

CHO cells were stably transfected with plasmids MOR-1/pcDNA3, MOR-1c/pcDNA3, MOR-1d/pcDNA3 or MOR-1e/pcDNA3 using LipofectAMINE reagents (GIBCO, Gaithersburg, Md.). Stable transformants were subcloned two weeks after selection with G418 and positive clones were identified using a $^3$H-DAMGO binding assay.

To examine opioid binding, membranes were prepared from pcDNA3 stable transformants as described previously by Pan et al. (1994); and Pan et al. (1996). $^3$H-DAMGO binding was performed at 25° C. for 60 minutes in 50 mM potassium phosphate buffer, pH 7.4, containing 5 mM magnesium sulfate. Specific binding was defined as the difference between total binding and nonspecific binding, as indicated by levallorphan (1 μM). $K_D$ and $K_I$ values were calculated by nonlinear regression analysis (Prism, Graph Pad Software). Protein concentrations were determined against bovine serum albumin as the standard curve. Lowry et al. (1951) J. Biol. Chem. 193:265.

Saturation studies were performed and the binding parameters established by nonlinear regression analysis. $^3$H-DAMGO binding was examined in stable lines expressing either MOR-1 or MOR-1C.

In saturation studies $^3$H-DAMGO displays high affinity for all the variants (Table 1). Indeed, the new variants bind $^3$H-DAMGO with higher affinities than MOR-1. Results are reported as the means ±s.e.m of at least 3 independent determinations.

TABLE 1

| Clone | $K_D$ (nM) |
|---|---|
| MOR-1 | 1.75 ± 0.44 |
| MOR-1C | 0.93 ± 0.19 |
| MOR-1D | 0.72 ± 0.11 |
| MOR-1E | 1.2 ± 0.5 |

Competition studies were performed using at least three concentrations of the indicated competitor. $^3$H-DAMGO binding was performed in stable transfectants containing the indicated cDNA's. Analysis of variance was performed to determine whether there were differences among the various clones for each competitor, followed by Tukey's post hoc analysis.

In competition studies, mu ligands such as morphine, DAMGO, M6G and the endorphins bind competitively while the kappa$_1$ opioid U50,488H and the delta opioid ligand [D-Pen$^2$, D-Pen$^5$]enkephalin (DPDPE) are ineffective. However, the binding selectivity profiles among the variants are significantly different. For example, morphine competes for binding to the MOR-1D variant over 3-fold more potently than against MOR-1 itself (p<0.05). Similarly, the opioid peptide DSLET is twice as potent against binding to the MOR-1D variant than MOR-1 (p<0.05). The most dramatic differences in potency are seen with the endogenous opioids dynorphin A (p<0.0001) and β-endorphin (p<0.0003). The MOR-1D variant has the highest affinity for both dynorphin A and β-endorphin. MOR-1E also has a significantly higher affinity for β-endorphin than MOR-1. Dynorphin A has significantly higher affinity for MOR-1C and MOR-1D than either MOR-1 or MOR-1E. Through competition studies all of the variants have been classified within the mu opioid receptor family (Table 2). Results are reported as the means ±s.e.m. of at least 3 independent determinations.

TABLE 2

Selectivity of MOR-1 and MOR-1C in the receptor binding assay

| | $K_i$ value (nM) | | | | | Tukey |
|---|---|---|---|---|---|---|
| Ligand | MOR-1 | MOR-1C | MOR-1D | MOR-1E | ANOVA | MOR:P value |
| Morphine | 5.3 ± 2.0 | 2.4 ± 0.6 | 1.5 ± 0.2 | 2.3 ± 0.4 | | 1vs1D:P < 0.05 |
| M6G | 5.2 ± 1.8 | 4.1 ± 1.2 | 4.8 ± 0.8 | 5.6 ± 0.7 | N.S. | |
| DAMGO | 1.8 ± 0.5 | 0.93 ± 0.19 | 0.71 ± 0.11 | 1.2 ± 0.5 | N.S. | |
| DADLE | 2.1 ± 0.3 | 3.2 ± 1.9 | 1.3 ± 0.4 | 2.5 ± 0.7 | N.S. | |

EXAMPLE 5

Functional Significance of the Variants

Antisense mapping was used to explore the functional significance of these new variants. Pasternak and Standifer (1995); and Standifer et al. (1994). This method has been used extensively to correlate opioid pharmacology with the function of the MOR-1 receptor. Rossi et al. (1994); Rossi et al. (1995); Rossi et al. (1995); and Kolesnikov et al. (1996). Groups of mice (n ≧20) received antisense oligodeoxynucleotides corresponding to specific MOR-1, MOR-1c, MOR-1d, or MOR-1e exons daily for five days. Following administration of the antisense probes, analgesia was assessed by the radiant heat tailflick assay. Rossi et al. (1996); and Rossi et al. (1995). This assay was performed by exposing tails to a light source and determining the baseline latency (typically between 2 and 3 sec). Analgesia was indicated when doubling of the baseline latency occurred. Significance between groups was assessed using the Fisher Exact Test.

Figure 11:
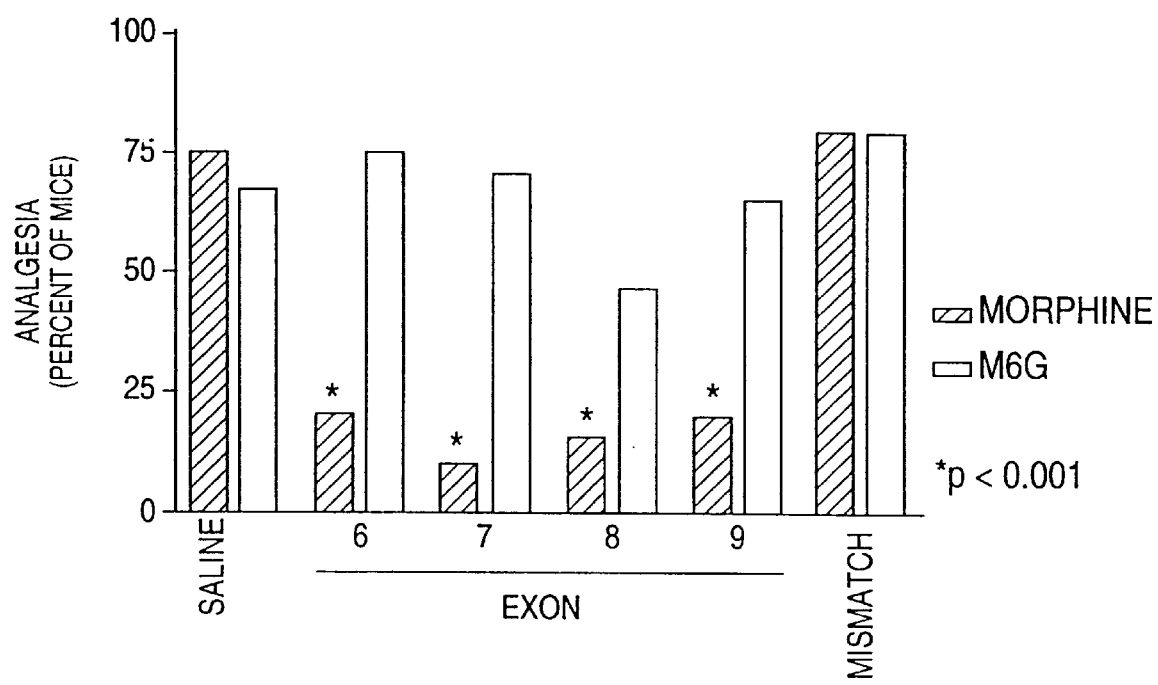
FIG. 11 depicts antisense mapping of exons 6, 7, 8 and 9 of MOR-1. The solid bars represent M6G and the stippled bars represent morphine treatment.

The remaining activity of the variants was measured following administration of the antisense probes in the presence of both morphine and M6G analgesia (FIG. 11), two mu drugs whose actions have been distinguished using antisense approaches. Rossi et al. (1994); Rossi et al. (1995); and Rossi et al., (1995). All four antisense probes significantly lowered morphine analgesia (FIG. 11). A mismatch control probe targeted against exon 7 was inactive, confirming the specificity of the response.

In contrast to their significant blockade of morphine analgesia, none of the antisense probes significantly lowered M6G analgesia. Thus, these exons are not a component of the postulated M6G receptor. The reduction in morphine analgesia produced by the antisense probes implies that each of the variant mRNAs, and ultimately the receptor(s) which they encode, are involved in mediating morphine analgesia.

All references cited herein, are hereby incorporated herein. Although the foregoing invention has been described in some detail, by way of illustration and example for the purposes of clarity and understanding, it will be apparent to those skilled in the art that certain changes and modifications can be practiced. Therefore, the description and examples should not be construed as limiting the scope of the invention, which is delineated by the appended claims.

SEQUENCE LISTING

<160> NUMBER OF SEQ ID NOS: 46

<210> SEQ ID NO 1
<211> LENGTH: 1423
<212> TYPE: DNA
<213> ORGANISM: Mus musculus

<400> SEQUENCE: 1

```
ggaacccgaa cactcttgag tgctctcagt tacagcctac cgagtccgca gcaagcattc      60
agaaccatgg acagcagcgc cggcccaggg aacatcagcg actgctctga cccttagct     120 cctgcaagtt gctccccagc acctggctcc tggctcaact tgtcccacgt tgatggcaac    180
cagtccgacc catgcggtcc taaccgcacg gggcttggcg ggagccacag cctgtgccct    240
cagaccggca gccttccat ggtcacagcc atcaccatca tggccctcta ttctatcgtg     300
tgtgtagtgg gcctctttgg aaacttcctg gtcatgtatg tgattgtaag ataaccaaa     360 atgaagactg ccaccaacat ctacatttttc aaccttgctc tggcagatgc cttagccact   420
agcacgctgc cctttcagag tgttaactac ctgatgggaa cgtggccctt tggaaacatc    480
ctctgcaaga tcgtgatctc aatagactac tacaacatgt tcaccagtat cttcacctc    540 tgcaccatga gtgtagaccg ctacattgcc gtctgccacc cggtcaaggc cctggatttc    600
cgtacccccc gaaatgccaa aattgtcaat gtctgcaact ggatcctctc ttctgccatt    660
ggtctgcccg taatgttcat ggcaaccaca aaatacaggc aggggtccat agattgcacc    720
ctcacgttct ctcatcccac atggtactgg gagaacctgc tcaaaatctg tgtcttcatc    780
ttcgccttca tcatgccggt cctcatcatc actgtgtgtt atggactgat gatcttacga    840
ctcaagagtg tccgcatgct gtcgggctcc aaagaaaagg acaggaacct gcgcaggatc    900
acccggatgg tgctggtggt cgtggctgta tttattgtct gctggacccc catccacatc    960
tatgtcatca tcaaagcact gatcacgatt ccagaaacca ctttccagac tgtttcctgg   1020
cacttctgca ttgccttggg ttacacaaac agctgcctga acccagttct ttatgcgttc   1080
ctggatgaaa acttcaaacg atgttttaga gagttctgca tcccaacttc ctccacaatc   1140
gaacagcaaa actctgctcg aatccgtcaa aacactaggg aacacccctc cacggctaat   1200
acagtggatc gaactaacca ccagccaacc ctggcagtca gcgtggccca gatctttaca   1260
```

-continued

| | |
|---|---|
| ggatatcctt ctccgactca tgttgaaaaa ccctgcaaga gttgcatgga cagaggaatg | 1320 |
| aggaaccttc ttcctgatga tggcccaaga caggaatccg gggaaggcca gcttggcagg | 1380 |
| tgaatgtcat ccgaacacag ggatgagctg gtgagcagtg tgg | 1423 |

<210> SEQ ID NO 2
<211> LENGTH: 1238
<212> TYPE: DNA
<213> ORGANISM: Mus musculus

<400> SEQUENCE: 2

| | |
|---|---|
| ttttactgtc cttgagaatg gagaggatca gcaaagctgg aagccctcca ggctcatttc | 60 |
| agagagaata ttccacagag cttgaaggcg cgggatctgg gccgatgatg gaagctttct | 120 |
| ctaagtctgc attccaaaag ctcagacaga gagatggaaa tcagaggggg aagagctacc | 180 |
| tcagatatac caaaatgaag actgccacca acatctacat tttcaacctt gctctggcag | 240 |
| atgccttagc cactagcacg ctgccctttc agagtgttaa ctacctgatg ggaacgtggc | 300 |
| cctttggaaa catcctctgc aagatcgtga tctcaataga ctactacaac atgttcacca | 360 |
| gtatcttcac cctctgcacc atgagtgtag accgctacat tgccgtctgc cacccggtca | 420 |
| aggccctgga tttccgtacc ccccgaaatg ccaaaattgt caatgtctgc aactggatcc | 480 |
| tctcttctgc cattggtctg cccgtaatgt tcatggcaac cacaaaatac aggcagggt | 540 |
| ccatagattg caccctcacg ttctctcatc ccacatggta ctgggagaac ctgctcaaaa | 600 |
| tctgtgtctt catcttcgcc ttcatcatgc cggtcctcat catcactgtg tgttatggac | 660 |
| tgatgatctt acgactcaag agtgtccgca tgctgtcggg ctccaaagaa aaggacagga | 720 |
| acctgcgcag gatcacccgg atggtgctgg tggtcgtggc tgtatttatt gtctgctgga | 780 |
| cccccatcca catctatgtc atcatcaaag cactgatcac gattccagaa accacttcc | 840 |
| agactgtttc ctggcacttc tgcattgcct tgggttacac aaacagctgc ctgaacccag | 900 |
| ttctttatgc gttcctggat gaaaacttca acgatgtttt tagagagttc tgcatcccaa | 960 |
| cttcctccac aatcgaacag caaaactctg ctcgaatccg tcaaaacact agggaacacc | 1020 |
| cctccacggc taatacagtg gatcgaacta accaccagct agaaaatctg gaagcagaaa | 1080 |
| ctgctccatt gccctaactg gtcccacgc catccagacc ctcgctaaac ttagaggctg | 1140 |
| ccatctactt ggaatcaggt tgctgtcagg gtttgtggga ggctctggtt tcctggaaaa | 1200 |
| gcatctgatc ctgcattcaa agtcattcta actgggtc | 1238 |

<210> SEQ ID NO 3
<211> LENGTH: 1334
<212> TYPE: DNA
<213> ORGANISM: Mus musculus

<400> SEQUENCE: 3

| | |
|---|---|
| ggaacccgaa cactcttgag tgctctcagt tacagcctac cgagtccgca gcaagcattc | 60 |
| agaaccatgg acagcagcgc cggcccaggg aacatcagcg actgctctga ccccttagct | 120 |
| cctgcaagtt gctccccagc acctggctcc tggctcaact tgtcccacgt tgatggcaac | 180 |
| cagtccgacc catgcggtcc taaccgcacg gggcttggcg ggagccacag cctgtgccct | 240 |
| cagaccggca gcccttccat ggtcacagcc atcaccatca tggccctcta ttctatcgtg | 300 |
| tgtgtagtgg gcctctttgg aaacttcctg gtcatgtatg tgattgtaag ataccaaa | 360 |
| atgaagactg ccaccaacat ctacattttc aaccttgctc tggcagatgc cttagccact | 420 |

-continued

```
agcacgctgc cctttcagag tgttaactac ctgatgggaa cgtggccctt tggaaacatc    480
ctctgcaaga tcgtgatctc aatagactac tacaacatgt tcaccagtat cttcaccctc    540
tgcaccatga gtgtagaccg ctacattgcc gtctgccacc cggtcaaggc cctggatttc    600 cgtaccccc gaaatgccaa aattgtcaat gtctgcaact ggatcctctc ttctgccatt     660
ggtctgcccg taatgttcat ggcaaccaca aaatacaggc aggggtccat agattgcacc    720
ctcacgttct ctcatcccac atggtactgg gagaacctgc tcaaaatctg tgtcttcatc    780
ttcgccttca tcatgccggt cctcatcatc actgtgtgtt atggactgat gatcttacga    840
ctcaagagtg tccgcatgct gtcgggctcc aaagaaaagg acaggaacct gcgcaggatc    900
acccggatgg tgctggtggt cgtggctgta tttattgtct gctggacccc catccacatc    960
tatgtcatca tcaaagcact gatcacgatt ccagaaacca ctttccagac tgtttcctgg   1020
cacttctgca ttgccttggg ttacacaaac agctgcctga acccagttct ttatgcgttc   1080
ctggatgaaa acttcaaacg atgttttaga gagttctgca tcccaacttc ctccacaatc   1140
gaacagcaaa actctgctcg aatccgtcaa aacactaggg aacacccctc cacggctaat   1200
acagtggatc gaactaacca ccagaggaat gaggaacctt cttcctgatg atggcccaag   1260
acaggaatcc ggggaaggcc agcttggcag gtgaatgtca tccgaacaca gggatgagct   1320
ggtgagcagt gtgg                                                     1334
```

<210> SEQ ID NO 4
<211> LENGTH: 1542
<212> TYPE: DNA
<213> ORGANISM: Mus musculus

<400> SEQUENCE: 4

```
ggaacccgaa cactcttgag tgctctcagt tacagcctac cgagtccgca gcaagcattc     60
agaaccatgg acagcagcgc cggcccaggg aacatcagcg actgctctga ccccttagct    120
cctgcaagtt gctccccagc acctggctcc tggctcaact tgtcccacgt tgatggcaac    180
cagtccgacc catgcggtcc taaccgcacg gggcttggcg ggagccacag cctgtgccct    240
cagaccggca gcccttccat ggtcacagcc atcaccatca tggccctcta ttctatcgtg    300
tgtgtagtgg gcctctttgg aaacttcctg gtcatgtatg tgattgtaag ataaccaaa     360 atgaagactg ccaccaacat ctacattttc aaccttgctc tggcagatgc cttagccact    420
agcacgctgc cctttcagag tgttaactac ctgatgggaa cgtggccctt tggaaacatc    480
ctctgcaaga tcgtgatctc aatagactac tacaacatgt tcaccagtat cttcaccctc    540
tgcaccatga gtgtagaccg ctacattgcc gtctgccacc cggtcaaggc cctggatttc    600 cgtaccccc gaaatgccaa aattgtcaat gtctgcaact ggatcctctc ttctgccatt     660
ggtctgcccg taatgttcat ggcaaccaca aaatacaggc aggggtccat agattgcacc    720
ctcacgttct ctcatcccac atggtactgg gagaacctgc tcaaaatctg ttgcttcatc    780
ttcgccttca tcatgccggt cctcatcatc actgtgtgtt atggactgat gatcttacga    840
ctcaagagtg tccgcatgct gtcgggctcc aaagaaaagg acaggaacct gcgcaggatc    900
acccggatgg tgctggtggt cgtggctgta tttattgtct gctggacccc catccacatc    960
tatgtcatca tcaaagcact gatcacgatt ccagaaacca ctttccagac tgtttcctgg   1020
cacttctgca ttgccttggg ttacacaaac agctgcctga acccagttct ttatgcgttc   1080
ctggatgaaa acttcaaacg atgttttaga gagttctgca tcccaacttc ctccacaatc   1140
gaacagcaaa actctgctcg aatccgtcaa aacactaggg aacacccctc cacggctaat   1200
```

-continued

```
acagtggatc gaactaacca ccagaagaaa aagctggact cccagagagg gtgtgtacag    1260
catccagtgt gacctgtccc ttgtctttga gcctggggc catcttcttt cacagcatac    1320
atttccttgt atcctctctg aagccaaccc tggcagtcag cgtggcccag atctttacag    1380
gatatccttc tccgactcat gttgaaaaac cctgcaagag ttgcatggac agaggaatga    1440
ggaaccttct tcctgatgat ggcccaagag aggaatccgg ggaaggccag cttggcaggt    1500
gaatgtcatc cgaacacagg gatgagctgg tgagcagtgt gg                       1542
```

<210> SEQ ID NO 5
<211> LENGTH: 1257
<212> TYPE: DNA
<213> ORGANISM: Mus musculus

<400> SEQUENCE: 5

```
ttttactgtc cttgagaatg gagaggatca gcaaagctgg aagccctcca ggctcatttc      60
agagagaata ttccacagag cttgaaggcg cgggatctgg gccgatgatg gaagctttct     120
ctaagtctgc attccaaaag ctcagacaga gagatggaaa tcaagagggg aagagctacc     180
tcagatatac caaaatgaag actgccacca acatctacat tttcaacctt gctctggcag     240
atgccttagc cactagcacg ctgcccttc agagtgttaa ctacctgatg gaacgtggc      300 cctttggaaa catcctctgc aagatcgtga tctcaataga ctactacaac atgttcacca     360
gtatcttcac cctctgcacc atgagtgtag accgctacat tgccgtctgc cacccggtca     420
aggccctgga tttccgtacc ccccgaaatg ccaaaattgt caatgtctgc aactggatcc     480
tctcttctgc cattggtctg cccgtaatgt tcatggcaac cacaaaatac aggcaggggt     540
ccatagattg caccctcacg ttctctcatc ccacatggta ctgggagaac ctgctcaaaa     600
tctgtgtctt catcttcgcc ttcatcatgc cggtcctcat catcactgtg tgttatggac     660
tgatgatctt acgactcaag agtgtccgca tgctgtcggg ctccaaagaa aaggacagga     720
acctgcgcag gatcacccgg atggtgctgg tggtcgtggc tgtatttatt gtctgctgga     780
cccccatcca catctatgtc atcatcaaag cactgatcac gattccagaa accactttcc     840
agactgtttc ctggcacttc tgcattgcct tgggttacac aaacagctgc ctgaacccag     900
ttctttatgc gttcctggat gaaaacttca acgatgttt tagagagttc tgcatcccaa      960
cttcctccac aatcgaacag caaaactctg ctcgaatccg tcaaaacact agggaacacc    1020
cctccacggc taatacagtg gatcgaacta accaccagcc aaccctggca gtcagcgtgg    1080
cccagatctt tacaggatat ccttctccga ctcatgttga aaaccctgc aagagttgca    1140 tggacagagg aatgaggaac cttcttcctg atgatggcc aagagaggaa tccggggaag    1200
gccagcttgg caggtgaatg tcatccgaac acagggatga gctggtgagc agtgtgg       1257
```

<210> SEQ ID NO 6
<211> LENGTH: 139
<212> TYPE: DNA
<213> ORGANISM: Mus musculus

<400> SEQUENCE: 6

```
ggaaatcaag aggggaagag ttacctcagg tcttgtgcag gtgcctgctg ctgtgaattc      60
atgaagacaa caccctcccc tttagaagac agtgcttcac aacactccca actagcctct    120
ggctctgatg ttccactt                                                     139
```

<210> SEQ ID NO 7

<211> LENGTH: 361
<212> TYPE: DNA
<213> ORGANISM: Mus musculus

<400> SEQUENCE: 7

```
cctccaggct catttcagag agaatattcc acagagcttg aaggcgcggg atctgggccg      60
atgatggaag ctttctctaa gtctgcattc caaaagctca gacagagaga tggaaatcaa     120
gaggggaaga gttacctcag gtcttgtgca ggtgcactgc tgctgtgaat tcatgaagac     180
aacaccctcc cctttagaag acagtgcttc acaacactcc caactagcct ctggctctga     240
tgttcacttt gtcccctctt ctgaagcagg gcttgtcctt gtaagaaact gaggagccta     300
gggcagctgt gagaggaaga ggctggggca cctggaaccc gaacactctt gagtgctctc     360
t                                                                     361
```

<210> SEQ ID NO 8
<211> LENGTH: 268
<212> TYPE: DNA
<213> ORGANISM: Mus musculus

<400> SEQUENCE: 8

```
attccaaaag ctcagacaga gagatggaag tcaagagggg aagagttacc tcaggtcttg      60
tgcaggtgca ctgctgctgt gaattcatga agacaacacc ctccccttta gtagacagcg     120
cttcacaaca ctcccaacta gcctctggct ctgatgttca ctttgtcccc tcttctgaag     180
cagatgtacc aaaatgaaga ctgccaccaa catctacatt tcaaccttg ctctggcaga      240
tgccttagcc actagcacgc tgcccaag                                        268
```

<210> SEQ ID NO 9
<211> LENGTH: 1729
<212> TYPE: DNA
<213> ORGANISM: Mus musculus

<400> SEQUENCE: 9

```
ggaacccgaa cactcttgag tgctctcagt tacagcctac cgagtccgca gcaagcattc      60
agaaccatgg acagcagcgc cggcccaggg aacatcagcg actgctctga ccccttagct     120
cctgcaagtt gctccccagc acctggctcc tggctcaact tgtcccacgt tgatggcaac     180
cagtccgacc catgcggtcc taaccgcacg gggcttggcg ggagccacag cctgtgccct     240
cagaccggca gccttccat ggtcacagcc atcaccatca tggccctcta ttctatcgtg      300
tgtgtagtgg gcctctttgg aaacttcctg gtcatgtatg tgattgtaag ataccaaaa     360
atgaagactg ccaccaacat ctacattttc aaccttgctc tggcagatgc cttagccact     420
agcacgctgc cctttcagag tgttaactac ctgatgggaa cgtggccctt ggaaacatc      480
ctctgcaaga tcgtgatctc aatagactac tacaacatgt tcaccagtat cttcaccctc     540
tgcaccatga gtgtagaccg ctacattgcc gtctgccacc cggtcaaggc cctggatttc     600
cgtacccccc gaaatgccaa aattgtcaat gtctgcaact ggatcctctc ttctgccatt     660
ggtctgcccg taatgttcat ggcaaccaca aaatacaggc agggtccat agattgcacc     720
ctcacgttct ctcatcccac atggtactgg gagaacctgc tcaaaatctg tgtcttcatc     780
ttcgccttca tcatgccggt cctcatcatc actgtgtgtt atggactgat gatcttacga     840
ctcaagagtg tccgcatgct gtcgggctcc aaagaaaagg acaggaacct gcgcaggatc     900
acccggatgg tgctggtggt cgtggctgta tttattgtct gctggacccc catccacatc     960
tatgtcatca tcaaagcact gatcacgatt ccagaaacca ctttccagac tgtttcctgg    1020
```

```
cacttctgca ttgccttggg ttacacaaac agctgcctga acccagttct ttatgcgttc    1080
ctggatgaaa acttcaaacg atgttttaga gagttctgca tcccaacttc ctccacaatc    1140
gaacagcaaa actctgctcg aatccgtcaa aacactaggg aacacccctc cacggctaat    1200
acagtggatc gaactaacca ccaggcacca tgtgcatgcg tgcctggagc aacagaggt     1260 caaacgaagg catcagatct tctggatctg gaattggaga cagttgggag ccaccaggca    1320
gatgctgaaa ccaacccagg tccttacgaa ggcagcaagt gcgctgaacc actagccatc    1380
tctctggtcc cgctatatta gcattgtgct aagaaaaagc tggactccca gagagggtgt    1440
gtacagcatc cagtgtgacc tgtcccttgt ctttgagcct gggggccatc ttctttcaca    1500
gcataccatt tccttgtatc ctctctgaag ccaaccctgg cagtcagcgt ggcccagatc    1560
tttacaggat atccttctcc gactcatgtt gaaaaccct gcaagagttg catggacaga     1620
ggaatgagga accttcttcc tgatgatggc ccaagacagg aatccgggga aggccagctt    1680
ggcaggtgaa tgtcatccga acacagggat gagctggtga gcagtgtgg               1729
```

<210> SEQ ID NO 10
<211> LENGTH: 2045
<212> TYPE: DNA
<213> ORGANISM: Mus musculus

<400> SEQUENCE: 10

```
ggaacccgaa cactcttgag tgctctcagt tacagcctac cgagtccgca gcaagcattc      60
agaaccatgg acagcagcgc cggcccaggg aacatcagcg actgctctga ccccttagct    120
cctgcaagtt gctccccagc acctggctcc tggctcaact tgtcccacgt tgatggcaac    180
cagtccgacc catgcggtcc taaccgcacg gggcttggcg ggagccacag cctgtgccct    240
cagaccggca gccttccat ggtcacagcc atcaccatca tggccctcta ttctatcgtg     300
tgtgtagtgg gcctctttgg aaacttcctg gtcatgtatg tgattgtaag atataccaaa    360
atgaagactg ccaccaacat ctacattttc aaccttgctc tggcagatgc cttagccact    420
agcacgctgc cctttcagag tgttaactac ctgatgggaa cgtggccctt tggaaacatc    480
ctctgcaaga tcgtgatctc aatagactac tacaacatgt tcaccagtat cttcacccct    540
tgcaccatga gtgtagaccg ctacattgcc gtctgccacc cggtcaaggc cctggatttc    600 cgtaccccc gaaatgccaa aattgtcaat gtctgcaact ggatcctctc ttctgccatt    660
ggtctgcccg taatgttcat ggcaaccaca aaatacaggc agggggtccat agattgcacc    720 ctcacgttct ctcatcccac atggtactgg gagaacctgc tcaaaatctg tgtcttcatc    780
ttcgccttca tcatgccggt cctcatcatc actgtgtgtt atggactgat gatcttacga    840
ctcaagagtg tccgcatgct gtcgggctcc aaagaaaagg acaggaacct gcgcaggatc    900
acccggatgg tgctggtggt cgtggctgta tttattgtct gctggacccc catccacatc    960
tatgtcatca tcaaagcact gatcacgatt ccagaaacca ctttccagac tgtttcctgg   1020
cacttctgca ttgccttggg ttacacaaac agctgcctga acccagttct ttatgcgttc   1080
ctggatgaaa acttcaaacg atgttttaga gagttctgca tcccaacttc ctccacaatc   1140
gaacagcaaa actctgctcg aatccgtcaa aacactaggg aacacccctc cacggctaat   1200
acagtggatc gaactaacca ccagaagctt ttaatgtgga gagctatgcc tacattcaag   1260
agacacttgg ctatcatgtt aagccttgat aattagggca ccaaagggga caagtgtcaa   1320
atcaagatgc tgttttttgtt tttgttttttt gtttttttgtt ttttctggtt ccatcaagtt   1380
```

-continued

| | |
|---|---|
| cttgtagaac actattatgg ttagcaatgc tcaatagaca atgtcagggg gtgtgacata | 1440 |
| ttttagatgt agaagcacta cactgtccca actccatagt tggaagagca cctcgtacta | 1500 |
| tcaggcttga caagtcccct gcaggccacc aggcccaaag ctgtgaattg agccgtggtt | 1560 |
| taaacctgta tgaaaataag tagcaatgtc tcagaattca agaaattcag aattctaaaa | 1620 |
| ctgattgtta atctctcact cccatgcatt caaatgtgtc ctgaatacat ccacagacac | 1680 |
| acaaaatact aaaactctct ctggaagcag agcttgtgct tcgtttgggt ttcattttct | 1740 |
| ttgtttgttt gtttgtttgt ttgtttgttt tgctttgttt gaagcctacc gctttctggc | 1800 |
| tataattatg agaaggcact ctgtcagcct tagggtatgt ttttctctaa ttaaattgca | 1860 |
| tgttgctaag tgttaggctt gtaaatgaca cgttcttttg ttttgaatac aatatgtttg | 1920 |
| cagaaaatag atttattttg aaaaggcata tacacagaac tgggagaagc acaccaaaga | 1980 |
| tattttgtta ccatatggca aatgtaacca tagagagcag agtacctaat gctggtgcca | 2040 |
| acccc | 2045 |

<210> SEQ ID NO 11
<211> LENGTH: 1365
<212> TYPE: DNA
<213> ORGANISM: Mus musculus

<400> SEQUENCE: 11

| | |
|---|---|
| ggaacccgaa cactcttgag tgctctcagt tacagcctac cgagtccgca gcaagcattc | 60 |
| agaaccatgg acagcagcgc cggcccaggg aacatcagcg actgctctga ccccttagct | 120 |
| cctgcaagtt gctccccagc acctggctcc tggctcaact tgtcccacgt tgatggcaac | 180 |
| cagtccgacc catgcggtcc taaccgcacg gggcttggcg ggagccacag cctgtgccct | 240 |
| cagaccggca gcccttccat ggtcacagcc atcaccatca tggccctcta ttctatcgtg | 300 |
| tgtgtagtgg gcctctttgg aaacttcctg gtcatgtatg tgattgtaag ataccaaa | 360 |
| atgaagactg ccaccaacat ctacattttc aaccttgctc tggcagatgc cttagccact | 420 |
| agcacgctgc cctttcagag tgttaactac ctgatgggaa cgtggccctt tggaaacatc | 480 |
| ctctgcaaga tcgtgatctc aatagactac tacaacatgt tcaccagtat cttcacccct | 540 |
| tgcaccatga gtgtagaccg ctacattgcc gtctgccacc cggtcaaggc cctggatttc | 600 |
| cgtaccccc gaaatgccaa aattgtcaat gtctgcaact ggatcctctc ttctgccatt | 660 |
| ggtctgcccg taatgttcat ggcaaccaca aaatacaggc aggggtccat agattgcacc | 720 |
| ctcacgttct ctcatcccac atggtactgg gagaacctgc tcaaaatctg tgtcttcatc | 780 |
| ttcgccttca tcatgccggt cctcatcatc actgtgtgtt atggactgat gatcttacga | 840 |
| ctcaagagtg tccgcatgct gtcgggctcc aaagaaaagg acaggaacct gcgcaggatc | 900 |
| acccggatgg tgctggtggt cgtggctgta tttattgtct gctggacccc catccacatc | 960 |
| tatgtcatca tcaaagcact gatcacgatt ccagaaacca ctttccagac tgtttcctgg | 1020 |
| cacttctgca ttgccttggg ttacacaaac agctgcctga cccagttct ttatgcgttc | 1080 |
| ctggatgaaa acttcaaacg atgttttaga gagttctgca tcccaacttc ctccacaatc | 1140 |
| gaacagcaaa actctgctcg aatccgtcaa aacactaggg aacaccccctc cacggctaat | 1200 |
| acagtggatc gaactaacca ccaggtatgt gctttctaga attatgtata acatataaaa | 1260 |
| acacagcacc tgataccagt ctaagattta gatccttaag gaggtcggtt actggagaat | 1320 |
| ccagccaagc ctaaaaatag agagggagta ggggaccaaa ttctg | 1365 |

<210> SEQ ID NO 12
<211> LENGTH: 1346
<212> TYPE: DNA
<213> ORGANISM: Mus musculus

<400> SEQUENCE: 12

| | | | | | |
|---|---|---|---|---|---|
| ggaacccgaa | cactcttgag | tgctctcagt | tacagcctac | cgagtccgca | gcaagcattc | 60 |
| agaaccatgg | acagcagcgc | cggcccaggg | aacatcagcg | actgctctga | ccccttagct | 120 |
| cctgcaagtt | gctccccagc | acctggctcc | tggctcaact | tgtcccacgt | tgatggcaac | 180 |
| cagtccgacc | catgcggtcc | taaccgcacg | gggcttggcg | ggagccacag | cctgtgccct | 240 |
| cagaccggca | gccctthccat | ggtcacagcc | atcaccatca | tggccctcta | ttctatcgtg | 300 |
| tgtgtagtgg | gcctctttgg | aaacttcctg | gtcatgtatg | tgattgtaag | atataccaaa | 360 |
| atgaagactg | ccaccaacat | ctacattttc | aaccttgctc | tggcagatgc | cttagccact | 420 |
| agcacgctgc | cctttcagag | tgttaactac | ctgatgggaa | cgtggccctt | tggaaacatc | 480 |
| ctctgcaaga | tcgtgatctc | aatagactac | tacaacatgt | tcaccagtat | cttcaccctc | 540 |
| tgcaccatga | gtgtagaccg | ctacattgcc | gtctgccacc | cggtcaaggc | cctggatttc | 600 |
| cgtacccccc | gaaatgccaa | aattgtcaat | gtctgcaact | ggatcctctc | ttctgccatt | 660 |
| ggtctgcccg | taatgttcat | ggcaaccaca | aaatacaggc | aggggtccat | agattgcacc | 720 |
| ctcacgttct | ctcatcccac | atggtactgg | gagaacctgc | tcaaaatctg | tgtcttcatc | 780 |
| ttcgccttca | tcatgccggt | cctcatcatc | actgtgtgtt | atggactgat | gatcttacga | 840 |
| ctcaagagtg | tccgcatgct | gtcgggctcc | aaagaaaagg | acaggaacct | gcgcaggatc | 900 |
| acccggatgg | tgctggtggt | ccgtggctgt | atttattgtc | tgctggaccc | catccacatc | 960 |
| tatgtcatca | tcaaagcact | gatcacgatt | ccagaaacca | ctttccagac | tgtttcctgg | 1020 |
| cacttctgca | ttgccttggg | ttacacaaac | agctgcctga | acccagttct | ttatgcgttc | 1080 |
| ctggatgaaa | acttcaaacg | atgttttaga | gagttctgca | tcccaacttc | ctccacaatc | 1140 |
| gaacagcaaa | actctgctcg | aatccgtcaa | aacactaggg | aacaccccetc | cacggctaat | 1200 |
| acagtggatc | gaactaacca | ccagaaaata | gatttatttt | gaaaaggcat | atacacagaa | 1260 |
| ctgggagaag | cacaccaaag | atattttgtt | accatatggc | aaatgtaacc | atagagagca | 1320 |
| gagtacctaa | tgctggtgcc | aaccc |  |  |  | 1346 |

<210> SEQ ID NO 13
<211> LENGTH: 193
<212> TYPE: DNA
<213> ORGANISM: Mus musculus

<400> SEQUENCE: 13

| | | | | | |
|---|---|---|---|---|---|
| gggaacaccc | ctccacggct | aatacagtgg | atcgaactaa | ccaccagtgt | gtatgagtgc | 60 |
| tatgcccaca | gggaccagaa | gatggtatca | gaccttctag | aactgaagta | gtgagcagtc | 120 |
| cccacccca | cccccgcaa | taaaatagat | ttattttgaa | aaggcatata | cacagaactg | 180 |
| ggagaagcac | acc |  |  |  |  | 193 |

<210> SEQ ID NO 14
<211> LENGTH: 715
<212> TYPE: DNA
<213> ORGANISM: Mus musculus

<400> SEQUENCE: 14

| | | | | | |
|---|---|---|---|---|---|
| gggaacaccc | ctccacggct | aatacagtgg | atcgaactaa | ccaccaggag | cctcagtcag | 60 |

-continued

| | | | |
|---|---|---|---|
| cggagacatg | atgtgaatga | acggactgat | tagacaaggt | ttcctgaaca | ctgagataca | 120 |
| aaacaaatag | agagcttact | agagaaaatt | cgtagcccga | aaattcaatt | atagaaacaa | 180 |
| atgagtgtta | gagtagatat | ggtaaggcct | cagagaggtt | ttatttcacg | actaacaaca | 240 |
| tgacccaagg | cacctaatcc | atggtgatta | gattacaaag | acaattctag | tgcctgggcc | 300 |
| agagaaatgt | ttgtctccca | cagacaagcc | tcacacttca | gtaatgaaat | gagtaaatta | 360 |
| aatcggtgag | caagatggtg | ggaggagtca | aaatattttc | atgccttcct | gtggaactcc | 420 |
| aaaggaagac | caaacacagtc | aactaacctg | gctcttggtg | gctctcagag | ctgaacaacc | 480 |
| aaccaaagag | cactcatgag | ctagacctag | gcctctttta | cacgtgtagc | agatgtgcgt | 540 |
| ctccatcttc | atgtgggtcc | ccccaacaag | taaagtagca | gctgtctcta | aagctgttgc | 600 |
| ctgtctggct | tcggtggaag | aagatgtgat | tcgcttaacc | ctgaagtgac | ttgatatgca | 660 |
| gggaaaatag | atttattttg | aaaaggcata | tacacagaac | tgggagaagc | acacc | 715 |

<210> SEQ ID NO 15
<211> LENGTH: 124
<212> TYPE: DNA
<213> ORGANISM: Homo sapiens

<400> SEQUENCE: 15

| | | | |
|---|---|---|---|
| ggatagaact | aatcatcagt | gcctacctat | accttccctg | tcttgctggg | ctctagagca | 60 |
| tggccgcttg | gttgtgtacc | ctggaccact | gcaaggacct | cttgtcagat | atgacctccc | 120 |
| agct | | | | | | 124 |

<210> SEQ ID NO 16
<211> LENGTH: 1610
<212> TYPE: DNA
<213> ORGANISM: Mus musculus

<400> SEQUENCE: 16

| | | | |
|---|---|---|---|
| gctccctccc | ttccactcag | agagtggcgc | tttggggatg | ctaaggatgc | gcctccgtgt | 60 |
| acttctaagg | tgggagggg | ctacaagcag | aggagaatat | cggacgctca | gacgttccat | 120 |
| tctgcctgcc | gctcttctct | ggttccacta | gggcttgtcc | ttgtaagaaa | ctgacggagc | 180 |
| ctagggcagc | tgtgagagga | agaggctggg | gcgcctggaa | cccgaacact | cttgagtgct | 240 |
| ctcagttaca | gcctaccgag | tccgcagcaa | gcattcagaa | ccatggacag | cagcgccggc | 300 |
| ccagggaaca | tcagcgactg | ctctgacccc | ttagctcctg | caagttgctc | cccagcacct | 360 |
| ggctcctggc | tcaacttgtc | ccacgttgat | ggcaaccagt | ccgacccatg | cggtcctaac | 420 |
| cgcacggggc | ttggcgggag | ccacagcctg | tgccctcaga | ccggcagccc | ttccatggtc | 480 |
| acagccatca | ccatcatggc | cctctattct | atcgtgtgtg | tagtgggcct | cttttggaaac | 540 |
| ttcctggtca | tgtatgtgat | tgtaagatat | accaaaatga | agactgccac | caacatctac | 600 |
| attttcaacc | ttgctctggc | agatgcctta | gccactagca | cgctgccctt | tcagagtgtt | 660 |
| aactacctga | tgggaacgtg | gccctttgga | aacatcctct | gcaagatcgt | gatctcaata | 720 |
| gactactaca | acatgttcac | cagtatcttc | accctctgca | ccatgagtgt | agaccgctac | 780 |
| attgccgtct | gccaccccgt | caaggcctg | gatttccgta | cccccgaaa | tgccaaaatt | 840 |
| gtcaatgtct | gcaactggat | cctctcttct | gccattggtc | tgcccgtaat | gttcatggca | 900 |
| accacaaaat | acaggcaggg | gtccatagat | tgcaccctca | cgttctctca | tcccacatgg | 960 |
| tactgggaga | acctgctcaa | aatctgtgtc | ttcatcttcg | ccttcatcat | gccggtcctc | 1020 |
| atcatcactg | tgtgttatgg | actgatgatc | ttacgactca | agagtgtccg | catgctgtcg | 1080 |

```
ggctccaaag aaaaggacag gaacctgcgc aggatcaccc ggatggtgct ggtggtcgtg   1140
gctgtattta ttgtctgctg acccccatc cacatctatg tcatcatcaa agcactgatc    1200
acgattccag aaaccacttt ccagactgtt tcctggcact ctgcattgc cttgggttac    1260 acaaacagct gcctgaaccc agttctttat gcgttcctgg atgaaaactt caaacgatgt   1320
tttagagagt tctgcatccc aacttcctcc acaatcgaac agcaaaactc tgctcgaatc   1380
cgtcaaaaca ctagggaaca cccctccacg gctaatacag tggatcgaac taaccaccag   1440
ctagaaaatc tggaagcaga aactgctcca ttgcccctaac tgggtcccac gccatccaga  1500
ccctcgctaa acttagaggc tgccatctac ttggaatcag gttgctgtca gggtttgtgg   1560
gaggctctgg tttcctggaa aagcatctga tcctgcattc aaagtcattc              1610
```

<210> SEQ ID NO 17
<211> LENGTH: 438
<212> TYPE: PRT
<213> ORGANISM: Mus musculus

<400> SEQUENCE: 17

```
Met Asp Ser Ser Ala Gly Pro Gly Asn Ile Ser Asp Cys Ser Asp Pro
1               5                   10                  15

Leu Ala Pro Ala Ser Cys Ser Pro Ala Pro Gly Ser Trp Leu Asn Leu
            20                  25                  30

Ser His Val Asp Gly Asn Gln Ser Asp Pro Cys Gly Pro Asn Arg Thr
        35                  40                  45

Gly Leu Gly Gly Ser His Ser Leu Cys Pro Gln Thr Gly Ser Pro Ser
    50                  55                  60

Met Val Thr Ala Ile Thr Ile Met Ala Leu Tyr Ser Ile Val Cys Val
65                  70                  75                  80

Val Gly Leu Phe Gly Asn Phe Leu Val Met Tyr Val Ile Val Arg Tyr
                85                  90                  95

Thr Lys Met Lys Thr Ala Thr Asn Ile Tyr Ile Phe Asn Leu Ala Leu
            100                 105                 110

Ala Asp Ala Leu Ala Thr Ser Thr Leu Pro Phe Gln Ser Val Asn Tyr
        115                 120                 125

Leu Met Gly Thr Trp Pro Phe Gly Asn Ile Leu Cys Lys Ile Val Ile
    130                 135                 140

Ser Ile Asp Tyr Tyr Asn Met Phe Thr Ser Ile Phe Thr Leu Cys Thr
145                 150                 155                 160

Met Ser Val Asp Arg Tyr Ile Ala Val Cys His Pro Val Lys Ala Leu
                165                 170                 175

Asp Phe Arg Thr Pro Arg Asn Ala Lys Ile Val Asn Val Cys Asn Trp
            180                 185                 190

Ile Leu Ser Ser Ala Ile Gly Leu Pro Val Met Phe Met Ala Thr Thr
        195                 200                 205

Lys Tyr Arg Gln Gly Ser Ile Asp Cys Thr Leu Thr Phe Ser His Pro
    210                 215                 220

Thr Trp Tyr Trp Glu Asn Leu Leu Lys Ile Cys Val Phe Ile Phe Ala
225                 230                 235                 240

Phe Ile Met Pro Val Leu Ile Ile Thr Val Cys Tyr Gly Leu Met Ile
                245                 250                 255

Leu Arg Leu Lys Ser Val Arg Met Leu Ser Gly Ser Lys Glu Lys Asp
            260                 265                 270

Arg Asn Leu Arg Arg Ile Thr Arg Met Val Leu Val Val Val Ala Val
```

-continued

```
                275                 280                 285
Phe Ile Val Cys Trp Thr Pro Ile His Ile Tyr Val Ile Ile Lys Ala
    290                 295                 300
Leu Ile Thr Ile Pro Glu Thr Thr Phe Gln Thr Val Ser Trp His Phe
305                 310                 315                 320
Cys Ile Ala Leu Gly Tyr Thr Asn Ser Cys Leu Asn Pro Val Leu Tyr
                325                 330                 335
Ala Phe Leu Asp Glu Asn Phe Lys Arg Cys Phe Arg Glu Phe Cys Ile
                340                 345                 350
Pro Thr Ser Ser Thr Ile Glu Gln Gln Asn Ser Ala Arg Ile Arg Gln
                355                 360                 365
Asn Thr Arg Glu His Pro Ser Thr Ala Asn Thr Val Asp Arg Thr Asn
    370                 375                 380
His Gln Pro Thr Leu Ala Val Ser Val Ala Gln Ile Phe Thr Gly Tyr
385                 390                 395                 400
Pro Ser Pro Thr His Val Glu Lys Pro Cys Lys Ser Cys Met Asp Arg
                405                 410                 415
Gly Met Arg Asn Leu Leu Pro Asp Asp Gly Pro Arg Gln Glu Ser Gly
                420                 425                 430
Glu Gly Gln Leu Gly Arg
                435

<210> SEQ ID NO 18
<211> LENGTH: 359
<212> TYPE: PRT
<213> ORGANISM: Mus musculus

<400> SEQUENCE: 18

Met Glu Arg Ile Ser Lys Ala Gly Ser Pro Pro Gly Ser Phe Gln Arg
1               5                   10                  15
Glu Tyr Ser Thr Glu Leu Glu Gly Ala Gly Ser Gly Pro Met Met Glu
                20                  25                  30
Ala Phe Ser Lys Ser Ala Phe Gln Lys Leu Arg Gln Arg Asp Gly Asn
            35                  40                  45
Gln Glu Gly Lys Ser Tyr Leu Arg Tyr Thr Lys Met Lys Thr Ala Thr
    50                  55                  60
Asn Ile Tyr Ile Phe Asn Leu Ala Leu Ala Asp Ala Leu Ala Thr Ser
65                  70                  75                  80
Thr Leu Pro Phe Gln Ser Val Asn Tyr Leu Met Gly Thr Trp Pro Phe
                85                  90                  95
Gly Asn Ile Leu Cys Lys Ile Val Ile Ser Ile Asp Tyr Tyr Asn Met
            100                 105                 110
Phe Thr Ser Ile Phe Thr Leu Cys Thr Met Ser Val Asp Arg Tyr Ile
        115                 120                 125
Ala Val Cys His Pro Val Lys Ala Leu Asp Phe Arg Thr Pro Arg Asn
    130                 135                 140
Ala Lys Ile Val Asn Val Cys Asn Trp Ile Leu Ser Ser Ala Ile Gly
145                 150                 155                 160
Leu Pro Val Met Phe Met Ala Thr Thr Lys Tyr Arg Gln Gly Ser Ile
                165                 170                 175
Asp Cys Thr Leu Thr Phe Ser His Pro Thr Trp Tyr Trp Glu Asn Leu
            180                 185                 190
Leu Lys Ile Cys Val Phe Ile Phe Ala Phe Ile Met Pro Val Leu Ile
        195                 200                 205
```

```
Ile Thr Val Cys Tyr Gly Leu Met Ile Leu Arg Leu Lys Ser Val Arg
            210                 215                 220

Met Leu Ser Gly Ser Lys Glu Lys Asp Arg Asn Leu Arg Arg Ile Thr
225                 230                 235                 240

Arg Met Val Leu Val Val Ala Val Phe Ile Val Cys Trp Thr Pro
                245                 250                 255

Ile His Ile Tyr Val Ile Ile Lys Ala Leu Ile Thr Ile Pro Glu Thr
            260                 265                 270

Thr Phe Gln Thr Val Ser Trp His Phe Cys Ile Ala Leu Gly Tyr Thr
            275                 280                 285

Asn Ser Cys Leu Asn Pro Val Leu Tyr Ala Phe Leu Asp Glu Asn Phe
290                 295                 300

Lys Arg Cys Phe Arg Glu Phe Cys Ile Pro Thr Ser Ser Thr Ile Glu
305                 310                 315                 320

Gln Gln Asn Ser Ala Arg Ile Arg Gln Asn Thr Arg Glu His Pro Ser
            325                 330                 335

Thr Ala Asn Thr Val Asp Arg Thr Asn His Gln Leu Glu Asn Leu Glu
            340                 345                 350

Ala Glu Thr Ala Pro Leu Pro
            355

<210> SEQ ID NO 19
<211> LENGTH: 392
<212> TYPE: PRT
<213> ORGANISM: Mus musculus

<400> SEQUENCE: 19

Met Asp Ser Ser Ala Gly Pro Gly Asn Ile Ser Asp Cys Ser Asp Pro
1               5                   10                  15

Leu Ala Pro Ala Ser Cys Ser Pro Ala Pro Gly Ser Trp Leu Asn Leu
                20                  25                  30

Ser His Val Asp Gly Asn Gln Ser Asp Pro Cys Gly Pro Asn Arg Thr
            35                  40                  45

Gly Leu Gly Gly Ser His Ser Leu Cys Pro Gln Thr Gly Ser Pro Ser
    50                  55                  60

Met Val Thr Ala Ile Thr Ile Met Ala Leu Tyr Ser Ile Val Cys Val
65                  70                  75                  80

Val Gly Leu Phe Gly Asn Phe Leu Val Met Tyr Val Ile Val Arg Tyr
                85                  90                  95

Thr Lys Met Lys Thr Ala Thr Asn Ile Tyr Ile Phe Asn Leu Ala Leu
                100                 105                 110

Ala Asp Ala Leu Ala Thr Ser Thr Leu Pro Phe Gln Ser Val Asn Tyr
            115                 120                 125

Leu Met Gly Thr Trp Pro Phe Gly Asn Ile Leu Cys Lys Ile Val Ile
130                 135                 140

Ser Ile Asp Tyr Tyr Asn Met Phe Thr Ser Ile Phe Thr Leu Cys Thr
145                 150                 155                 160

Met Ser Val Asp Arg Tyr Ile Ala Val Cys His Pro Val Lys Ala Leu
                165                 170                 175

Asp Phe Arg Thr Pro Arg Asn Ala Lys Ile Val Asn Val Cys Asn Trp
            180                 185                 190

Ile Leu Ser Ser Ala Ile Gly Leu Pro Val Met Phe Met Ala Thr Thr
            195                 200                 205

Lys Tyr Arg Gln Gly Ser Ile Asp Cys Thr Leu Thr Phe Ser His Pro
210                 215                 220
```

```
Thr Trp Tyr Trp Glu Asn Leu Leu Lys Ile Cys Val Phe Ile Phe Ala
225                 230                 235                 240

Phe Ile Met Pro Val Leu Ile Ile Thr Val Cys Tyr Gly Leu Met Ile
            245                 250                 255

Leu Arg Leu Lys Ser Val Arg Met Leu Ser Gly Ser Lys Glu Lys Asp
            260                 265                 270

Arg Asn Leu Arg Arg Ile Thr Arg Met Val Leu Val Val Ala Val
        275                 280                 285

Phe Ile Val Cys Trp Thr Pro Ile His Ile Tyr Val Ile Ile Lys Ala
    290                 295                 300

Leu Ile Thr Ile Pro Glu Thr Thr Phe Gln Thr Val Ser Trp His Phe
305                 310                 315                 320

Cys Ile Ala Leu Gly Tyr Thr Asn Ser Cys Leu Asn Pro Val Leu Tyr
                325                 330                 335

Ala Phe Leu Asp Glu Asn Phe Lys Arg Cys Phe Arg Glu Phe Cys Ile
            340                 345                 350

Pro Thr Ser Ser Thr Ile Glu Gln Gln Asn Ser Ala Arg Ile Arg Gln
            355                 360                 365

Asn Thr Arg Glu His Pro Ser Thr Ala Asn Thr Val Asp Arg Thr Asn
        370                 375                 380

His Gln Arg Asn Glu Glu Pro Ser
385                 390

<210> SEQ ID NO 20
<211> LENGTH: 401
<212> TYPE: PRT
<213> ORGANISM: Mus musculus

<400> SEQUENCE: 20

Met Asp Ser Ser Ala Gly Pro Gly Asn Ile Ser Asp Cys Ser Asp Pro
1               5                   10                  15

Leu Ala Pro Ala Ser Cys Ser Pro Ala Pro Gly Ser Trp Leu Asn Leu
            20                  25                  30

Ser His Val Asp Gly Asn Gln Ser Asp Pro Cys Gly Pro Asn Arg Thr
        35                  40                  45

Gly Leu Gly Gly Ser His Ser Leu Cys Pro Gln Thr Gly Ser Pro Ser
    50                  55                  60

Met Val Thr Ala Ile Thr Ile Met Ala Leu Tyr Ser Ile Val Cys Val
65                  70                  75                  80

Val Gly Leu Phe Gly Asn Phe Leu Val Met Tyr Val Ile Val Arg Tyr
                85                  90                  95

Thr Lys Met Lys Thr Ala Thr Asn Ile Tyr Ile Phe Asn Leu Ala Leu
            100                 105                 110

Ala Asp Ala Leu Ala Thr Ser Thr Leu Pro Phe Gln Ser Val Asn Tyr
        115                 120                 125

Leu Met Gly Thr Trp Pro Phe Gly Asn Ile Leu Cys Lys Ile Val Ile
    130                 135                 140

Ser Ile Asp Tyr Tyr Asn Met Phe Thr Ser Ile Phe Thr Leu Cys Thr
145                 150                 155                 160

Met Ser Val Asp Arg Tyr Ile Ala Val Cys His Pro Val Lys Ala Leu
                165                 170                 175

Asp Phe Arg Thr Pro Arg Asn Ala Lys Ile Val Asn Val Cys Asn Trp
            180                 185                 190

Ile Leu Ser Ser Ala Ile Gly Leu Pro Val Met Phe Met Ala Thr Thr
```

-continued

```
            195                 200                 205
Lys Tyr Arg Gln Gly Ser Ile Asp Cys Thr Leu Thr Phe Ser His Pro
210                 215                 220

Thr Trp Tyr Trp Glu Asn Leu Leu Lys Ile Cys Val Phe Ile Phe Ala
225                 230                 235                 240

Phe Ile Met Pro Val Leu Ile Ile Thr Val Cys Tyr Gly Leu Met Ile
                245                 250                 255

Leu Arg Leu Lys Ser Val Arg Met Leu Ser Gly Ser Lys Glu Lys Asp
                260                 265                 270

Arg Asn Leu Arg Arg Ile Thr Arg Met Val Leu Val Val Ala Val
                275                 280                 285

Phe Ile Val Cys Trp Thr Pro Ile His Ile Tyr Val Ile Ile Lys Ala
290                 295                 300

Leu Ile Thr Ile Pro Glu Thr Thr Phe Gln Thr Val Ser Trp His Phe
305                 310                 315                 320

Cys Ile Ala Leu Gly Tyr Thr Asn Ser Cys Leu Asn Pro Val Leu Tyr
                325                 330                 335

Ala Phe Leu Asp Glu Asn Phe Lys Arg Cys Phe Arg Glu Phe Cys Ile
                340                 345                 350

Pro Thr Ser Ser Thr Ile Glu Gln Gln Asn Ser Ala Arg Ile Arg Gln
                355                 360                 365

Asn Thr Arg Glu His Pro Ser Thr Ala Asn Thr Val Asp Arg Thr Asn
                370                 375                 380

His Gln Lys Lys Lys Leu Asp Ser Gln Arg Gly Cys Val Gln His Pro
385                 390                 395                 400

Val

<210> SEQ ID NO 21
<211> LENGTH: 399
<212> TYPE: PRT
<213> ORGANISM: Mus musculus

<400> SEQUENCE: 21

Met Glu Arg Ile Ser Lys Ala Gly Ser Pro Pro Gly Ser Phe Gln Arg
1               5                   10                  15

Glu Tyr Ser Thr Glu Leu Glu Gly Ala Gly Ser Gly Pro Met Met Glu
                20                  25                  30

Ala Phe Ser Lys Ser Ala Phe Gln Lys Leu Arg Gln Arg Asp Gly Asn
                35                  40                  45

Gln Glu Gly Lys Ser Tyr Leu Arg Tyr Thr Lys Met Lys Thr Ala Thr
50                  55                  60

Asn Ile Tyr Ile Phe Asn Leu Ala Leu Ala Asp Ala Leu Ala Thr Ser
65                  70                  75                  80

Thr Leu Pro Phe Gln Ser Val Asn Tyr Leu Met Gly Thr Trp Pro Phe
                85                  90                  95

Gly Asn Ile Leu Cys Lys Ile Val Ile Ser Ile Asp Tyr Tyr Asn Met
                100                 105                 110

Phe Thr Ser Ile Phe Thr Leu Cys Thr Met Ser Val Asp Arg Tyr Ile
                115                 120                 125

Ala Val Cys His Pro Val Lys Ala Leu Asp Phe Arg Thr Pro Arg Asn
                130                 135                 140

Ala Lys Ile Val Asn Val Cys Asn Trp Ile Leu Ser Ser Ala Ile Gly
145                 150                 155                 160

Leu Pro Val Met Phe Met Ala Thr Thr Lys Tyr Arg Gln Gly Ser Ile
```

```
                165                 170                 175
Asp Cys Thr Leu Thr Phe Ser His Pro Thr Trp Tyr Trp Glu Asn Leu
            180                 185                 190
Leu Lys Ile Cys Val Phe Ile Phe Ala Phe Ile Met Pro Val Leu Ile
        195                 200                 205
Ile Thr Val Cys Tyr Gly Leu Met Ile Leu Arg Leu Lys Ser Val Arg
    210                 215                 220
Met Leu Ser Gly Ser Lys Glu Lys Asp Arg Asn Leu Arg Arg Ile Thr
225                 230                 235                 240
Arg Met Val Leu Val Val Val Ala Val Phe Ile Val Cys Trp Thr Pro
                245                 250                 255
Ile His Ile Tyr Val Ile Ile Lys Ala Leu Ile Thr Ile Pro Glu Thr
            260                 265                 270
Thr Phe Gln Thr Val Ser Trp His Phe Cys Ile Ala Leu Gly Tyr Thr
        275                 280                 285
Asn Ser Cys Leu Asn Pro Val Leu Tyr Ala Phe Leu Asp Glu Asn Phe
    290                 295                 300
Lys Arg Cys Phe Arg Glu Phe Cys Ile Pro Thr Ser Ser Thr Ile Glu
305                 310                 315                 320
Gln Gln Asn Ser Ala Arg Ile Arg Gln Asn Thr Arg Glu His Pro Ser
                325                 330                 335
Thr Ala Asn Thr Val Asp Arg Thr Asn His Gln Pro Thr Leu Ala Val
            340                 345                 350
Ser Val Ala Gln Ile Phe Thr Gly Tyr Pro Ser Pro Thr His Val Glu
        355                 360                 365
Lys Pro Cys Lys Ser Cys Met Asp Arg Gly Met Arg Asn Leu Leu Pro
    370                 375                 380
Asp Asp Gly Pro Arg Gln Glu Ser Gly Glu Gly Gln Leu Gly Arg
385                 390                 395

<210> SEQ ID NO 22
<211> LENGTH: 17
<212> TYPE: PRT
<213> ORGANISM: Mus musculus

<400> SEQUENCE: 22

Glu His Pro Ser Thr Ala Asn Thr Val Asp Arg Thr Asn His Gln Cys
1               5                   10                  15
Val

<210> SEQ ID NO 23
<211> LENGTH: 22
<212> TYPE: PRT
<213> ORGANISM: Mus musculus

<400> SEQUENCE: 23

Glu His Pro Ser Thr Ala Asn Thr Val Asp Arg Thr Asn His Gln Glu
1               5                   10                  15
Pro Gln Ser Ala Glu Thr
            20

<210> SEQ ID NO 24
<211> LENGTH: 41
<212> TYPE: PRT
<213> ORGANISM: Homo sapiens

<400> SEQUENCE: 24
```

Asp Arg Thr Asn His Gln Cys Leu Pro Ile Pro Ser Leu Ser Cys Trp
1               5                   10                  15

Ala Leu Glu His Gly Arg Leu Val Val Tyr Pro Gly Pro Leu Gln Gly
            20                  25                  30

Pro Leu Val Arg Tyr Asp Leu Pro Ala
            35              40

<210> SEQ ID NO 25
<211> LENGTH: 390
<212> TYPE: PRT
<213> ORGANISM: Mus musculus

<400> SEQUENCE: 25

Met Asp Ser Ser Ala Gly Pro Gly Asn Ile Ser Asp Cys Ser Asp Pro
1               5                   10                  15

Leu Ala Pro Ala Ser Cys Ser Pro Ala Pro Gly Ser Trp Leu Asn Leu
            20                  25                  30

Ser His Val Asp Gly Asn Gln Ser Asp Pro Cys Gly Pro Asn Arg Thr
            35                  40                  45

Gly Leu Gly Gly Ser His Ser Leu Cys Pro Gln Thr Gly Ser Pro Ser
    50                  55                  60

Met Val Thr Ala Ile Thr Ile Met Ala Leu Tyr Ser Ile Val Cys Val
65                  70                  75                  80

Val Gly Leu Phe Gly Asn Phe Leu Val Met Tyr Val Ile Val Arg Tyr
                85                  90                  95

Thr Lys Met Lys Thr Ala Thr Asn Ile Tyr Ile Phe Asn Leu Ala Leu
            100                 105                 110

Ala Asp Ala Leu Ala Thr Ser Thr Leu Pro Phe Gln Ser Val Asn Tyr
            115                 120                 125

Leu Met Gly Thr Trp Pro Phe Gly Asn Ile Leu Cys Lys Ile Val Ile
    130                 135                 140

Ser Ile Asp Tyr Tyr Asn Met Phe Thr Ser Ile Phe Thr Leu Cys Thr
145                 150                 155                 160

Met Ser Val Asp Arg Tyr Ile Ala Val Cys His Pro Val Lys Ala Leu
                165                 170                 175

Asp Phe Arg Thr Pro Arg Asn Ala Lys Ile Val Asn Val Cys Asn Trp
            180                 185                 190

Ile Leu Ser Ser Ala Ile Gly Leu Pro Val Met Phe Met Ala Thr Thr
            195                 200                 205

Lys Tyr Arg Gln Gly Ser Ile Asp Cys Thr Leu Thr Phe Ser His Pro
    210                 215                 220

Thr Trp Tyr Trp Glu Asn Leu Leu Lys Ile Cys Val Phe Ile Phe Ala
225                 230                 235                 240

Phe Ile Met Pro Val Leu Ile Ile Thr Val Cys Tyr Gly Leu Met Ile
                245                 250                 255

Leu Arg Leu Lys Ser Val Arg Met Leu Ser Gly Ser Lys Glu Lys Asp
            260                 265                 270

Arg Asn Leu Arg Arg Ile Thr Arg Met Val Leu Val Val Val Ala Val
            275                 280                 285

Phe Ile Val Cys Trp Thr Pro Ile His Ile Tyr Val Ile Ile Lys Ala
    290                 295                 300

Leu Ile Thr Ile Pro Glu Thr Thr Phe Gln Thr Val Ser Trp His Phe
305                 310                 315                 320

Cys Ile Ala Leu Gly Tyr Thr Asn Ser Cys Leu Asn Pro Val Leu Tyr
                325                 330                 335

Ala Phe Leu Asp Glu Asn Phe Lys Arg Cys Phe Arg Glu Phe Cys Ile
            340                 345                 350

Pro Thr Ser Ser Thr Ile Glu Gln Gln Asn Ser Ala Arg Ile Arg Gln
            355                 360                 365

Asn Thr Arg Glu His Pro Ser Thr Ala Asn Thr Val Asp Arg Thr Asn
            370                 375                 380

His Gln Val Cys Ala Phe
385                 390

<210> SEQ ID NO 26
<211> LENGTH: 391
<212> TYPE: PRT
<213> ORGANISM: Mus musculus

<400> SEQUENCE: 26

Met Asp Ser Ser Ala Gly Pro Gly Asn Ile Ser Asp Cys Ser Asp Pro
1               5                   10                  15

Leu Ala Pro Ala Ser Cys Ser Pro Ala Pro Gly Ser Trp Leu Asn Leu
            20                  25                  30

Ser His Val Asp Gly Asn Gln Ser Asp Pro Cys Gly Pro Asn Arg Thr
        35                  40                  45

Gly Leu Gly Gly Ser His Ser Leu Cys Pro Gln Thr Gly Ser Pro Ser
    50                  55                  60

Met Val Thr Ala Ile Thr Ile Met Ala Leu Tyr Ser Ile Val Cys Val
65                  70                  75                  80

Val Gly Leu Phe Gly Asn Phe Leu Val Met Tyr Val Ile Val Arg Tyr
            85                  90                  95

Thr Lys Met Lys Thr Ala Thr Asn Ile Tyr Ile Phe Asn Leu Ala Leu
            100                 105                 110

Ala Asp Ala Leu Ala Thr Ser Thr Leu Pro Phe Gln Ser Val Asn Tyr
            115                 120                 125

Leu Met Gly Thr Trp Pro Phe Gly Asn Ile Leu Cys Lys Ile Val Ile
    130                 135                 140

Ser Ile Asp Tyr Tyr Asn Met Phe Thr Ser Ile Phe Thr Leu Cys Thr
145                 150                 155                 160

Met Ser Val Asp Arg Tyr Ile Ala Val Cys His Pro Val Lys Ala Leu
            165                 170                 175

Asp Phe Arg Thr Pro Arg Asn Ala Lys Ile Val Asn Val Cys Asn Trp
            180                 185                 190

Ile Leu Ser Ser Ala Ile Gly Leu Pro Val Met Phe Met Ala Thr Thr
    195                 200                 205

Lys Tyr Arg Gln Gly Ser Ile Asp Cys Thr Leu Thr Phe Ser His Pro
210                 215                 220

Thr Trp Tyr Trp Glu Asn Leu Leu Lys Ile Cys Val Phe Ile Phe Ala
225                 230                 235                 240

Phe Ile Met Pro Val Leu Ile Ile Thr Val Cys Tyr Gly Leu Met Ile
            245                 250                 255

Leu Arg Leu Lys Ser Val Arg Met Leu Ser Gly Ser Lys Glu Lys Asp
            260                 265                 270

Arg Asn Leu Arg Arg Ile Thr Arg Met Val Leu Val Val Val Ala Val
            275                 280                 285

Phe Ile Val Cys Trp Thr Pro Ile His Ile Tyr Val Ile Ile Lys Ala
    290                 295                 300

Leu Ile Thr Ile Pro Glu Thr Thr Phe Gln Thr Val Ser Trp His Phe

```
305                 310                 315                 320
Cys Ile Ala Leu Gly Tyr Thr Asn Ser Cys Leu Asn Pro Val Leu Tyr
                325                 330                 335

Ala Phe Leu Asp Glu Asn Phe Lys Arg Cys Phe Arg Glu Phe Cys Ile
            340                 345                 350

Pro Thr Ser Ser Thr Ile Glu Gln Gln Asn Ser Ala Arg Ile Arg Gln
            355                 360                 365

Asn Thr Arg Glu His Pro Ser Thr Ala Asn Thr Val Asp Arg Thr Asn
        370                 375                 380

His Gln Lys Ile Asp Leu Phe
385                 390

<210> SEQ ID NO 27
<211> LENGTH: 409
<212> TYPE: PRT
<213> ORGANISM: Mus musculus

<400> SEQUENCE: 27

Met Asp Ser Ser Ala Gly Pro Gly Asn Ile Ser Asp Cys Ser Asp Pro
1               5                   10                  15

Leu Ala Pro Ala Ser Cys Ser Pro Ala Pro Gly Ser Trp Leu Asn Leu
            20                  25                  30

Ser His Val Asp Gly Asn Gln Ser Asp Pro Cys Gly Pro Asn Arg Thr
        35                  40                  45

Gly Leu Gly Gly Ser His Ser Leu Cys Pro Gln Thr Gly Ser Pro Ser
    50                  55                  60

Met Val Thr Ala Ile Thr Ile Met Ala Leu Tyr Ser Ile Val Cys Val
65                  70                  75                  80

Val Gly Leu Phe Gly Asn Phe Leu Val Met Tyr Val Ile Val Arg Tyr
                85                  90                  95

Thr Lys Met Lys Thr Ala Thr Asn Ile Tyr Ile Phe Asn Leu Ala Leu
            100                 105                 110

Ala Asp Ala Leu Ala Thr Ser Thr Leu Pro Phe Gln Ser Val Asn Tyr
        115                 120                 125

Leu Met Gly Thr Trp Pro Phe Gly Asn Ile Leu Cys Lys Ile Val Ile
    130                 135                 140

Ser Ile Asp Tyr Tyr Asn Met Phe Thr Ser Ile Phe Thr Leu Cys Thr
145                 150                 155                 160

Met Ser Val Asp Arg Tyr Ile Ala Val Cys His Pro Val Lys Ala Leu
                165                 170                 175

Asp Phe Arg Thr Pro Arg Asn Ala Lys Ile Val Asn Val Cys Asn Trp
            180                 185                 190

Ile Leu Ser Ser Ala Ile Gly Leu Pro Val Met Phe Met Ala Thr Thr
        195                 200                 205

Lys Tyr Arg Gln Gly Ser Ile Asp Cys Thr Leu Thr Phe Ser His Pro
    210                 215                 220

Thr Trp Tyr Trp Glu Asn Leu Leu Lys Ile Cys Val Phe Ile Phe Ala
225                 230                 235                 240

Phe Ile Met Pro Val Leu Ile Ile Thr Val Cys Tyr Gly Leu Met Ile
                245                 250                 255

Leu Arg Leu Lys Ser Val Arg Met Leu Ser Gly Ser Lys Glu Lys Asp
            260                 265                 270

Arg Asn Leu Arg Arg Ile Thr Arg Met Val Leu Val Val Val Ala Val
        275                 280                 285
```

```
Phe Ile Val Cys Trp Thr Pro Ile His Ile Tyr Val Ile Ile Lys Ala
            290                 295                 300

Leu Ile Thr Ile Pro Glu Thr Thr Phe Gln Thr Val Ser Trp His Phe
305                 310                 315                 320

Cys Ile Ala Leu Gly Tyr Thr Asn Ser Cys Leu Asn Pro Val Leu Tyr
                325                 330                 335

Ala Phe Leu Asp Glu Asn Phe Lys Arg Cys Phe Arg Glu Phe Cys Ile
            340                 345                 350

Pro Thr Ser Ser Thr Ile Glu Gln Gln Asn Ser Ala Arg Ile Arg Gln
            355                 360                 365

Asn Thr Arg Glu His Pro Ser Thr Ala Asn Thr Val Asp Arg Thr Asn
            370                 375                 380

His Gln Lys Leu Leu Met Trp Arg Ala Met Pro Thr Phe Lys Arg His
385                 390                 395                 400

Leu Ala Ile Met Leu Ser Leu Asp Asn
                405

<210> SEQ ID NO 28
<211> LENGTH: 444
<212> TYPE: PRT
<213> ORGANISM: Mus musculus

<400> SEQUENCE: 28

Met Asp Ser Ser Ala Gly Pro Gly Asn Ile Ser Asp Cys Ser Asp Pro
1               5                   10                  15

Leu Ala Pro Ala Ser Cys Ser Pro Ala Pro Gly Ser Trp Leu Asn Leu
                20                  25                  30

Ser His Val Asp Gly Asn Gln Ser Asp Pro Cys Gly Pro Asn Arg Thr
            35                  40                  45

Gly Leu Gly Gly Ser His Ser Leu Cys Pro Gln Thr Gly Ser Pro Ser
50                  55                  60

Met Val Thr Ala Ile Thr Ile Met Ala Leu Tyr Ser Ile Val Cys Val
65                  70                  75                  80

Val Gly Leu Phe Gly Asn Phe Leu Val Met Tyr Val Ile Val Arg Tyr
                85                  90                  95

Thr Lys Met Lys Thr Ala Thr Asn Ile Tyr Ile Phe Asn Leu Ala Leu
                100                 105                 110

Ala Asp Ala Leu Ala Thr Ser Thr Leu Pro Phe Gln Ser Val Asn Tyr
            115                 120                 125

Leu Met Gly Thr Trp Pro Phe Gly Asn Ile Leu Cys Lys Ile Val Ile
130                 135                 140

Ser Ile Asp Tyr Tyr Asn Met Phe Thr Ser Ile Phe Thr Leu Cys Thr
145                 150                 155                 160

Met Ser Val Asp Arg Tyr Ile Ala Val Cys His Pro Val Lys Ala Leu
                165                 170                 175

Asp Phe Arg Thr Pro Arg Asn Ala Lys Ile Val Asn Val Cys Asn Trp
            180                 185                 190

Ile Leu Ser Ser Ala Ile Gly Leu Pro Val Met Phe Met Ala Thr Thr
            195                 200                 205

Lys Tyr Arg Gln Gly Ser Ile Asp Cys Thr Leu Thr Phe Ser His Pro
210                 215                 220

Thr Trp Tyr Trp Glu Asn Leu Leu Lys Ile Cys Val Phe Ile Phe Ala
225                 230                 235                 240

Phe Ile Met Pro Val Leu Ile Ile Thr Val Cys Tyr Gly Leu Met Ile
                245                 250                 255
```

-continued

```
Leu Arg Leu Lys Ser Val Arg Met Leu Ser Gly Ser Lys Glu Lys Asp
            260                 265                 270

Arg Asn Leu Arg Arg Ile Thr Arg Met Val Leu Val Val Ala Val
            275                 280                 285

Phe Ile Val Cys Trp Thr Pro Ile His Ile Tyr Val Ile Lys Ala
            290                 295                 300

Leu Ile Thr Ile Pro Glu Thr Thr Phe Gln Thr Val Ser Trp His Phe
305                 310                 315                 320

Cys Ile Ala Leu Gly Tyr Thr Asn Ser Cys Leu Asn Pro Val Leu Tyr
                    325                 330                 335

Ala Phe Leu Asp Glu Asn Phe Lys Arg Cys Phe Arg Glu Phe Cys Ile
                    340                 345                 350

Pro Thr Ser Ser Thr Ile Glu Gln Gln Asn Ser Ala Arg Ile Arg Gln
                    355                 360                 365

Asn Thr Arg Glu His Pro Ser Thr Ala Asn Thr Val Asp Arg Thr Asn
                    370                 375                 380

His Gln Ala Pro Cys Ala Cys Val Pro Gly Ala Asn Arg Gly Gln Thr
385                 390                 395                 400

Lys Ala Ser Asp Leu Leu Asp Leu Glu Leu Glu Thr Val Gly Ser His
                    405                 410                 415

Gln Ala Asp Ala Glu Thr Asn Pro Gly Pro Tyr Glu Gly Ser Lys Cys
                    420                 425                 430

Ala Glu Pro Leu Ala Ile Ser Leu Val Pro Leu Tyr
                    435                 440

<210> SEQ ID NO 29
<211> LENGTH: 398
<212> TYPE: PRT
<213> ORGANISM: Mus musculus

<400> SEQUENCE: 29

Met Asp Ser Ser Ala Gly Pro Gly Asn Ile Ser Asp Cys Ser Asp Pro
1               5                   10                  15

Leu Ala Pro Ala Ser Cys Ser Pro Ala Pro Gly Ser Trp Leu Asn Leu
                20                  25                  30

Ser His Val Asp Gly Asn Gln Ser Asp Pro Cys Gly Pro Asn Arg Thr
            35                  40                  45

Gly Leu Gly Gly Ser His Ser Leu Cys Pro Gln Thr Gly Ser Pro Ser
    50                  55                  60

Met Val Thr Ala Ile Thr Ile Met Ala Leu Tyr Ser Ile Val Cys Val
65                  70                  75                  80

Val Gly Leu Phe Gly Asn Phe Leu Val Met Tyr Val Ile Val Arg Tyr
                85                  90                  95

Thr Lys Met Lys Thr Ala Thr Asn Ile Tyr Ile Phe Asn Leu Ala Leu
            100                 105                 110

Ala Asp Ala Leu Ala Thr Ser Thr Leu Pro Phe Gln Ser Val Asn Tyr
            115                 120                 125

Leu Met Gly Thr Trp Pro Phe Gly Asn Ile Leu Cys Lys Ile Val Ile
    130                 135                 140

Ser Ile Asp Tyr Tyr Asn Met Phe Thr Ser Ile Phe Thr Leu Cys Thr
145                 150                 155                 160

Met Ser Val Asp Arg Tyr Ile Ala Val Cys His Pro Val Lys Ala Leu
                    165                 170                 175

Asp Phe Arg Thr Pro Arg Asn Ala Lys Ile Val Asn Val Cys Asn Trp
```

-continued

```
                    180                 185                 190
Ile Leu Ser Ser Ala Ile Gly Leu Pro Val Met Phe Met Ala Thr Thr
                195                 200                 205
Lys Tyr Arg Gln Gly Ser Ile Asp Cys Thr Leu Thr Phe Ser His Pro
            210                 215                 220
Thr Trp Tyr Trp Glu Asn Leu Leu Lys Ile Cys Val Phe Ile Phe Ala
225                 230                 235                 240
Phe Ile Met Pro Val Leu Ile Ile Thr Val Cys Tyr Gly Leu Met Ile
                245                 250                 255
Leu Arg Leu Lys Ser Val Arg Met Leu Ser Gly Ser Lys Glu Lys Asp
            260                 265                 270
Arg Asn Leu Arg Arg Ile Thr Arg Met Val Leu Val Val Val Ala Val
        275                 280                 285
Phe Ile Val Cys Trp Thr Pro Ile His Ile Tyr Val Ile Ile Lys Ala
    290                 295                 300
Leu Ile Thr Ile Pro Glu Thr Thr Phe Gln Thr Val Ser Trp His Phe
305                 310                 315                 320
Cys Ile Ala Leu Gly Tyr Thr Asn Ser Cys Leu Asn Pro Val Leu Tyr
                325                 330                 335
Ala Phe Leu Asp Glu Asn Phe Lys Arg Cys Phe Arg Glu Phe Cys Ile
            340                 345                 350
Pro Thr Ser Ser Thr Ile Glu Gln Gln Asn Ser Ala Arg Ile Arg Gln
        355                 360                 365
Asn Thr Arg Glu His Pro Ser Thr Ala Asn Thr Val Asp Arg Thr Asn
    370                 375                 380
His Gln Leu Glu Asn Leu Glu Ala Glu Thr Ala Pro Leu Pro
385                 390                 395

<210> SEQ ID NO 30
<211> LENGTH: 13
<212> TYPE: PRT
<213> ORGANISM: Mus musculus

<400> SEQUENCE: 30

Leu Glu Asn Leu Glu Ala Glu Thr Thr Ala Pro Leu Pro
1               5                   10

<210> SEQ ID NO 31
<211> LENGTH: 4
<212> TYPE: PRT
<213> ORGANISM: Mus musculus

<400> SEQUENCE: 31

Val Arg Ser Leu
1

<210> SEQ ID NO 32
<211> LENGTH: 5
<212> TYPE: PRT
<213> ORGANISM: Mus musculus

<400> SEQUENCE: 32

Lys Ile Asp Leu Phe
1               5

<210> SEQ ID NO 33
<211> LENGTH: 46
<212> TYPE: PRT
<213> ORGANISM: Mus musculus
```

```
<400> SEQUENCE: 33

Pro Thr Leu Ala Val Ser Val Ala Gln Ile Phe Thr Gly Tyr Pro Ser
1               5                   10                  15

Pro Thr His Val Glu Lys Pro Cys Lys Ser Cys Cys Met Asp Arg Gly
                20                  25                  30

Met Arg Asn Leu Leu Pro Asp Asp Gly Pro Arg Leu Gly Arg
                35                  40                  45

<210> SEQ ID NO 34
<211> LENGTH: 7
<212> TYPE: PRT
<213> ORGANISM: Mus musculus

<400> SEQUENCE: 34

Arg Asn Glu Glu Pro Ser Ser
1               5

<210> SEQ ID NO 35
<211> LENGTH: 15
<212> TYPE: PRT
<213> ORGANISM: Mus musculus

<400> SEQUENCE: 35

Lys Lys Lys Leu Asp Ser Gln Arg Gly Cys Val Gln His Pro Val
1               5                   10                  15

<210> SEQ ID NO 36
<211> LENGTH: 5
<212> TYPE: PRT
<213> ORGANISM: Artificial Sequence
<220> FEATURE:
<223> OTHER INFORMATION: basic unit of a linking peptide

<400> SEQUENCE: 36

Gly Gly Gly Gly Ser
1               5

<210> SEQ ID NO 37
<211> LENGTH: 24
<212> TYPE: DNA
<213> ORGANISM: Artificial Sequence
<220> FEATURE:
<223> OTHER INFORMATION: antisense primer used in RT-PCR amplification
      of mouse brain RNA

<400> SEQUENCE: 37
ccacactgct caccagctca tccc                                              24

<210> SEQ ID NO 38
<211> LENGTH: 48
<212> TYPE: DNA
<213> ORGANISM: Artificial Sequence
<220> FEATURE:
<223> OTHER INFORMATION: antisense primer derived from exon 7 of the
      mouse MOR-1 gene

<400> SEQUENCE: 38
tgtccatgca actcttgcag ggtttttcaa catgagtcgg agaaggat                    48

<210> SEQ ID NO 39
<211> LENGTH: 18
<212> TYPE: DNA
<213> ORGANISM: Artificial Sequence
<220> FEATURE:
```

```
<223> OTHER INFORMATION: sense primer designed from exon 3 used in
      RT-PCR of mouse brain RNA

<400> SEQUENCE: 39
gggaacaccc ctccacgg                                              18

<210> SEQ ID NO 40
<211> LENGTH: 24
<212> TYPE: DNA
<213> ORGANISM: Artificial Sequence
<220> FEATURE:
<223> OTHER INFORMATION: antisense primer from exon 5a used in RT-PCR
      of mouse brain RNA

<400> SEQUENCE: 40
ggtgtgcttc tcccagttct gtgt                                       24

<210> SEQ ID NO 41
<211> LENGTH: 23
<212> TYPE: DNA
<213> ORGANISM: Artificial Sequence
<220> FEATURE:
<223> OTHER INFORMATION: sense primer designed from exon 1a used in
      RT-PCR of mouse brain RNA

<400> SEQUENCE: 41
cctccaggct catttcagag aga                                        23

<210> SEQ ID NO 42
<211> LENGTH: 22
<212> TYPE: DNA
<213> ORGANISM: Artificial Sequence
<220> FEATURE:
<223> OTHER INFORMATION: antisense primer from exon 1 used in RT-PCR
      of mouse brain RNA

<400> SEQUENCE: 42
caggaagttt ccaaagaggc cc                                         22

<210> SEQ ID NO 43
<211> LENGTH: 23
<212> TYPE: DNA
<213> ORGANISM: Artificial Sequence
<220> FEATURE:
<223> OTHER INFORMATION: antisense primer from exon 2 used in RT-PCR
      of mouse brain RNA

<400> SEQUENCE: 43
gggcaggtgg tagtggctaa ggc                                        23

<210> SEQ ID NO 44
<211> LENGTH: 5
<212> TYPE: PRT
<213> ORGANISM: Mus musculus

<400> SEQUENCE: 44

Lys Ile Asp Leu Glu
1               5

<210> SEQ ID NO 45
<211> LENGTH: 23
<212> TYPE: PRT
<213> ORGANISM: Mus musculus

<400> SEQUENCE: 45

Lys Leu Leu Met Trp Arg Ala Met Pro Thr Phe Lys Arg His Leu Ala
```

```
1               5                10               15
Ile Met Leu Ser Leu Asp Asn
                20

<210> SEQ ID NO 46
<211> LENGTH: 30
<212> TYPE: DNA
<213> ORGANISM: Artificial Sequence
<220> FEATURE:
<223> OTHER INFORMATION: antisense primer corresponding to the 3' UTR
      of exon 3a used in PCR

<400> SEQUENCE: 46
gatcagaatt tggtgcccta ctccctctct                                      30
```

What is claimed is:

1. An isolated MOR-1C splice variant polypeptide that consists essentially of the amino acid residues depicted in SEQ ID NO: 17.

2. An isolated MOR-1D splice variant polypeptide that consists essentially of the amino acid residues depicted in SEQ ID NO: 19.

3. An isolated MOR-1E splice variant polypeptide that consists essentially of the amino acid residues depicted in SEQ ID NO: 20.

4. An isolated MOR-1F splice variant polypeptide that consists essentially of the amino acid residues depicted in SEQ ID NO: 28.

5. An isolated MOR-1A splice variant polypeptide that consists essentially of the amino acid residues depicted in SEQ ID NO: 25.

6. An isolated MOR-1B II splice variant polypeptide that consists essentially of the amino acid residues depicted in SEQ ID NO: 27.

7. An isolated MOR-1B I splice variant polypeptide that consists essentially of the amino acid residues depicted in SEQ ID NO: 26.

8. The polypeptide as in any of claims 1, 2, 3, 4, 5, 6, or 7 polypeptide comprises a heterodimeric or homodimeric composition.

* * * * *